US011352319B2

(12) United States Patent
Miyake et al.

(10) Patent No.: US 11,352,319 B2
(45) Date of Patent: Jun. 7, 2022

(54) METHOD FOR PRODUCING CARBAMATE AND METHOD FOR PRODUCING ISOCYANATE

(71) Applicant: ASAHI KASEI KABUSHIKI KAISHA, Tokyo (JP)

(72) Inventors: Nobuhisa Miyake, Tokyo (JP); Koichi Nakaoka, Tokyo (JP); Yusuke Sakurai, Tokyo (JP); Midori Nagamoto, Tokyo (JP); Kazuhiro Takagaki, Tokyo (JP); Masaaki Shinohata, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/052,548

(22) PCT Filed: May 15, 2019

(86) PCT No.: PCT/JP2019/019415
§ 371 (c)(1),
(2) Date: Nov. 3, 2020

(87) PCT Pub. No.: WO2019/221210
PCT Pub. Date: Nov. 21, 2019

(65) Prior Publication Data
US 2021/0179548 A1 Jun. 17, 2021

(30) Foreign Application Priority Data
May 15, 2018 (JP) .............................. JP2018-094157

(51) Int. Cl.
*C07C 269/04* (2006.01)
*C07C 263/04* (2006.01)
*C07D 307/52* (2006.01)
*C07D 307/54* (2006.01)

(52) U.S. Cl.
CPC .......... *C07C 269/04* (2013.01); *C07C 263/04* (2013.01); *C07D 307/52* (2013.01); *C07D 307/54* (2013.01)

(58) Field of Classification Search
CPC ................................................. C07C 269/04
See application file for complete search history.

(56) References Cited

U.S. PATENT DOCUMENTS

| 3,627,813 | A  | 12/1971 | Abbate et al.      |
|-----------|----|---------|--------------------|
| 4,381,404 | A  | 4/1983  | Buysch et al.      |
| 4,388,238 | A  | 6/1983  | Heitkamper et al.  |
| 4,523,030 | A  | 6/1985  | Haas et al.        |
| 4,713,476 | A  | 12/1987 | Merger et al.      |
| 4,847,408 | A  | 7/1989  | Frosch et al.      |
| 5,051,188 | A  | 9/1991  | Spiske et al.      |
| 5,360,931 | A  | 11/1994 | Bohmholdt et al.   |
| 5,449,818 | A  | 9/1995  | Biskup et al.      |
| 5,633,396 | A  | 5/1997  | Bischof et al.     |
| 5,744,633 | A  | 4/1998  | Wilmes et al.      |
| 8,957,241 | B2 * | 2/2015 | Shinohata ............. C07C 269/06 560/159 |
| 2007/0015932 | A1 | 1/2007 | Fujita et al.    |
| 2010/0069665 | A1 | 3/2010 | Shinohata et al. |
| 2011/0054211 | A1 | 3/2011 | Shinohata et al. |
| 2013/0178645 | A1 | 7/2013 | Shinohata et al. |
| 2020/0216387 | A1 | 7/2020 | Miyake et al.    |

FOREIGN PATENT DOCUMENTS

| DE | 4217019 A1    | 11/1993 |
|----|---------------|---------|
| EP | 0289840 A1    | 11/1988 |
| EP | 0568782 A2    | 11/1993 |
| EP | 0657420 A1    | 6/1995  |
| JP | 48-018217 A   | 6/1973  |
| JP | 48-018217 B   | 6/1973  |
| JP | 57-091967 A   | 6/1982  |
| JP | 57-112363 A   | 7/1982  |
| JP | 58-105954 A   | 6/1983  |
| JP | 60-011440 A   | 1/1985  |
| JP | 03-170452 A   | 7/1991  |
| JP | 06-041045 A   | 2/1994  |
| JP | 06-234723 A   | 8/1994  |
| JP | 09-012525 A   | 1/1997  |
| JP | 2003-321458 A | 11/2003 |
| JP | 2005-220129 A | 8/2005  |
| JP | 2006-143645 A | 6/2006  |

(Continued)

OTHER PUBLICATIONS

Chaoyong Wu et al., "Synthesis of urea derivatives from amines and CO2 in the absence of catalyst and solvent", Green Chemistry, vol. 12, No. 10, 2010, pp. 1811-1816.
Search Report dated May 27, 2021 in European Patent Application 19803118.9.
Written Opinion issued in corresponding International Patent Application No. PCT/JP2019/019415, dated Jul. 30, 2019.
Hofmann, Berichte der Deutechen Chemischen Gesellschaft, vol. 3, p. 653, 1870 (with partial translation).
International Search Report issued in corresponding International Patent Application No. PCT/JP2019/019415, dated Jul. 30, 2019.

*Primary Examiner* — Golam M Shameem

(74) *Attorney, Agent, or Firm* — Morgan, Lewis & Bockius LLP

(57) ABSTRACT

The present invention provides a method for producing a carbamate that includes a step (1) and a step (2) described below:

(1) a step of producing a compound (A) having a urea linkage, using an organic primary amine having at least one primary amino group per molecule and at least one compound selected from among carbon dioxide and carbonic acid derivatives, at a temperature lower than the thermal dissociation temperature of the urea linkage; and (2) a step of reacting the compound (A) with a carbonate ester to produce a carbamate.

11 Claims, 1 Drawing Sheet

(56) References Cited

FOREIGN PATENT DOCUMENTS

| | | | |
|---|---|---|---|
| JP | 2007-022932 | A | 2/2007 |
| JP | 2012-107095 | A | 6/2012 |
| JP | 2012-111711 | A | 6/2012 |
| WO | 2005/063698 | A1 | 7/2005 |
| WO | 2008/084824 | A1 | 7/2008 |
| WO | 2009/139061 | A1 | 11/2009 |
| WO | 2012/115110 | A1 | 8/2012 |
| WO | 2018/212206 | A1 | 11/2018 |

* cited by examiner

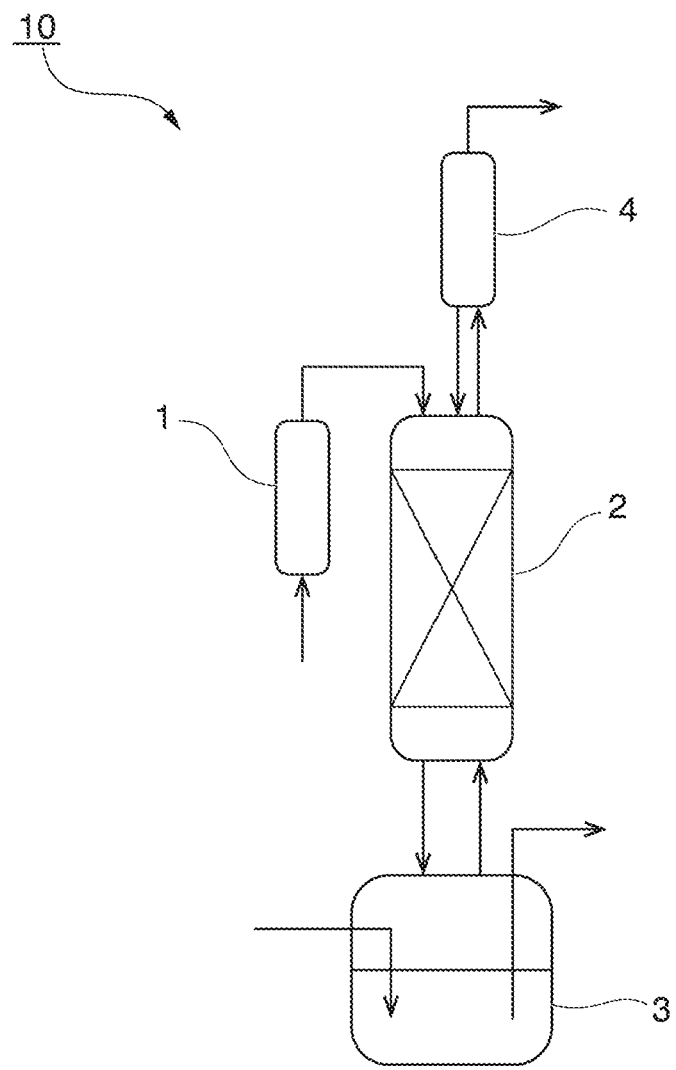

METHOD FOR PRODUCING CARBAMATE AND METHOD FOR PRODUCING ISOCYANATE

TECHNICAL FIELD

The present invention relates to a method for producing a carbamate and a method for producing an isocyanate.

Priority is claimed on Japanese Patent Application No. 2018-094157, filed May 15, 2018, the content of which is incorporated herein by reference.

BACKGROUND ART

Isocyanates are widely used as production raw materials for polyurethane foams, coating materials, and adhesives and the like. The main industrial production method for isocyanates involves a reaction between an amine compound and phosgene (the phosgene method), and almost the entire world production volume is produced using the phosgene method.

For example, Patent Document 1 discloses a method for producing (cyclic) aliphatic diisocyanates by the phosgene method, and Patent Document 2 discloses a method for producing aromatic diisocyanates by the phosgene method. Further, Patent Document 3 discloses a method for producing a (cyclic) aliphatic triisocyanate by phosgenating a triamine, in a vapor phase of at least 200° C. but not more than 600° C., in a cylindrical reaction vessel with no moving parts, with the flow rate maintained at a rate of at least 3 m/s. Furthermore, Patent Document 4 discloses a method for producing 2,6,2'-triisocyanatoethyl hexanoate by phosgenating 2,6,2'-triaminoethyl hexanoate trihydrochloride in the presence of at least one catalyst selected from the group consisting of quaternary ammonium salts, pyridinium salts and phosphonium salts.

However, the phosgene method has many problems.

Firstly, the method uses a large amount of phosgene as a raw material. Phosgene is extremely toxic, and therefore particular attention must be paid to handling to prevent worker exposure, and special equipment is required for removing waste material.

Secondly, in the phosgene method, because highly corrosive hydrogen chloride is produced in large volume as a by-product, a process for removing this hydrogen chloride is necessary. Moreover, in many cases, the produced isocyanate contains hydrolyzable chlorine. This can sometimes have adverse effects on the weather resistance and heat resistance of polyurethane products when an isocyanate produced by the phosgene method is used.

Against this type of background, a method for producing isocyanate compounds that does not use phosgene would be desirable. One proposed method for producing isocyanate compounds without using phosgene is a method that involves the thermal decomposition of a carbamate. Obtaining an isocyanate and a hydroxy compound by thermal decomposition of a carbamate is already known (for example, see non-Patent Document 1). The basic reaction can be exemplified by the formula shown below.

[Chemical formula 1]

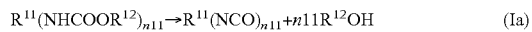

(In general formula (a), $R^{11}$ represents an n11-valent organic group. R12 represents a monovalent organic group. Further, n11 is an integer of 1 or greater.)

One example of a method for producing a carbamate using urea is a method in which a diamine, an alcohol and urea are reacted together and converted to a carbamate (for example, see Patent Document 5). Further, another example is a method in which a bisurea is produced from an aliphatic primary polyamine, urea and an alcohol, and a carbamate is then produced from the bisurea (for example, see Patent Document 6). Furthermore, another example is a production method that includes a first step of partially reacting urea and an alcohol, and a second step of supplying a diamine to produce a carbamate (for example, see Patent Document 7). Moreover, an example of another method is a method for producing an isocyanate by first producing a carbamate, for example by reacting an organic primary amine and a diaryl carbonate, and subsequently subjecting that carbamate to thermal decomposition in a separate reactor that is connected by a line to the reactor used for conducting the first reaction (for example, see Patent Document 8).

PRIOR ART LITERATURE

Patent Documents

Patent Document 1: European Patent Publication No. 0289840
Patent Document 2: German Patent Publication No. 4217019
Patent Document 3: Japanese Unexamined Patent Application, First Publication No. Hei 9-012525
Patent Document 4: Japanese Unexamined Patent Application, First Publication No. Hei 6-234723
Patent Document 5: U.S. Pat. No. 4,713,476
Patent Document 6: European Patent Publication No. 0568782
Patent Document 7: European Patent Publication No. 0657420
Patent Document 8: International Patent Publication No. 2009/139061

Non-Patent Document

Non-Patent Document 1: Berichte der Deutschen Chemischen Gesellschaft, vol. 3, page 653, 1870

SUMMARY OF INVENTION

Problems to be Solved by the Invention

As mentioned above, examples of methods for producing isocyanates without using phosgene do exist, but these examples relate to specific isocyanates, and there are no examples of methods suitable for producing trifunctional isocyanates or isocyanates having an amino acid skeleton such as 2,6,2'-triisocyanatoethyl hexanoate which have been reported using the phosgene method. Further, the market circulation of carbonate esters such as diaryl carbonates are often insufficient to enable large-scale isocyanate production on a commercial basis. Furthermore, as described in the above Patent Documents 5 to 7, methods for producing carbamates from an amine compound, urea and a hydroxy compound have been disclosed, but the reaction requires high temperature, and in those cases where the carbamate is thermally unstable, unwanted side reactions often occur.

The present invention has been developed in light of the above circumstances, and provides a method for producing a carbamate without using phosgene and with a reduction in the amount of carbonate ester used, and a method for producing an isocyanate that uses a carbamate obtained using the above production method.

Means for Solving the Problems

In other words, the present invention includes the aspects described below.

A method for producing a carbamate according to a first aspect of the present invention includes a step (1) and a step (2) described below:

(1) a step of producing a compound (A) having a urea linkage, using an organic primary amine having at least one primary amino group per molecule and at least one compound selected from among carbon dioxide and carbonic acid derivatives, at a temperature lower than the thermal dissociation temperature of the urea linkage; and (2) a step of reacting the compound (A) with a carbonate ester to produce a carbamate.

In the step (1), when producing the compound (A) using the organic primary amine and carbon dioxide, the reaction may be conducted while extracting, from the reaction system, the water produced by the reaction between the organic primary amine and carbon dioxide.

The carbonic acid derivative may be at least one compound selected from among N-unsubstituted carbamate esters, N,N'-disubstituted ureas, N-substituted ureas and urea.

The organic primary amine may have two or three primary amino groups per molecule.

The organic primary amine may be at least one compound selected from among amino acid esters and salts of amino acid esters.

In the method for producing a carbamate according to the first aspect described above, the organic primary amine may have a carboxy group, and the method may also include a step (Y) described below, either before the step (1), or after the step (1) but before the step (2):

(Y) a step of esterifying the carboxy group of the organic primary amine, or esterifying the carboxy group of the compound (A) obtained in the step (1).

The organic primary amine may have three primary amino groups per molecule.

The molar amount of the carbonic acid derivative may be less than 0.5 times the molar amount of primary amino groups in the organic primary amine.

In the step (1), the reaction may be conducted in the presence of an aromatic hydroxy compound.

A method for producing an isocyanate according to a second aspect of the present invention is a method for producing an isocyanate by subjecting the carbamate obtained using the production method according to the first aspect described above to a thermal decomposition reaction.

Effects of the Invention

The method for producing a carbamate according to the aspect described above uses no phosgene, and enables a reduction in the amount of carbonate ester used. The method for producing an isocyanate according to the aspect described above is a method that uses the carbamate obtained in the above production method, and is capable of producing numerous varieties of isocyanates.

BRIEF DESCRIPTION OF THE DRAWINGS

FIG. 1 is a schematic diagram illustrating the structure of a thermal decomposition reactor used in the examples.

EMBODIMENTS FOR CARRYING OUT THE INVENTION

Embodiments for carrying out the present invention (hereafter referred to as "embodiments of the present invention") are described below in detail. The following embodiments of the present invention are provided as examples for describing the present invention, but the present invention is not limited to the following embodiments. The present invention can also be carried out by appropriate modification of the following embodiments within the scope of the invention.

<<Method for Producing Carbamate>>

A method for producing a carbamate according to this embodiment of the present invention is a method that includes a step (1) and a step (2) described below:

(1) a step of producing a compound (A) having a urea linkage, using an organic primary amine having at least one primary amino group per molecule and at least one compound selected from among carbon dioxide and carbonic acid derivatives, at a temperature lower than the thermal dissociation temperature of the urea linkage; and (2) a step of reacting the compound (A) with a carbonate ester to produce a carbamate.

By adopting the configuration described above, the method for producing a carbamate according to this embodiment is capable of producing numerous varieties of carbamates without using phosgene, and using a reduced amount of carbonate ester.

Each of the steps of the method for producing a carbamate according to this embodiment is described below in detail.

<Step (1)>

In step (1), a compound (A) having a urea linkage is produced using an organic primary amine having at least one primary amino group per molecule and at least one compound selected from among carbon dioxide and carbonic acid derivatives, at a temperature lower than the thermal dissociation temperature of the urea linkage. The "thermal dissociation temperature" mentioned in this embodiment indicates the temperature at which thermal dissociation of the compound having a urea linkage proceeds. Typically, the thermal dissociation temperature can be measured using a method in which the temperature of a sample is either changed or maintained by a fixed program while the weight of the sample is measured as a function of temperature, by determining the temperature at which a weight reduction of the compound starts to occur. The sample is heated at a rate of temperature increase of 10° C. per minute under a stream of an inert gas typified by nitrogen, and the temperature at which a weight reduction of 3%, or preferably 5%, occurs relative to the initial weight of the sample is deemed the thermal dissociation temperature.

In this case, depending on the type of compound used, the "weight reduction" mentioned above may describe not only the case of weight reduction caused by thermal dissociation of the urea linkage, and includes other cases of weight reduction due to the thermal dissociation of a functional group other than the urea linkage in the compound, but considering the aim of the present embodiment, it is preferable to employ weight reduction caused by thermal dissociation of the urea linkage. In this case, the method used for determining whether thermal dissociation is occurring in the urea linkage or in another functional group other than the urea linkage in the compound may employ a method in which, for example, the exhaust gas from the thermogravimetric device is introduced into a mass spectrometer to analyze the components contained within the exhaust gas. Further, depending on the type of compound used, even if thermal dissociation of the urea linkage occurs, because the molecular weight of the thermal dissociation product may be large (in many cases, because the boiling point of the thermal dissociation product is high), the thermal dissociation reaction may sometimes be undetectable as a weight reduction. In these type of cases, a method such as differential thermal analysis or differential scanning calorimetry can be used to determine the thermal dissociation temperature from the temperature at which the heat absorption which accompanies the thermal dissociation reaction is observed. In order to ensure greater accuracy, a method that combines differential thermal analysis or differential scanning calorimetry with a thermogravimetric device may also be used. Furthermore, the thermal dissociation reaction of the urea linkage upon heating may also be followed by using a (near) infrared spectrophotometer or a Raman spectrophotometer or the like to quantify the amount of the urea linkage, and then deeming the temperature at which a reduction of 3%, or more preferably 5%, occurs relative to the initial amount as the thermal dissociation temperature.

[Reaction Conditions: When the Compound (A) is Produced Using Carbon Dioxide]

In the reaction for producing the compound (A) using the organic primary amine described above and carbon dioxide, first, the amino group of the organic primary amine and the carbon dioxide react to produce a carboxyamino group. Subsequently, the carboxyamino group and a separate amino group undergo a dehydration condensation, producing water and the compound (A) having a urea linkage.

Examples of methods that may be employed appropriately for reacting the organic primary amine and carbon dioxide include a method in which the organic primary amine is placed in a reaction vessel, and carbon dioxide is then introduced into the vessel, and a method in which a reaction vessel is filled with carbon dioxide, and the organic primary amine is then added to the vessel.

Further, carbon dioxide may be absorbed in advance by the organic primary amine introduced into the reaction vessel, for example, using a method in which the organic primary amine is exposed to a stream of carbon dioxide, or a method in which carbon dioxide is bubbled through the organic primary amine.

The carbon dioxide may be introduced into the reaction vessel using a device such as a pump, a compressor, or a blower.

The reaction temperature varies depending on the compound used, but is preferably a temperature lower than the thermal dissociation temperature of the urea linkage. For example, the reaction may be conducted at a temperature within a range from at least 80° C. to not more than 350° C., and is preferably at least 100° C. to not more than 300° C., and more preferably at least 120° C. to not more than 250° C. By ensuring that the reaction temperature is at least as high as the above lower limit, absorption of the carbon dioxide into the organic primary amine occurs more readily, the production reaction for the carboxyamino group proceeds more efficiently, and any lowering of the production reaction rate for the urea linkage from the carboxyamino group and amino group can be suppressed. On the other hand, by ensuring that the reaction temperature is not higher than the above upper limit, any deterioration in the absorption of the carbon dioxide into the organic primary amine can be prevented, slowing of the production reaction for the carboxyamino group can be prevented, and the production reaction rate for the urea linkage from the carboxyamino group and amino group can be increased. Furthermore, when setting the reaction temperature, the thermal stability of the compound being used must also be considered.

The pressure is preferably at least 0.1 MPa but not more than 20 MPa (absolute pressure), more preferably at least 0.5 MPa but not more than 15 MPa, and even more preferably at least 1 MPa but not more than 10 MPa. By ensuring that the pressure is at least as high as the above lower limit, the carbon dioxide concentration inside the reaction vessel can be prevented from becoming too dilute, thus preventing slowing of the production reaction for the carboxyamino group.

On the other hand, by ensuring that the pressure is not higher than the above upper limit, the reaction can be performed without using a large-scale reaction vessel. Further, by ensuring that the pressure is not higher than the above upper limit, corrosion by the carbon dioxide can be prevented in those cases where a reaction vessel made of a stainless steel material such as SUS316 or SUS304 is used.

The method used for controlling the pressure is preferably a method in which the reaction vessel is sealed and the pressure is controlled using the carbon dioxide, or a method in which the pressure is controlled using a backpressure valve while the carbon dioxide is passed through the reaction system.

In cases oriented toward the method in which the reaction vessel is sealed, the molar amount of carbon dioxide may be set within a stoichiometric ratio range from at least 0.5 times to not more than 500 times, and is preferably within a range from at least 0.6 times to not more than 400 times, more preferably at least 0.7 times to not more than 350 times, and even more preferably at least 1 times to not more than 300 times, relative to the molar amount of primary amino groups in the organic primary amine. By ensuring that the amount of carbon dioxide used is at least as large as the above lower limit, retention of unreacted amino groups can be more effectively prevented, whereas an amount not greater than the above upper limit is preferred, because for example, under conditions of constant pressure, the vapor phase volume can be reduced, enabling a reduction in the size of the reactor, whereas for example, under conditions of constant volume, the reaction pressure can be reduced, enabling the pressure-resistant performance required of the reactor to be reduced.

In those cases where the reaction is conducted while the carbon dioxide is passed through the reaction system, the molar amount of carbon dioxide relative to the organic primary amine becomes a large excess, meaning the reaction proceeds preferentially, and this configuration is therefore preferred.

The reaction is an equilibration reaction, and if the water generated upon production of the urea linkage is not removed from the reaction system, then at the point where a certain amount of the compound (A) has been produced, progression of the reaction appears to stop, and the desired yield of the compound (A) can often not be reached. Accordingly, in step (1), when producing the compound (A) using the organic primary amine and carbon dioxide, the reaction is preferably conducted while the water produced by the reaction between the organic primary amine and the carbon dioxide is extracted from the reaction system.

In step (1), the production reaction for the compound (A) is preferably conducted in the liquid phase, and it is more preferable that a solvent is used. Examples of the solvent include nitrile compounds, aromatic compounds substituted with a halogen or nitro group, polycyclic hydrocarbon compounds, aliphatic hydrocarbons, ketones, esters, ethers and thioethers, ester compounds, sulfoxides, aromatic hydroxy compounds, and aliphatic alcohols. Among these, aromatic hydroxy compounds are preferred. Examples of the nitrile compounds include acetonitrile and benzonitrile. Examples of the aromatic compounds substituted with a halogen or nitro group include chlorobenzene, dichlorobenzene, bromobenzene, dibromobenzene, chloronaphthalene, bromonaphthalene, nitrobenzene, and nitronaphthalene. Examples of the polycyclic hydrocarbon compounds include diphenyl, substituted diphenyl, diphenylmethane, terphenyl, anthracene, and dibenzyltoluene. Examples of the aliphatic hydrocarbons include cyclohexane, cyclopentane, cyclooctane, and ethylcyclohexane. Examples of the ketones include methyl ethyl ketone, acetophenone, acetone, and methyl ethyl ketone. The esters may be monoester compounds or diester compounds. Examples of the monoester compounds include ethyl acetate and ethyl benzoate. Examples of the diester compounds include dibutyl phthalate, dihexyl phthalate, dioctyl phthalate, and benzyl butyl phthalate. Examples of the ethers and thioethers include tetrahydrofuran, 1,4-dioxane, 1,2-dimethoxyethane, diphenyl ether, and diphenyl sulfide. Examples of the sulfoxides include dimethyl sulfoxide and diphenyl sulfoxide. Examples of the aromatic hydroxy compounds include phenol and dimethylphenol. Examples of the aliphatic alcohols include propanol and ethylene glycol. These solvents may be used individually, or a combination of two or more solvents may be used.

Further, in step (1), if necessary, a catalyst may be used for the purpose of increasing the reaction rate. Examples of the catalyst include phosphoric acid, phosphorous acid, hypophosphorous acid, as well as metal salts, ester derivatives, amides, and anhydrides of these acids. Examples of the metal salts include sodium salts, lithium salts and potassium salts. Examples of the ester derivatives include phenyl esters and alkyl esters. Examples of the amides include phosphoramidites. Examples of the anhydrides include pyrophosphoric acid and metaphosphoric acid. Additional examples of the catalyst include tertiary amines, phosphorus chlorides, phosphite derivatives, phosphine derivatives, arylboronic acids, and halides of group 4 metals. Examples of the tertiary amines include triethylamine, pyridine, and 4-dimethylaminopyridine. Examples of the phosphorus chlorides include phosphorus trichloride and the like. Examples of the phosphite derivatives include triaryl phosphites. Examples of the phosphine derivatives include triarylphosphines and triarylphosphine dihalides. Examples of the arylboronic acids include 3,5-bistrifluorophenylboronic acid and the like. Examples of the halides of group 4 metals include iron chloride and the like. These catalysts may be used individually, or a combination of two or more catalysts may be used.

Furthermore, in step (1), an end-capping agent may be used to control the amount of production of the compound (A) to the desired value.

Examples of the end-capping agent include monoamines, monocarboxylic acids, and carbonate esters. Examples of the monoamines include hexylamine, octylamine, cyclohexylamine and aniline. Examples of the monocarboxylic acids include acetic acid, lauric acid and benzoic acid. Examples of the carbonate esters include dimethyl carbonate and diphenyl carbonate. These end-capping agents may be used individually, or a combination of two or more end-capping agents may be used. There are no particular limitations on the amount added of the end-capping agent, and an amount that is appropriate for controlling the yield of the target compound and the amount of production of the urea linkage to achieve the desired values may be used.

The reaction time (the residence time in the case of a continuous reaction) differs depending on factors such as the composition of the reaction system, the reaction temperature, the reactor and the reaction pressure, but is typically at least 0.01 hours but not longer than 100 hours. The reaction time may also be determined based on the amount produced of the target compound. For example, the reaction liquid may be sampled and the amounts of the target compound and the urea linkage quantified, with the reaction then being stopped once confirmation is made that the desired yield relative to the amount of used organic primary amine has been reached.

[Reaction Conditions: When the Compound (A) is Produced Using a Carbonic Acid Derivative]

Although there are no particular limitations, the method for producing the compound (A) from the organic primary amine and a carbonic acid derivative is preferably a method (i) or method (ii) described below.

(i) A method for producing the compound (A) having a urea linkage by reacting the organic primary amine and the carbonic acid derivative "in a single stage".

(ii) A method including a step (ii-1) of obtaining a reaction mixture containing a compound having a ureido group by reacting the organic primary amine and a carbonic acid derivative, wherein the carbonic acid derivative is at least one of urea and an N-unsubstituted carbamate ester, and a step (ii-2) of producing the compound (A) having a urea linkage by conducting a condensation of the compound having a ureido group obtained in step (ii-1).

In the method (i) and the method (ii), a carbonate ester may also be used as the carbonic acid derivative, but from the viewpoint of reducing the amount of carbonate ester used, which is one object of the present embodiment, this is not necessarily recommended.

Further, at least one compound selected from among N-unsubstituted carbamate esters, N,N'-disubstituted ureas, N-substituted ureas and urea is preferred, and urea is more preferred.

(Method (i))

The expression "in a single stage" used in relation to the method (i) means that, unlike the method (ii), there is no division of the method into steps, and does not necessarily mean that the compound (A) is produced directly from the reaction of the organic primary amine and the carbonic acid derivative.

In the method (i), the compound (A) (the compound having a urea linkage) is produced, for example, by a reaction represented by general formula (Ib) shown below.

[Chemical formula 2]

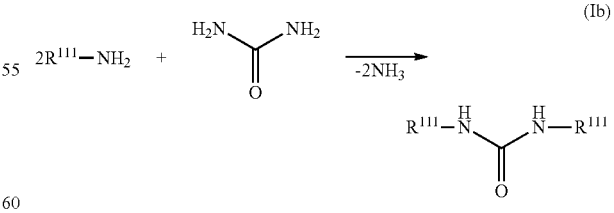

In general formula (Ib), $R^{111}$ represents a monovalent organic group. Examples of the organic group for $R^{111}$ include the same groups as those exemplified below as the monovalent organic group for $R^{251}$.

In the above general formula (Ib), in order to simplify the description, a single case is shown in which an organic primary amine having one primary amino group per molecule (namely, a monofunctional organic primary amine) is used, and urea is used as the carbonic acid derivative, but a person skilled in the art will readily comprehend that a similar reaction also occurs in cases where the organic primary amine used in the present embodiment is an organic primary amine having two or more primary amino groups per molecule (namely, a difunctional or higher organic primary amine), and cases where a compound other than urea is used as the carbonic acid derivative, such as cases where an N-alkyl urea or an N,N'-dialkyl urea in which each of the amino groups may be independently substituted with an alkyl group is used as the urea derivative. For example, in those cases where an N,N'-dialkyl urea is used, instead of the ammonia that is produced as a by-product in the above general formula (Ib), an alkylamine that corresponds with the alkyl group is produced as a by-product.

The reaction conditions for reacting the organic primary amine and the carbonic acid derivative differ depending on the compounds undergoing reaction, but examples of preferred ranges are described below.

The molar amount of the carbonic acid derivative, expressed as a stoichiometric ratio relative to the molar amount of primary amino groups in the organic primary amine, may be set within a range from at least 0.5 times to not more than 50 times, and is preferably within a range from at least 0.1 times to not more than 10 times, more preferably at least 0.2 times to not more than 5 times, and even more preferably at least 0.3 times to not more than 2 times. By ensuring that the amount used of the carbonic acid derivative is at least as large as the above lower limit, retention of unreacted amino groups can be more effectively prevented. On the other hand, by ensuring that amount used of the carbonic acid derivative is not greater than the above upper limit, the size of the reactor and the solubility of the carbonic acid derivative need not be considered, and any reduction in the amount produced of the target compound (A) can be effectively suppressed.

Further, the molar amount of the carbonic acid derivative may also be set to a stoichiometric ratio of less than 0.5 times relative to the molar amount of primary amino groups in the organic primary amine. By ensuring that the amount used of the carbonic acid derivative satisfies this range, the compound (A) having a urea linkage can be synthesized in a single stage with good stability and high yield.

The reaction temperature varies depending on the reactivity between the organic primary amine and the carbonic acid derivative that are used, but the temperature is preferably lower than the thermal dissociation temperature of the urea linkage. Specifically, the reaction temperature is preferably within a range from at least 50° C. to not more than 250° C., more preferably within a range from at least 80° C. to not more than 220° C., and even more preferably within a range from at least 100° C. to not more than 180° C. By ensuring that the reaction temperature is not higher than the above upper limit, the occurrence of decomposition of the carbonic acid derivative and decomposition reactions and modification reactions and the like of the product compound (A) can be more effectively suppressed. On the other hand, by ensuring that the reaction temperature is at least as high as the above lower limit, the reaction time can be effectively prevented from becoming too long, and a more suitable yield of the target compound (A) can be achieved.

The reaction pressure differs depending on factors such as the composition of the reaction system, the reaction temperature, the method used for removing by-products (such as ammonia) and the reactor, and may be a reduced pressure, normal pressure or pressurization, but is typically set within a range from at least 0.01 kPa to not more than 10 MPa (absolute pressure), and if consideration is given to the ease of industrial implementation, then a reduced pressure or normal pressure is preferred, and a pressure within a range from at least 0.1 kPa to not more than 1 MPa (absolute pressure) is more preferred.

There are no particular limitations on the reactor used in the method (i), and a conventional reactor may be used, but at least one of a tank reactor or a tower reactor fitted with a condenser can be used particularly favorably. Specific examples include a stirred tank, pressurized stirred tank, reduced-pressure stirred tank, tower reactor, distillation tower, packed tower and thin-film distillation apparatus, and suitable combinations of these conventionally known reactors may also be used.

There are no particular limitations on the material of the reactor and the condenser, and conventional materials may be used. For example, materials such as glass, stainless steel, carbon steel, Hastelloy, substrates with a glass lining, and materials coated with Teflon (a registered trademark) may be used. Among these, SUS304, SUS316, and SUS316L and the like are inexpensive, and can be used favorably. If necessary, measuring equipment such as a flow rate meter or thermometer, or other conventional processing devices such as a reboiler, pump or condenser may also be added. Further, heating may be performed using conventional methods such as steam or a heater, and cooling may also employ conventional methods such as natural cooling, cooling water or brine. If necessary, various additional steps may be added.

In the reaction between the organic primary amine and the carbonic acid derivative, by-products are often produced, such as ammonia in the case where urea is used as the carbonic acid derivative, ammonia and an alkylamine corresponding with the substituent alkyl group in the case where an N-substituted alkyl urea is used as the carbonic acid derivative, an alkylamine corresponding with the substituent alkyl group in the case where an N,N'-substituted dialkyl urea is used, or a hydroxy compound and ammonia in the case where an N-unsubstituted carbamate ester is used. This ammonia, alkylamine and hydroxy compound may be removed from the system while the reaction proceeds. Examples of the method used for removing these compounds from the system include reactive distillation methods, methods that employ an inert gas, and methods that employ membrane separation or adsorption separation. A reactive distillation method is a method in which reaction is conducted in a boiling solvent or the like while the ammonia, alkylamine or hydroxy compound or the like is removed. Further, a method that employs an inert gas is a method in which the ammonia, alkylamine or hydroxy compound or the like that is generated successively during the reaction is carried along in the gas phase by the inert gas and separated from the reaction system. Either a single gas or a mixture of two or more gases such as nitrogen, helium, argon, carbon dioxide gas, methane, ethane or propane may be used as the inert gas, with this inert gas being introduced into the reaction system. Examples of the adsorbent used in the adsorption separation method include adsorbents that can be used under the temperature conditions at which the reaction is conducted, such as silica, alumina, various zeolites, and diatomaceous earth and the like. One of these methods may be implemented alone, or a combination of a plurality of methods may be implemented.

The reaction time (the residence time in the case of a continuous reaction) differs depending on factors such as the composition of the reaction system, the reaction temperature, the reactor and the reaction pressure, but is typically at least 0.01 hours but not longer than 100 hours. The reaction time may also be determined based on the amount produced of the target compound. For example, the reaction liquid may be sampled and the amounts of the target compound and the urea linkage quantified, with the reaction then being stopped once confirmation is made that the desired yield relative to the amount of used organic primary amine has been reached.

(Method (ii))

The method (ii) is a method that includes step (ii-1) and step (ii-2) described below, and is a method for reacting the organic primary amine and the carbonic acid derivative.

(ii-1) A step of obtaining a reaction mixture containing a compound having a ureido group by reacting the organic primary amine and the carbonic acid derivative.

(ii-2) A step of producing the compound (A) by conducting a condensation of the compound having a ureido group obtained in step (ii-1).

Step (ii-1) is described below in detail.

In step (ii-1), the carbonic acid derivative is at least one of urea, an N-alkyl urea or N,N'-dialkyl urea in which each of the amino groups of urea may be independently substituted with an alkyl group, or an N-unsubstituted carbamate ester, and this carbonic acid derivative is reacted with the organic primary amine to obtain a reaction mixture containing a compound having a ureido group.

The compound (A) may sometimes also be produced in step (ii-1), and any compound (A) obtained in step (ii-1) may also be used as the compound (A) used in the subsequent step (2).

The reaction conditions for conducting the reaction between the organic primary amine and the carbonic acid derivative differ depending on the compounds undergoing reaction, but the molar amount of the carbonic acid derivative relative to the molar amount of primary amino groups in the organic primary amine may be set within a range from at least 0.5 times to not more than 100 times, and is preferably within a range from at least 1 times to not more than 50 times, more preferably within a range from at least 1.2 times to not more than 10 times, and more preferably within a range from at least 1.5 times to not more than 5 times. By ensuring that the amount used of the carbonic acid derivative is at least as large as the above lower limit, retention of unreacted amino groups can be more effectively prevented. On the other hand, by ensuring that amount used of the carbonic acid derivative is not greater than the above upper limit, the size of the reactor and the solubility of the carbonic acid derivative need not be considered, and any reduction in the amount produced of the target compound (A) can be effectively suppressed.

Further, the molar amount of the carbonic acid derivative may also be set to a value of less than 0.5 times the molar amount of primary amino groups in the organic primary amine. By ensuring that the amount used of the carbonic acid derivative satisfies this range, the compound (A) can be synthesized with good stability and high yield.

The reaction temperature varies depending on the reactivity between the organic primary amine and the carbonic acid derivative that are used, but the temperature is preferably lower than the thermal dissociation temperature of the urea linkage. Specifically, the reaction temperature is preferably within a range from at least 50° C. to not more than 200° C., more preferably within a range from at least 80° C. to not more than 190° C., and even more preferably within a range from at least 100° C. to not more than 180° C. By ensuring that the reaction temperature is not higher than the above upper limit, the occurrence of decomposition of the carbonic acid derivative and decomposition reactions and modification reactions and the like of the product compound (A) can be more effectively suppressed. On the other hand, by ensuring that the reaction temperature is at least as high as the above lower limit, the reaction time can be effectively prevented from becoming too long, and a more suitable yield of the target compound (A) can be achieved.

The reaction pressure differs depending on factors such as the composition of the reaction system, the reaction temperature, the method used for removing by-products (such as ammonia) and the reactor, and may be a reduced pressure, normal pressure or pressurization, but is typically set within a range from at least 0.01 kPa to not more than 10 MPa (absolute pressure), and if consideration is given to the ease of industrial implementation, then a reduced pressure or normal pressure is preferred, and a pressure within a range from at least 0.1 kPa to not more than 1 MPa (absolute pressure) is more preferred.

There are no particular limitations on the reactor used in step (ii-1) or the material of the reactor, and examples include the same reactors and materials as those exemplified above for the method (i). Conventional materials and reactors may be used.

In the reaction between the organic primary amine and the carbonic acid derivative, by-products are often produced, such as ammonia in the case where urea is used as the carbonic acid derivative, an alkylamine corresponding with the substituent alkyl group in the case where an N-substituted alkyl urea is used, or a hydroxy compound in the case where an N-unsubstituted carbamate ester is used as the carbonic acid derivative. This ammonia or hydroxy compound or the like may be removed from the system while the reaction proceeds. The removal method may employ the same methods as those exemplified above for the method (i).

Further, in step (ii-1), water may also be used as the solvent.

The reaction time (the residence time in the case of a continuous reaction) differs depending on factors such as the composition of the reaction system, the reaction temperature, the reactor and the reaction pressure, but is typically at least 0.01 hours but not longer than 100 hours. The reaction time may also be determined based on the amount produced of the target compound. For example, the reaction liquid may be sampled and the amounts of the target compound and the urea linkage quantified, with the reaction then being stopped once confirmation is made that the desired yield relative to the amount of used organic primary amine has been reached.

In step (ii-1), a compound having a ureido group is produced via the reaction represented by general formula (Ic) shown below, and a condensate of the compound having a ureido group, and the compound (A) (compound having a urea linkage) as a reaction product of the organic primary amine and the compound having a ureido group are also produced (for example, see general formulas (Id) and (Ie) shown below).

[Chemical formula 3]

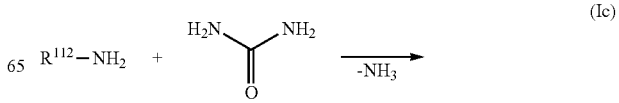

(Ic)

-continued

[Chemical formula 4]

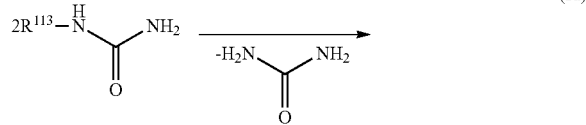

(Id)

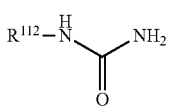

[Chemical formula 5]

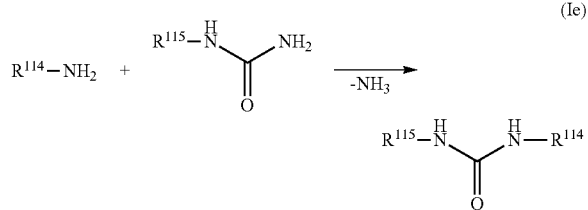

(Ie)

In general formulas (Ic) to (Ie), each of $R^{112}$, $R^{113}$, $R^{114}$ and $R^{115}$ independently represents a monovalent organic group. Examples of the monovalent organic group for $R^{112}$, $R^{113}$, $R^{114}$ and $R^{115}$ include the same groups as those exemplified below as the monovalent organic group for $R^{251}$.

In the above general formulas (Id) and (Ie), in order to simplify the description, a single case is shown in which an organic primary amine having one primary amino group per molecule (namely, a monofunctional organic primary amine) is used, and urea is used as the carbonic acid derivative, but a person skilled in the art will readily comprehend that similar reactions will also occur in cases where the organic primary amine used in the present embodiment is an organic primary amine having two or more primary amino groups per molecule (namely, a difunctional or higher organic primary amine), and cases where a compound other than urea is used as the carbonic acid derivative, such as cases where an N-alkyl urea in which an amino group of urea has been substituted with an alkyl group is used as the urea derivative. For example, in those cases where an N-dialkyl urea is used, instead of the ammonia that is produced as a by-product in the above general formula (Id), an alkylamine that corresponds with the alkyl group is produced as a by-product.

Subsequently, in step (ii-2), the compound having a ureido group obtained in step (ii-1) is subjected to a condensation to produce the compound (A) having a urea linkage. In other words, for example, the reaction represented by the above general formula (Id) occurs.

The reaction mixture containing the compound having an ureido group obtained in step (ii-1) may be used without modification in step (ii-2), or prior to performing step (ii-2), a step for separating and collecting the compound having an ureido group may be provided, and another step for purifying the separated and collected compound having an ureido group may also be provided. In those cases where a reaction catalyst is used in step (ii-1), the reaction catalyst may be removed from the reaction mixture of step (ii-1) prior to performing step (ii-2), or step (ii-2) may be simply performed without removing the catalyst.

The reaction temperature varies depending on the reactivity between the organic primary amine and the carbonic acid derivative that are used, but the temperature is preferably within a range from at least 100° C. to not more than 200° C., more preferably within a range from at least 110° C. to not more than 190° C., and even more preferably within a range from at least 120° C. to not more than 180° C. By ensuring that the reaction temperature is not higher than the above upper limit, the occurrence of decomposition reactions and modification reactions and the like of the product compound (A) can be more effectively suppressed. On the other hand, by ensuring that the reaction temperature is at least as high as the above lower limit, the reaction time can be effectively prevented from becoming too long, and a more suitable yield of the target compound (A) can be achieved.

The reaction pressure differs depending on factors such as the composition of the reaction system, the reaction temperature, the method used for removing by-products (such as ammonia) and the reactor, and may be a reduced pressure, normal pressure or pressurization, but is typically set within a range from at least 0.01 kPa to not more than 10 MPa (absolute pressure), and if consideration is given to the ease of industrial implementation, then a reduced pressure or normal pressure is preferred, and a pressure within a range from at least 0.1 kPa to not more than 1 MPa (absolute pressure) is more preferred.

There are no particular limitations on the reactor used in step (ii-2) or the material of the reactor, and examples include the same reactors and materials as those exemplified above for the method (i). Conventional materials and reactors may be used.

In the condensation reaction of the compound having a ureido group in step (ii-2), urea is often produced as a by-product. This urea may be removed from the reaction system while the reaction proceeds. Examples of the method used for removing the urea from the system include reactive distillation methods and methods that employ an inert gas. A reactive distillation method is a method in which the reaction is conducted in a boiling solvent or the like while the urea or the like is removed. Further, a method that employs an inert gas is a method in which the urea or the like that is generated successively during the reaction is carried along in the gas phase by the inert gas and separated from the reaction system. Either a single gas or a mixture of two or more gases such as nitrogen, helium, argon, carbon dioxide gas, methane, ethane or propane may be used as the inert gas, with this inert gas being introduced into the reaction system.

In those cases where a catalyst is used in step (ii-1), and the reaction mixture obtained in step (ii-1) is used without modification in step (ii-2), additional catalyst may or may not be added.

The reaction time (the residence time in the case of a continuous reaction) differs depending on factors such as the composition of the reaction system, the reaction temperature, the reactor and the reaction pressure, but is typically at least 0.01 hours but not longer than 100 hours. The reaction time may also be determined based on the amount produced of the target compound. For example, the reaction liquid may be sampled and the amounts of the target compound and the urea linkage quantified, with the reaction then being stopped once confirmation is made that the desired yield relative to the amounts used of the organic primary amine and the compound having a ureido group have been reached.

<Step (2)>

In step (2), the compound (A) and a carbonate ester are reacted to produce a carbamate.

[Reaction Conditions]

The reaction temperature in step (2) is preferably at least 50° C. but not more than 250° C., more preferably at least 80° C. but not more than 220° C., and even more preferably at least 100° C. but not more than 200° C. By ensuring that the reaction temperature is at least as high as the above lower limit, a low thermal dissociation reaction rate and reduced reaction efficiency can be more effectively suppressed. On the other hand, by ensuring that the reaction temperature is not higher than the above upper limit, the thermal dissociation reaction of the urea linkage of the compound (A), and modification reactions of the resulting isocyanate and amino groups, can be more effectively prevented.

The amount used of the carbonate ester varies depending on the type of carbonate ester used and the reaction conditions, but relative to the number of urea linkages in the compound (A), the number of carbonate ester molecules is preferably not more than 10, more preferably not more than 3, and even more preferably 2 or less. By ensuring that the number of carbonate ester molecules is not more than the above upper limit, the reaction rate can be increased, and the occurrence of side reactions such as N-alkylation can be more effectively prevented, while maintaining favorable reaction efficiency.

The reaction in step (2) is preferably conducted in the presence of a solvent. The solvent may be any compound that is capable of dissolving the compound (A) and the carbonate ester, and is stable within the reaction temperature range described above. Examples of the solvent include the same solvents as those exemplified above in relation to step (1).

Further, in the reaction of step (2), for example, a catalyst may be used for the purpose of increasing the reaction rate. Examples of the catalyst include the same catalysts as those exemplified above in relation to step (1).

Furthermore, the reaction in step (2) may be conducted under pressurized conditions, normal pressure, or reduced-pressure conditions. Further, the reaction in step (2) is preferably conducted under an atmosphere of an inert gas such as nitrogen, argon, helium or neon.

Examples of the reactor include a stirred tank, pressurized stirred tank, reduced-pressure stirred tank, tower reactor, distillation tower, packed tower or thin-film distillation apparatus, and suitable combinations of these conventionally known reactors may also be used. In order to keep the reaction temperature constant, at least one of a conventional cooling device or heating device may be fitted to the reactor. Further, there are no particular limitations on the material of the reactor, and conventional materials may be used. For example, materials such as glass, stainless steel, carbon steel, Hastelloy, substrates with a glass lining, and materials coated with Teflon (a registered trademark) may be used.

The reaction time (the residence time in the case of a continuous reaction) differs depending on factors such as the composition of the reaction system, the reaction temperature, the reactor and the reaction pressure, but is typically at least 0.01 hours but not longer than 100 hours. The reaction time may also be determined based on the amount produced of the target compound. For example, the reaction liquid may be sampled and the amount of the target compound quantified, with the reaction then being stopped once confirmation is made that the desired yield relative to the amounts used of the carbonate ester and the compound (A) or the urea linkage has been reached.

<Step (Y)>

The method for producing a carbamate according to the present embodiment can produce a carbamate using a method that includes the step (1) and the step (2) described above. On the other hand, in the method for producing a carbamate according to an embodiment of the present invention, in the case where an organic primary amine having a carboxy group, such as at least one of an amino acid or a salt of an amino acid, is used as the organic primary amine, it is preferable that the method also includes a step (Y) described below, either before the step (1), or after the step (1) but before the step (2):

(Y) a step of esterifying the carboxy group of the organic primary amine, or esterifying the carboxy group of the compound (A) obtained in the step (1).

Examples of compounds that can react with either the carboxy group of the organic primary amine or the carboxy group of the compound (A) obtained in step (1) described above to form an ester linkage include compounds having an alcoholic hydroxy group. In this case, the step (Y) proceeds via a reaction represented by general formula (If) shown below.

[Chemical formula 6]

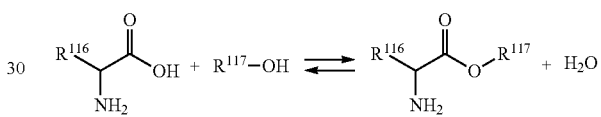

(If)

In general formula (If), each of $R^{116}$ and $R^{117}$ independently represents a monovalent organic group. Examples of the organic groups for $R^{116}$ and $R^{117}$ include the same groups as those exemplified below as the monovalent organic group for $R^{251}$.

Further, in those cases where the amino acid group ($—C(NH_2)COOH$) shown in the first item on the left side of general formula (If) has formed a salt with an acid, or in those cases where the amino acid has formed a salt with a base, the reaction proceeds in a similar manner. Further, in those cases where $R^{91}$ or $R^{92}$ contains an amino group ($—NH^2$), that amino group may also form a salt with an acid.

Furthermore, in general formula (If), in order to simplify the description, the case in which the esterification reaction uses an amino acid is shown, but a person skilled in the art will readily comprehend that a similar reaction will also occur in the case where the compound (A) obtained in step (1) is used.

The amount used of the compound having an alcoholic hydroxy group, expressed as a stoichiometric ratio (molar ratio) relative to the amount of amino acid residues, is preferably at least 0.5 times but not more than 10 times, more preferably at least 1 times but not more than 5 times, and even more preferably at least 1.2 times but not more than 3 times.

The reaction temperature is preferably at least 30° C. but not more than 200° C., more preferably at least 50° C. but not more than 180° C., and even more preferably at least 70° C. but not more than 150° C.

The reaction in step (Y) may be conducted in the presence of a solvent. The solvent may be any compound that is capable of dissolving the reactants (the compound (A) and the compound having an alcoholic hydroxy group and the like), and is stable within the reaction temperature range described above, with examples of the solvent including the same solvents as those exemplified above in relation to step (1).

Further, in the reaction of step (Y), a catalyst may be used for the purpose of increasing the reaction rate. Examples of catalysts that can be used favorably include inorganic acids such as hydrochloric acid, nitric acid, phosphoric acid and sulfuric acid. These inorganic acids will often form salts with an amino group contained within at least one of the compound (A) obtained in step (1) and the compound having an alcoholic hydroxy group that represent the raw materials in step (Y), or with an amino group contained in the amino acid ester that represents the product of step (Y), and therefore the amount of these inorganic acids used as a catalyst is preferably greater than the amount required to form these salts. Furthermore, in those cases where conditions such as a high temperature or reduced pressure are employed in step (Y), the acid that forms the above salts and the acid used as a catalyst may sometimes undergo distillation and be lost from the reaction system. Accordingly, the reaction is preferably conducted while sufficient acid is added to ensure satisfactory progression of the reaction.

The reaction (esterification reaction) represented by the above general formula (If) is an equilibration reaction that is accompanied by the production of water, and therefore the reaction is preferably conducted while the produced water is extracted from the system. Accordingly, the esterification reaction may be conducted under pressurized conditions, normal pressure or reduced-pressure conditions, but is preferably conducted under normal pressure or reduced-pressure conditions.

Further, the reaction in step (Y) is preferably conducted under an atmosphere of an inert gas such as nitrogen, argon, helium or neon.

Examples of the reactor include a stirred tank, pressurized stirred tank, reduced-pressure stirred tank, tower reactor, distillation tower, packed tower or thin-film distillation apparatus, and suitable combinations of these conventionally known reactors may also be used. In order to keep the reaction temperature constant, at least one of a conventional cooling device or heating device may be fitted to the reactor. Further, there are no particular limitations on the material of the reactor, and conventional materials may be used. For example, materials such as glass, stainless steel, carbon steel, Hastelloy, substrates with a glass lining, and materials coated with Teflon (a registered trademark) may be used.

The reaction time (the residence time in the case of a continuous reaction) differs depending on factors such as the composition of the reaction system, the reaction temperature, the reactor and the reaction pressure, but is typically at least 0.01 hours but not longer than 100 hours. The reaction time may also be determined based on the amount produced of the target compound. For example, the reaction liquid may be sampled and the amount of the target compound quantified, with the reaction then being stopped once confirmation is made that the desired yield has been reached.

<Raw Materials and Products>

Next, the raw materials used and the product from the production method of the present embodiment are described below in further detail.

[Organic Primary Amine] 1) Amine Compound (II)

The organic primary amine used in step (1) may be any compound having at least one primary amino group per molecule, but of the various possibilities, is preferably an amine compound represented by general formula (II) shown below (hereafter sometimes referred to as "the amine compound (II)").

[Chemical formula 7]

(II)

In general formula (II), n21 represents an integer of 1 or greater. $R^{21}$ represents an n21-valent organic group.

($R^{21}$)

In general formula (II), $R^{21}$ is preferably an organic group of at least 3 but not more than 85 carbon atoms, and is more preferably an organic group of at least 3 but not more than 30 carbon atoms.

Examples of the organic group for $R^{21}$ include aliphatic hydrocarbon groups, aromatic hydrocarbon groups, and groups composed of an aliphatic hydrocarbon group and an aromatic hydrocarbon group bonded together. Specific examples of $R^{21}$ include cyclic hydrocarbon groups, acyclic hydrocarbon groups, groups in which at least one cyclic group is bonded to an acyclic hydrocarbon group, and groups in which these groups are covalently bonded to a specific non-metal atom. Examples of the cyclic group include cyclic hydrocarbon groups, heterocyclic groups, heterocyclic spiro groups, and hetero crosslinked cyclic groups. Examples of the cyclic hydrocarbon groups include monocyclic hydrocarbon groups, condensed polycyclic hydrocarbon groups, crosslinked cyclic hydrocarbon groups, spiro hydrocarbon groups, ring-aggregated hydrocarbon groups, and cyclic hydrocarbon groups having a side chain. Examples of the non-metal atom include carbon, oxygen, nitrogen, sulfur and silicon.

Further, the expression "covalently bonded to a specific non-metal atom" describes a state in which, for example, a group exemplified above is covalently bonded to a group represented by any one of formulas ((II)-1a) to ((II)-1m) shown below.

[Chemical formula 8]

((II)-1a)

((II)-1b)

((II)-1c)

((II)-1d)

((II)-1e)

((II)-1f)

((II)-1g)

((II)-1h)

-continued

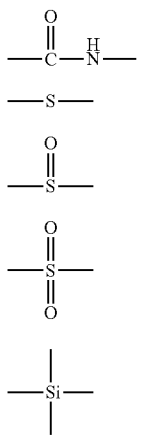

(n21)

In general formula (II), if consideration is given to the ease of production and the ease of handling, then n21 is preferably an integer of at least 1 but not more than 5, is more preferably 2 or 3, and is more preferably 3.

In the amine compound (11), in the case of a difunctional amine in which n21 is 2 (namely, a compound having two primary amino groups per molecule), examples of preferred amine compounds (11) include aliphatic diamines of at least 4 but not more than 30 carbon atoms, alicyclic diamines of at least 8 but not more than 30 carbon atoms, and diamines containing an aromatic group of at least 8 but not more than 30 carbon atoms.

Specific examples of the aliphatic diamines of at least 4 but not more than 30 carbon atoms include 1,4-tetramethylenediamine, 1,5-pentamethylenediamine, 1,4-diamino-2methylbutane, 1,6-hexamethylendiamine, 1,6-diamino-2,5-dimethylhexane, 2,2,4-trimethyl-1,6-hexainethylendiamine, lysine methyl ester diamine, and lysine ethyl ester diamine.

Specific examples of the alicyclic diamines of at least 8 but not more than 30 carbon atoms include isophoronediamine, 1,3-bis(aminomethyl)-cyclohexane, 4,4'-dicyclohexylmethandiamine, hydrogenated tetramethylxylylenediamine, and norbornenediamine.

Specific examples of the diamines containing an aromatic group of at least 8 but not more than 30 carbon atoms include 4,4'-diphenylmethanediamine, 2,6-tolylenediamine, xylylenediamine, tetramethylxylylenediamine, and naphthalenediamine.

In those cases where structural isomers exist for any of the above compounds, those structural isomers are also included within the examples of preferred amine compounds (II).

These compounds are merely examples of preferred amine compounds (II), and the preferred amine compounds (II) are not limited to the compounds listed above.

Further, compounds obtained by trimerizing three molecules of one of the above difunctional amines via an isocyanurate ring structure or a biuret linkage or the like may also be used as a trifunctional amine.

1-1) Amine Compound (II-1)

In the amine compound (II), in the case of a trifunctional amine in which n21 is 3 (namely, a compound having three primary amino groups per molecule), examples of preferred amine compounds (II) include amine compounds represented by general formula (II-1) shown below (hereafter sometimes referred to as "the amine compound (II-1)").

These compounds are merely examples of preferred amine compounds (II), and the preferred amine compounds (II) are not limited to these compounds.

[Chemical formula 9]

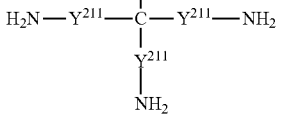

(II-1)

In general formula (II-1), each of the plurality of $Y^{211}$ groups independently represents a single bond or a divalent hydrocarbon group of at least 1 but not more than 20 carbon atoms which may include at least one group selected from the group consisting of an ester group and an ether group. The plurality of $Y^{211}$ groups may be the same or different. $R^{211}$ represents a hydrogen atom or a monovalent hydrocarbon group of at least 1 but not more than 12 carbon atoms.

($R^{211}$)

In general formula (II-1), $R^{211}$ is preferably an aliphatic hydrocarbon group of at least 1 but not more than 10 carbon atoms, or an aromatic hydrocarbon group of at least 6 but not more than 10 carbon atoms. Specific examples of the aliphatic hydrocarbon group of at least 1 but not more than 10 carbon atoms for $R^{211}$ include a methyl group, ethyl group, propyl group, butyl group, pentyl group, hexyl group and decyl group. Specific examples of the aromatic hydrocarbon group of at least 6 but not more than 10 carbon atoms for $R^{211}$ include a phenyl group, methylphenyl group, ethylphenyl group, butylphenyl group, dimethylphenyl group and diethylphenyl group.

($Y^{211}$)

In general formula (II-1), examples of preferred groups for $Y^{211}$ include divalent aliphatic hydrocarbon groups of at least 1 but not more than 20 carbon atoms, divalent aromatic hydrocarbon groups of at least 6 but not more than 20 carbon atoms, divalent groups of at least 2 but not more than 20 carbon atoms composed of an aliphatic hydrocarbon group and another aliphatic hydrocarbon group bonded together via an ester linkage, divalent groups of at least 2 but not more than 20 carbon atoms composed of an aliphatic hydrocarbon group and another aliphatic hydrocarbon group bonded together via an ether linkage, divalent groups of at least 7 but not more than 20 carbon atoms composed of an aliphatic hydrocarbon group and an aromatic hydrocarbon group bonded together via an ester linkage, divalent groups of at least 7 but not more than 20 carbon atoms composed of an aliphatic hydrocarbon group and an aromatic hydrocarbon group bonded together via an ether linkage, divalent groups of at least 14 but not more than 20 carbon atoms composed of an aromatic hydrocarbon group and another aromatic hydrocarbon group bonded together via an ester linkage, and divalent groups of at least 14 but not more than 20 carbon atoms composed of an aromatic hydrocarbon group and another aromatic hydrocarbon group bonded together via an ether linkage.

Examples of preferred amine compounds (II-1) include compounds in which $Y^{211}$ is a divalent aliphatic hydrocarbon groups of at least 1 but not more than 20 carbon atoms, compounds in which $Y^{211}$ is a divalent aromatic hydrocarbon groups of at least 6 but not more than 20 carbon atoms, compounds represented by general formula (II-1-1) shown below (hereafter sometimes referred to as "the compound (II-1-1)"), compounds represented by general formula (II-1-2) shown below (hereafter sometimes referred to as "the compound (II-1-2)"), and compounds represented by general formula (II-1-3) shown below.

Specific examples of the compounds in which $Y^{211}$ is a divalent aliphatic hydrocarbon groups of at least 1 but not more than 20 carbon atoms include 1,8-diamino-4-aminomethyloctane, 1,3,6-triaminohexane, 1,8-diamino-4-(aminomethyl)-2,4,7-trimethyloctane, 1,5-diamino-3-(aminomethyl)pentane, 1,6,11-triaminoundecane, 1,4,7-triaminoheptane, 1,2,2-triaminobutane, 1,2,6-triaminohexane, 1-amino-2,2-bis(aminomethyl)butane, 1,3,5-triaminocyclohexane, 1,7-diamino-4-(3-aminopropyl)heptane, and 1,3-diamino-2-(aminomethyl)-2-methylpropane.

Specific examples of the compounds in which $Y^{211}$ is a divalent aromatic hydrocarbon groups of at least 6 but not more than 20 carbon atoms include 1,3,5-triaminobenzene, 1,3,5-triamino-2-methylbenzene, 1,3,5-tris(1-aminopropan-2-yl)benzene, 1,3,5-tris(1-aminopropan-2-yl)-2-methylbenzene, 1,3,5-tris(1-aminomethyl)-2-methylbenzene, and 2,2'-((2-amino-1,3-phenylene)bis(methylene))bis(aminobenzene).

[Chemical formula 10]

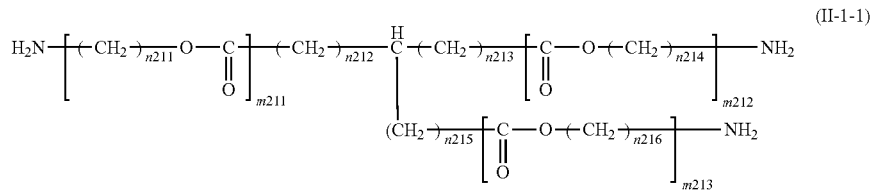

(II-1-1)

In general formula (II-1-1), each of m211, m212 and m213 independently represents 0 or 1. Each of n211, n214 and n216 independently represents an integer of at least 1 but not more than 4. Each of n212, n213 and n215 independently represents an integer of at least 0 but not more than 5.

[Chemical formula 11]

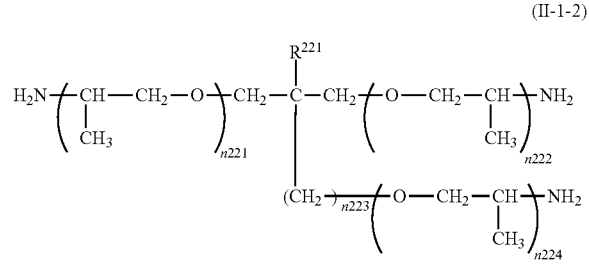

(II-1-2)

In general formula (II-1-2), $R^{221}$ represents a monovalent hydrocarbon group of at least 1 but not more than 4 carbon atoms. Each of n221, n222 and n224 independently represents an integer of at least 1 but not more than 6. The sum of n221, n222 and n224 is at least 3 but not more than 18. Further, n223 is an integer of at least 0 but not more than 3.

[Chemical formula 12]

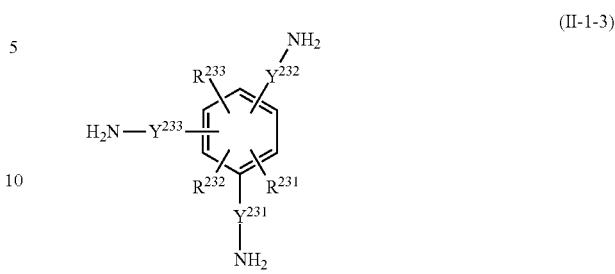

(II-1-3)

In general formula (II-1-3), each of $R^{231}$, $R^{232}$ and $R^{233}$ independently represents a hydrogen atom or a monovalent hydrocarbon group of at least 1 but not more than 12 carbon atoms. Each of $Y^{231}$, $Y^{232}$ and $Y^{233}$ independently represents a single bond or a divalent hydrocarbon group of at least 1 but not more than 20 carbon atoms which may include at least one group selected from the group consisting of an ester group and an ether group.

1-1-1) Compound (II-1-1)

The compound (II-1-1) is a compound represented by general formula (II-1-1) shown above.

(m211, m212 and m213)

In general formula (II-1-1), each of m211, m212 and m213 independently represents 0 or 1. Among the various possibilities, it is preferable that m211 and m213 are 0, and m212 is 1.

(n211, n212, n213, n214, n215 and n216)

Each of n211, n214 and n216 independently represents an integer of at least 1 but not more than 4. When m211, m212 and m213 are 0, n211, n214 and n216 do not exist. Among the various possibilities, it is preferable that n211 and n216 do not exist (meaning m211 and m213 are 0), and n214 is an integer of at least 2 but not more than 4.

Each of n212, n213 and n215 independently represents an integer of at least 0 but not more than 5. Among the various possibilities, it is preferable that n212 is an integer of at least 1 but not more than 4, and n213 and n215 are 0, and it is more preferable that n212 is an integer of at least 3 but not more than 4, and n213 and n215 are 0.

Examples of preferred compounds (II-1-1) include 1,2,3-propanetriamine (in general formula (II-1-1), m211=m212=m213=0, n212=n213=1, n215=0), tris(2-aminoethyl)amine (in general formula (II-1-1), m211=m212=m213=0, n212=n213=n215=2), 1,6,11-triaminoundecane (in general formula (II-1-1), m211=m212=m213=0, n212=n213=5, n215=0), 1,3,6-hexamethylenetriamine (in general formula (II-1-1), m211=m212=m213=0, n212=3, n213=2, n215=0), 1,8-diamino-4-(aminomethyl)octane (in general formula (II-1-1), m211=m212=m213=0, n212=4, n213=1, n215=3), 2-aminoethyl-2,5-diaminopentanoate (in general formula (II-1-1), m211=m213=0, m212=1, n212=3, n213=n215=0, n214=2), bis(2-aminoethyl)-2-aminobutanedioate (in general formula (II-1-1), m211=m212=1, m213=0, n211=n214=2, n212=1, n213=n215=0), bis(2-aminoethyl)-2-aminopentanedioate (in general formula (II-1-1), m211=m212=1, m213=0, n211=n214=2, n212=2, n213=n215=0), tris(2-aminoethyl) hexane-1,3,6-tricarboxylate (in general formula (II-1-1), m211=m212=m213=1, n211=n214=n216=2, n212=3, n213=2, n215=0), and aliphatic amines represented by general formula (II-1-1-1) shown below (hereafter sometimes referred to as "the aliphatic amine (II-1-1-1)") (in general formula (II-1-1), m211=m213=0, m212=1, n212=4, n213=n215=0). Among these, the aliphatic amine (II-1-1-1) is preferred as the compound (II-1-1).

[Chemical formula 13]

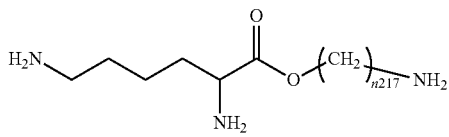

(II-1-1-1)

In general formula (II-1-1-1), n217 represents an integer of at least 2 but not more than 4.

1-1-1-1) Aliphatic Amine (II-1-1-1)

The aliphatic amine (II-1-1-1) is a compound represented by the above general formula (II-1-1-1).

(n217)

In general formula (II-1-1-1), n217 represents an integer of at least 2 but not more than 4, and is preferably either 1 or 2, and more preferably 2. In other words $(CH_2)_{n217}$ is an alkylene group of at least 2 but not more than 4 carbon atoms, and is preferably a linear or branched alkylene group of at least 2 but not more than 4 carbon atoms. Examples of this type of alkylene group include an ethylene group, propylene group, butylene group and isobutylene group, and among these, an ethylene group is preferred.

Examples of preferred aliphatic amines (II-1-1-1) include 2-aminoethyl-2,6-diaminohexanoate (wherein n217=2 in general formula (II-1-1-1)) and the like.

1-1-2) Compound (II-1-2)

The compound (II-1-2) is a compound represented by general formula (II-1-2) shown above.

($R^{221}$)

In general formula (II-1-2), $R^{221}$ represents a monovalent hydrocarbon group of at least 1 but not more than 4 carbon atoms, wherein the hydrocarbon group may be chain-like or cyclic, but is preferably chain-like. When the hydrocarbon group is chain-like, the group may be linear or branched. Examples of this type of $R^{221}$ group include a methyl group, ethyl group, n-propyl group, isopropyl group, n-butyl group, sec-butyl group, isobutyl group and tert-butyl group. Among these, $R^{22}$ is preferably a methyl group, ethyl group or isopropyl group.

(n221, n222, n223 and n224)

Each of n221, n222 and n224 independently represents an integer of at least 1 but not more than 6, and the sum of n221, n222 and n224 is at least 3 but not more than 18. Further, n223 is an integer of at least 0 but not more than 3. Among the various possibilities, it is preferable that n221, n222 and n224 are 1, and n223 is 0 or 1.

Examples of preferred compounds (II-1-2) include the compounds represented by formula (II-1-2-1) shown below.

[Chemical formula 14]

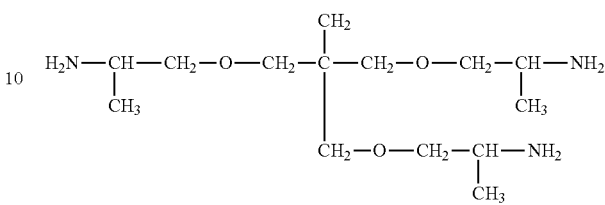

(II-1-2-1)

1-1-3) Compound (II-1-3)

The compound (II-1-3) is a compound represented by general formula (II-1-3) shown above.

($R^{231}$, $R^{232}$ and $R^{233}$)

In general formula (II-1-3), each of $R^{231}$, $R^{232}$ and $R^{233}$ independently represents a hydrogen atom or a monovalent hydrocarbon group of at least 1 but not more than 12 carbon atoms. Examples of the monovalent hydrocarbon group of at least 1 but not more than 12 carbon atoms for $R^{231}$, $R^{232}$ and $R^{233}$ include the same groups as those exemplified above for $R^{211}$.

($Y^{231}$, $Y^{232}$ and $Y^{233}$)

Each of $Y^{231}$, $Y^{232}$ and $Y^{233}$ independently represents a single bond or a divalent hydrocarbon group of at least 1 but not more than 20 carbon atoms which may include at least one group selected from the group consisting of an ester group and an ether group. Examples of the divalent hydrocarbon group of at least 1 but not more than 20 carbon atoms which may include at least one group selected from the group consisting of an ester group and an ether group for $Y^{231}$, $Y^{232}$ and $Y^{233}$ include the same groups as those exemplified above for $Y^{211}$.

Examples of preferred compounds (II-1-3) include 1,3,5-triaminobenzene, 1,3,5-triamino-2-methylbenzene, 1,3,5-tris(1-aminopropan-2-yl)benzene, 1,3,5-tris(1-aminopropan-2-yl)-2-methylbenzene, 1,3,5-tris(1-aminomethyl)2-methylbenzene, and 2,2'-(2-amino-1,3-phenylene)bis(methylene)bis(aminobenzene).

1-2) Amino Acid (II-2) and Amino Acid Ester (II-3)

Further, in the amine compound (11), in the case of a monofunctional amine in which n21 is 1 (namely, a compound having one primary amino group per molecule), the amine compound (11) may be at least one of an α-amino acid represented by general formula (II-2) shown below (hereafter sometimes referred to as "the amino acid (II-2)"), and an α-amino acid ester represented by general formula (II-3) shown below (hereafter sometimes referred to as "the amino acid ester (II-3)").

In an α-amino acid, there are two possible three-dimensional bonding arrangements of the amino group and the carboxyl group and the like to the α-carbon atom, and these arrangements are distinguished as the D- and L-optical isomers. The above amino acid (or the compound having an amino acid skeleton such as the amino acid ester) may be the D-isomer, the L-isomer, or a mixture or racemate thereof. Most amino acids that can be obtained industrially at low cost are amino acids produced by fermentation, and are almost all L-isomers, and these amino acids can be used favorably. In this description, the three-dimensional configuration is not shown, indicating that either the D-isomer or the L-isomer may be used.

[Chemical formula 15]

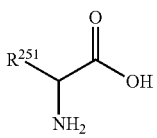

(II-2)

In general formula (II-2), $R^{251}$ represents a hydrogen atom or a monovalent organic group.

[Chemical formula 16]

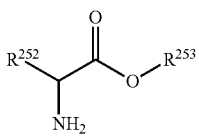

(II-3)

In general formula (II-3), each of $R^{252}$ and $R^{253}$ independently represents a monovalent organic group.

1-2-1) Amino Acid (II-2)

The amino acid (II-2) is a compound represented by the general formula (II-2) shown above.

($R^{251}$)

In general formula (II-2), $R^{251}$ represents a monovalent organic group. The monovalent organic group is preferably a monovalent aliphatic hydrocarbon group of at least 1 but not more than 20 carbon atoms or a monovalent aromatic hydrocarbon group of at least 6 but not more than 20 carbon atoms.

The monovalent aliphatic hydrocarbon group of at least 1 but not more than 20 carbon atoms may be chain-like or cyclic. When the monovalent aliphatic hydrocarbon group of at least 1 but not more than 20 carbon atoms is chain-like, the group may be linear or branched. Specific examples of the chain-like aliphatic hydrocarbon group include a methyl group, ethyl group, propyl group, butyl group and pentyl group. When the monovalent aliphatic hydrocarbon group of at least 1 but not more than 20 carbon atoms is cyclic, the group may be polycyclic or monocyclic. Specific examples of the monocyclic aliphatic hydrocarbon group include cyclopentane and cyclohexane. Specific examples of the polycyclic aliphatic hydrocarbon group include adaimantane, norbornane, isobornane, tricyclodecane and tetracyclododecane.

Examples of the monovalent aromatic hydrocarbon group of at least 6 but not more than 20 carbon atoms include a phenyl group, methylphenyl group (each isomer), ethylphenyl group (each isomer), propylphenyl group (each isomer), butylphenyl group (each isomer), pentylphenyl group (each isomer), hexylphenyl group (each isomer), dimethylphenyl group (each isomer), methylethylphenyl group (each isomer), methylpropylphenyl group (each isomer), methylbutylphenyl group (each isomer), methylpentylphenyl group (each isomer), diethylphenyl group (each isomer), ethylpropylphenyl group (each isomer), ethylbutylphenyl group (each isomer), dipropylphenyl group (each isomer), trimethylphenyl group (each isomer), triethylphenyl group (each isomer), and naphthyl group (each isomer).

Further, in the monovalent aliphatic hydrocarbon groups of at least 1 but not more than 20 carbon atoms and the monovalent aromatic hydrocarbon groups of at least 6 but not more than 20 carbon atoms for $R^{251}$, at least one of the hydrogen atoms within these groups may be substituted with a functional group such as an amino group, guanidino group, hydroxy group, thiol group, carboxy group, carboxamide group, or heterocyclic group. Examples of the heterocyclic group include an indole ring group, imidazole ring group and pyrrolidine ring group. Further, in the monovalent aliphatic hydrocarbon groups of at least 1 but not more than 20 carbon atoms and the monovalent aromatic hydrocarbon groups of at least 6 but not more than 20 carbon atoms for $R^{251}$, a carbon atom that constitutes these groups may be substituted with a sulfur atom, or a carbon-carbon bond may be substituted with a disulfide bond.

Examples of preferred amino acids (II-2) include lysine, arginine, alanine, asparagine, aspartic acid, cysteine, glutamine, glutamic acid, glycine, histidine, isoleucine, leucine, methionine, phenylalanine, proline, serine, threonine, tryptophan, tyrosine and valine.

1-2-2) Amino Acid Ester (II-3)

The amino acid ester (II-3) is a compound represented by the above general formula (II-3).

($R^{252}$ and $R^{253}$)

In general formula (II-3), each of $R^{252}$ and $R^{253}$ independently represents a monovalent organic group.

Examples of $R^{252}$ and $R^{253}$ include the same groups as those exemplified above for $R^{251}$.

Examples of preferred amino acid esters (II-3) include compounds represented by general formula (II-3-1) shown below and compounds represented by general formula (II-3-2) shown below, and esterification using a conventional technique is one preferred embodiment. Further, this step for forming the ester may be conducted favorably either before or after step (1) described above. By conducting an esterification, the carboxy group of the corresponding amino acid is protected, and the substrate stability improves when used as a substrate.

[Chemical formula 17]

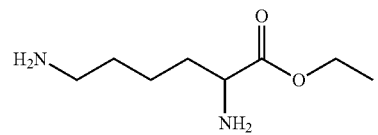

(II-3-1)

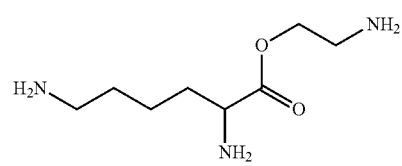 [SMILES: NCCCCC(N)C(=O)OCCN]

(II-3-1)

Further, the amino group contained in the amino acid (II-2) or the amino acid ester (II-3) may exist in the form of a salt with an acid. For example, in the case of a salt with an inorganic acid, examples of the inorganic acid include hydrochloric acid, nitric acid, phosphoric acid and sulfuric acid.

Furthermore, the carboxy group contained in the amino acid (II-2) may exist in the form of a salt with a base. For example, in the case of a salt with an inorganic base, examples of the inorganic base include alkali metal hydroxides and alkaline earth metal hydroxides. Examples of the alkali metal hydroxides include sodium hydroxide and potassium hydroxide. Examples of the alkaline earth metal hydroxides include calcium hydroxide and magnesium hydroxide. In the case of a salt with an organic base, examples of the organic base include primary amines, secondary amines, tertiary amines and ammonia. Examples of the primary amines include butylamine and octylamine. Examples of the secondary amines include dibutylamine, dioctylamine and imidazole. Examples of the tertiary amines include triethylamine, tributylamine and pyridine.

The organic primary amine used in step (1) may be any compound having at least one amino group in the molecule, but a compound having two amino groups is more preferred, and a compound having two amino groups is even more preferred. By increasing the number of amino groups per molecule, the functionality obtained when the isocyanate compound corresponding with the organic primary amine is used as the production raw material for a polyurethane foam, coating material or adhesive or the like (for example, the hardness of the polyurethane foam) can be improved.

[Carbon Dioxide and Carbonic Acid Derivative]

The carbon dioxide used in step (1) may be the gaseous state of any grade typically used in industrial applications, and there are no particular limitations.

Further, in the present description, the term "carbonic acid derivative" is a general term indicating all compounds having a carbonyl group (—C(=O)—). The carbonic acid derivative used in step 1 is preferably at least one compound selected from among N-unsubstituted carbamate esters, N,N'-disubstituted ureas, N-substituted ureas and urea.

(N-Unsubstituted Carbamate Esters)

The N-unsubstituted carbamate ester is preferably a compound represented by general formula (III-1) shown below (hereafter sometimes referred to as "the compound (III-1)").

[Chemical formula 18]

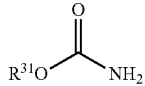

(III-1)

In general formula (II-1), $R^{31}$ represents an aliphatic hydrocarbon group of at least 1 but not more than 20 carbon atoms or an aromatic hydrocarbon group of at least 6 but not more than 20 carbon atoms which may contain an oxygen atom.

In general formula (III-1), in those cases where $R^3$ is an aliphatic hydrocarbon group, examples of the aliphatic hydrocarbon group include chain-like hydrocarbon groups, cyclic hydrocarbon groups, and groups composed of a chain-like hydrocarbon group and a cyclic hydrocarbon group bonded together. Examples of these groups composed of a chain-like hydrocarbon group and a cyclic hydrocarbon group bonded together include cyclic hydrocarbon groups in which at least one hydrogen atom is substituted with a chain-like hydrocarbon group, and chain-like hydrocarbon groups in which at least one hydrogen atom is substituted with a cyclic hydrocarbon group (aralkyl groups).

Specific examples of the aralkyl groups include groups in which a linear or branched alkyl group has been substituted with an aromatic hydrocarbon group, and groups in which a linear or branched alkyl group of at least 1 but not more than 14 carbon atoms has been substituted with an aromatic hydrocarbon group of at least 6 but not more than 19 carbon atoms.

In those cases where $R^{31}$ is an aromatic hydrocarbon group, examples of the aromatic hydrocarbon group include monocyclic aromatic hydrocarbon groups, condensed polycyclic aromatic hydrocarbon groups, crosslinked cyclic aromatic hydrocarbon groups, ring-aggregated aromatic hydrocarbon groups, and heterocyclic aromatic hydrocarbon groups, and a substituted or unsubstituted phenyl group, substituted or unsubstituted naphthyl group, or substituted or unsubstituted anthryl group is preferred.

Examples of the substituent include a hydrogen atom, and the aliphatic hydrocarbon groups and aromatic hydrocarbon groups described above, and the substituent may also be composed of an aforementioned aliphatic hydrocarbon group and aromatic hydrocarbon group.

Among the various possibilities, $R^{31}$ is preferably an alkyl group of at least 1 but not more than 20 carbon atoms, an aryl group of at least 6 but not more than 20 carbon atoms, or an aralkyl group of at least 7 but not more than 20 carbon atoms.

Examples of the alkyl group of at least 1 but not more than 20 carbon atoms include a methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group and octadecyl group. Examples of the aryl group of at least 6 but not more than 20 carbon atoms include a phenyl group, methylphenyl group, ethylphenyl group, propylphenyl group, butylphenyl group, pentylphenyl group, hexylphenyl group, heptylphenyl group, octylphenyl group, nonylphenyl group, decylphenyl group, cumylphenyl group, biphenyl group, dimethylphenyl group, diethylphenyl group, dipropylphenyl group, dibutylphenyl group, dipentylphenyl group, dihexylphenyl group, diheptylphenyl group, terphenyl group, trimethylphenyl group, triethylphenyl group, tripropylphenyl group and tributylphenyl group. Examples of the aralkyl group of at least 7 but not more than 20 carbon atoms include a phenylmethyl group, phenylethyl group, phenylpropyl group, phenylbutyl group, phenylpentyl group, phenylhexyl group, phenylheptyl group, phenyloctyl group and phenylnonyl group.

Among the various possibilities, $R^{31}$ is more preferably an alkyl group of at least 1 but not more than 8 carbon atoms or an aryl group of at least 6 but not more than 15 carbon atoms. Examples of the alkyl group of at least 1 but not more than 8 carbon atoms include a methyl group, ethyl group, propyl group, butyl group, pentyl group, hexyl group, heptyl group and octyl group. Examples of the aryl group of at least 6 but not more than 15 carbon atoms include a phenyl group, methylphenyl group, ethylphenyl group, propylphenyl group, butylphenyl group, pentylphenyl group, octylphenyl group, nonylphenyl group, cumylphenyl group, biphenyl group, dimethylphenyl group, diethylphenyl group, dipropylphenyl group and dipentylphenyl group.

Specific examples of preferred compounds (III-1) include methyl carbamate, ethyl carbamate, propyl carbamate, butyl carbamate, pentyl carbamate, hexyl carbamate, heptyl carbamate, octyl carbamate, nonyl carbamate, decyl carbamate, undecyl carbamate, dodecyl carbamate, tridecyl carbamate, tetradecyl carbamate, pentadecyl carbamate, hexadecyl carbamate, heptadecyl carbamate, octadecyl carbamate, nonadecyl carbamate, phenyl carbamate, (methylphenyl) carbamate, (ethylphenyl) carbamate, (propylphenyl) carbamate, (butylphenyl) carbamate, (pentylphenyl) carbamate, (hexylphenyl) carbamate, (heptylphenyl) carbamate, (octylphenyl) carbamate, (nonylphenyl) carbamate, (decylphenyl) carbamate, (biphenyl) carbamate, (dimethylphenyl) carbamate, (diethylphenyl) carbamate, (dipropylphenyl) carbamate, (dibutylphenyl) carbamate, (dipentylphenyl) carbamate, (dihexylphenyl) carbamate, (diheptylphenyl) carbamate, (terphenyl) carbamate, (trimethylphenyl) carbamate, (triethylphenyl) carbamate, (tripropylphenyl) carbamate, (tributylphenyl) carbamate, (phenylmethyl) carbamate, (phenylethyl) carbamate, (phenylpropyl) carbamate, (phenylbutyl) carbamate, (phenylpentyl) carbamate, (phenylhexyl) carbamate, (phenylheptyl) carbamate, (phenyloctyl) carbamate and (phenylnonyl) carbamate.

(N,N'-Disubstituted Ureas, N-Substituted Ureas)

The N,N'-disubstituted urea is preferably a compound represented by general formula (III-2) shown below (hereafter sometimes referred to as "the compound (III-2)").

[Chemical formula 19]

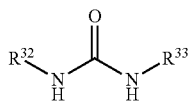

(III-2)

In general formula (III-2), each of $R^{32}$ and $R^{33}$ independently represents an aliphatic hydrocarbon group of at least 1 but not more than 20 carbon atoms, an aromatic hydrocarbon group of at least 6 but not more than 20 carbon atoms, or a hydrogen atom. $R^{32}$ and $R^{33}$ cannot both be hydrogen atoms.

Examples of the aliphatic hydrocarbon group of at least 1 but not more than 20 carbon atoms and the aromatic hydrocarbon group of at least 6 but not more than 20 carbon atoms for $R^{32}$ and $R^{33}$ include the same groups as those exemplified above for $R^{31}$. Among the various possibilities, $R^{32}$ and $R^{33}$ are each preferably either an alkyl group of at least 1 but not more than 8 carbon atoms or an aralkyl group of at least 6 but not more than 14 carbon atoms, and more preferably a methyl group, ethyl group, propyl group, butyl group, pentyl group, hexyl group, heptyl group, octyl group, phenyl group, methylphenyl group, ethylphenyl group, propylphenyl group, butylphenyl group, pentylphenyl group, octylphenyl group, nonylphenyl group, cumylphenyl group, biphenyl group, dimethylphenyl group, diethylphenyl group, dipropylphenyl group or dipentylphenyl group.

[Carbonate Ester]

The carbonate ester used in step (2) is preferably a compound represented by general formula (IV) shown below (hereafter sometimes referred to as "the compound (IV)").

[Chemical formula 20]

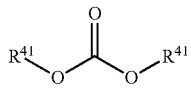

(IV)

In general formula (IV), each of the plurality of $R^{41}$ groups independently represents an aliphatic hydrocarbon group of at least 1 but not more than 20 carbon atoms or an aromatic hydrocarbon group of at least 6 but not more than 20 carbon atoms. The plurality of $R^{81}$ groups may be the same or different. Among the various possibilities, the plurality of $R^{41}$ groups are preferably the same.

($R^{41}$)

Examples of the monovalent organic group for $R^{41}$ include the same groups as those exemplified above for the monovalent organic group for $R^{21}$.

Examples of preferred compounds for the compound (IV) include diaryl carbonate represented by general formula (IV-1) shown below (hereafter sometimes referred to as the "diaryl carbonate (IV-1)").

These compounds are merely examples of preferred compound (IV), and the preferred compounds (IV) are not limited to these compounds.

[Chemical formula 21]

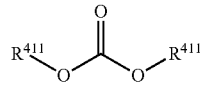

(IV-1)

In general formula (IV-1), each of the plurality of $R^{411}$ groups independently represents an aromatic hydrocarbon group of at least 6 but not more than 20 carbon atoms.

Each $R^{411}$ represents an aromatic hydrocarbon group of at least 6 but not more than 20 carbon atoms, and is preferably an aromatic hydrocarbon group of at least 6 but not more than 12 carbon atoms, and more preferably an aromatic hydrocarbon group of at least 6 but not more than 8 carbon atoms. Specific examples of $R^{411}$ include the same groups as those aromatic hydrocarbon group of at least 6 but not more than 20 carbon atoms exemplified above for $R^{251}$.

Examples of preferred diaryl carbonates (IV-1) include diaryl carbonates in which $R^{411}$ represents an aromatic hydrocarbon group of at least 6 but not more than 8 carbon atoms. Specific examples of such diaryl carbonates (IV-1) include diphenyl carbonate, di(methylphenyl) carbonate (each isomer), di(diethylphenyl) carbonate (each isomer), and di(methylethylphenyl) carbonate (each isomer).

These compounds are merely examples of preferred diaryl carbonates (IV-1), and the preferred diaryl carbonates (IV-1) are not limited to these compounds.

Further, the carbonate ester may include a metal atom. The metal atom content relative to the mass of the carbonate ester is preferably within a range from at least 0.001 ppm to no more than 100,000 ppm, more preferably within a range from at least 0.001 ppm to no more than 50,000 ppm, and even more preferably within a range from at least 0.002 ppm to no more than 30,000 ppm.

Furthermore, the metal atom may exist as metal ions or as stand-alone metal atoms. Of the various possibilities, metal atoms that can adopt a valence of at least 2 but not more than 4 are preferred, and one or more metals selected from the group consisting of iron, cobalt, nickel, zinc, tin, copper and titanium is more preferred.

Conventional methods may be used as the method for producing the carbonate ester. Of the various methods, the method disclosed in International Patent Publication 2009/139061 (Patent Document 8), which involves reacting an organotin compound having a tin-oxygen-carbon linkage with carbon dioxide to produce an aliphatic carbonate ester, and then producing an aromatic carbonate ester (namely, a diaryl carbonate) from the aliphatic carbonate ester and an aromatic hydroxy compound is preferred.

[Carbamate] 1) Carbamate (V)

The carbamate obtained in the production method of the present embodiment is preferably a carbamate represented by general formula (V) shown below (hereafter sometimes referred to as "the carbamate (V)").

[Chemical formula 22]

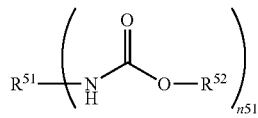

In general formula (V), n51 is the same as n21 described above. $R^{51}$ is the same as $R^{21}$ described above. $R^{52}$ is the same as $R^{51}$.

In the carbamate (V), in the case of a difunctional carbamate in which n51 is 2 (namely, a compound having two carbamate groups per molecule), examples of preferred carbamates (V) include aliphatic dicarbamates of at least 4 but not more than 30 carbon atoms, alicyclic dicarbamates of at least 8 but not more than 30 carbon atoms, and dicarbamates containing an aromatic group of at least 8 but not more than 30 carbon atoms.

Specific examples of the aliphatic dicarbamates of at least 4 but not more than 30 carbon atoms include 1,4-tetramethylene di, 1,5-pentamethylene di(carbamic acid methyl ester), 2-methylbutane-1,4-di(carbamic acid methyl ester), 1,6-hexamethylene di(carbamic acid methyl ester), 2,5-dimethylhexane-1,6-di(carbamic acid methyl ester), 2,2,4-trimethyl-1,6-hexamethylene di(carbamic acid methyl ester), lysine methyl ester di(carbamic acid methyl ester), lysine ethyl ester di(carbamic acid methyl ester), 1,4-tetramethylene di, 1,5-pentamethylene di(carbamic acid ethyl ester), 2-ethylbutane-1,4-di(carbamic acid ethyl ester), 1,6-hexamethylene di(carbamic acid ethyl ester), 2,5-diethylhexane-1,6-di(carbamic acid ethyl ester), 2,2,4-triethyl-1,6-hexamethylene di(carbamic acid ethyl ester), lysine ethyl ester di(carbamic acid ethyl ester), lysine ethyl ester di(carbamic acid ethyl ester), 1,4-tetramethylene di, 1,5-pentamethylene di(carbamic acid butyl ester), 2-butylbutane-1,4-di(carbamic acid butyl ester), 1,6-hexamethylene di(carbamic acid butyl ester), 2,5-dibutylhexane-1,6-di(carbamic acid butyl ester), 2,2,4-tributyl-1,6-hexamethylene di(carbamic acid butyl ester), lysine butyl ester di(carbamic acid butyl ester), lysine butyl ester di(carbamic acid butyl ester), 1,4-tetramethylene di, 1,5-pentamethylene di(carbamic acid phenyl ester), 2-phenylbutane-1,4-di(carbamic acid phenyl ester), 1,6-hexamethylene di(carbamic acid phenyl ester), 2,5-diphenylhexane-1,6-di(carbamic acid phenyl ester), 2,2,4-triphenyl-1,6-hexamethylene di(carbamic acid phenyl ester), lysine phenyl ester di(carbamic acid phenyl ester), lysine phenyl ester di(carbamic acid phenyl ester), 1,4-tetramethylene di, 1,5-pentamethylene di(carbamic acid dimethylphenyl ester), 2-dimethylphenylbutane-1,4-di(carbamic acid dimethylphenyl ester), 1,6-hexamethylene di(carbamic acid dimethylphenyl ester), 2,5-didimethylphenylhexane-1,6-di(carbamic acid dimethylphenyl ester), 2,2,4-tridimethylphenyl-1,6-hexamethylene di(carbamic acid dimethylphenyl ester), lysine dimethylphenyl ester di(carbamic acid dimethylphenyl ester), lysine dimethylphenyl ester di(carbamic acid dimethylphenyl ester), 1,4-tetramethylene di, 1,5-pentamethylene di(carbamic acid dibutylphenyl ester), 2-dibutylphenylbutane-1,4-di(carbamic acid dibutylphenyl ester), 1,6-hexamethylene di(carbamic acid dibutylphenyl ester), 2,5-dibutylphenylhexane-1,6-di(carbamic acid dibutylphenyl ester), 2,2,4-tridibutylphenyl-1,6-hexamethylene di(carbamic acid dibutylphenyl ester), lysine dibutylphenyl ester di(carbamic acid dibutylphenyl ester), and lysine dibutylphenyl ester di(carbamic acid dibutylphenyl ester).

Specific examples of the alicyclic dicarbamates of at least 8 but not more than 30 carbon atoms include isophorone di(carbamic acid methyl ester), 1,3-bis((carbamic acid methyl ester)methyl)-cyclohexane, 4,4'-dicyclohexylmethane di(carbamic acid methyl ester), hydrogenated tetramethylxylylene di(carbamic acid methyl ester), norbornene di(carbamic acid methyl ester), isophorone di(carbamic acid ethyl ester), 1,3-bis((carbamic acid ethyl ester)ethyl)-cyclohexane, 4,4'-dicyclohexylmethane di(carbamic acid ethyl ester), hydrogenated tetraethylxylylene di(carbamic acid ethyl ester), norbornene di(carbamic acid ethyl ester), isophorone di(carbamic acid butyl ester), 1,3-bis((carbamic acid butyl ester)butyl)-cyclohexane, 4,4'-dicyclohexylmethane di(carbamic acid butyl ester), hydrogenated tetrabutylxylylene di(carbamic acid butyl ester), norbornene di(carbamic acid butyl ester), isophorone di(carbamic acid phenyl ester), 1,3-bis((carbamic acid phenyl ester)phenyl)-cyclohexane, 4,4'-dicyclohexylmethane di(carbamic acid phenyl ester), hydrogenated tetraphenylxylylene di(carbamic acid phenyl ester), norbornene di(carbamic acid phenyl ester), isophorone di(carbamic acid dimethylphenyl ester), 1,3-bis((carbamic acid dimethylphenyl ester)dimethylphenyl)-cyclohexane, 4,4'-dicyclohexylmethane di(carbamic acid dimethylphenyl ester), hydrogenated tetradimethylphenylxylylene di(carbamic acid dimethylphenyl ester), and norbornene di(carbamic acid dimethylphenyl ester).

Specific examples of the dicarbamates containing an aromatic group of at least 8 but not more than 30 carbon atoms include 4,4'-diphenylmethane di(carbamic acid methyl ester), 2,6-tolylene di(carbamic acid methyl ester), xylylene di(carbamic acid methyl ester), tetramethylxylylene di(carbamic acid methyl ester), naphthalene di(carbamic acid methyl ester), 4,4'-diphenylmethane di(carbamic acid ethyl ester), 2,6-tolylene di(carbamic acid ethyl ester), xylylene di(carbamic acid ethyl ester), tetraethylxylylene di(carbamic acid ethyl ester), naphthalene di(carbamic acid ethyl ester), 4,4'-diphenylmethane di(carbamic acid butyl ester), 2,6-tolylene di(carbamic acid butyl ester), xylylene di(carbamic acid butyl ester), tetrabutylxylylene di(carbamic acid butyl ester), naphthalene di(carbamic acid butyl ester), 4,4'-diphenylmethane di(carbamic acid phenyl ester), 2,6-tolylene di(carbamic acid phenyl ester), xylylene di(carbamic acid phenyl ester), tetraphenylxylylene di(carbamic acid phenyl ester), naphthalene di(carbamic acid phenyl ester), 4,4'-dimethylphenylmethane di(carbamic acid dimethylphenyl ester), 2,6-tolylene di(carbamic acid dimethylphenyl ester), xylylene di(carbamic acid dimethylphenyl ester), tetradimethylphenylxylylene di(carbamic acid dimethylphenyl ester), and naphthalene di(carbamic acid dimethylphenyl ester).

In those cases where structural isomers exist for any of the above compounds, those structural isomers are also included within the examples of preferred carbamates (V).

Further, these compounds are merely examples of preferred carbamates (V), and the preferred carbamates (V) are not limited to the compounds listed above.

1-1) Carbamate (V-1)

In the carbamate (V), in the case of a trifunctional carbamate in which n51 is 3 (namely, a compound having three carbamate groups per molecule), examples of preferred carbamates (V) include carbamates represented by general formula (V-1) shown below (hereafter sometimes referred to as "the carbamate (V-1)").

These compounds are merely examples of preferred carbamates (V), and the preferred carbamates (V) are not limited to these compounds.

[Chemical formula 23]

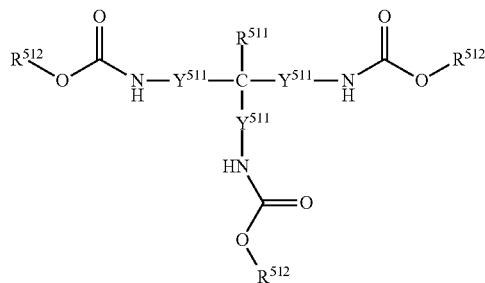

(V-1)

In general formula (V-1), the plurality of $Y^{511}$ and $R^{512}$ groups and $R^{511}$ are the same as the aforementioned $Y^{211}$, $R^{41}$ and $R^{211}$ respectively.

Examples of preferred carbamates (V-1) include compounds in which $Y^{51}$ is a divalent aliphatic hydrocarbon group of at least 1 but not more than 20 carbon atoms, compounds in which $Y^{511}$ is a divalent aromatic hydrocarbon group of at least 6 but not more than 20 carbon atoms, compounds represented by general formula (V-1-1) shown below (hereafter sometimes referred to as "the compound (V-1-1)"), compounds represented by general formula (V-1-2) shown below (hereafter sometimes referred to as "the compound (V-1-2)"), and compounds represented by general formula (V-1-3) shown below (hereafter sometimes referred to as "the compound (V-1-3)").

[Chemical formula 24]

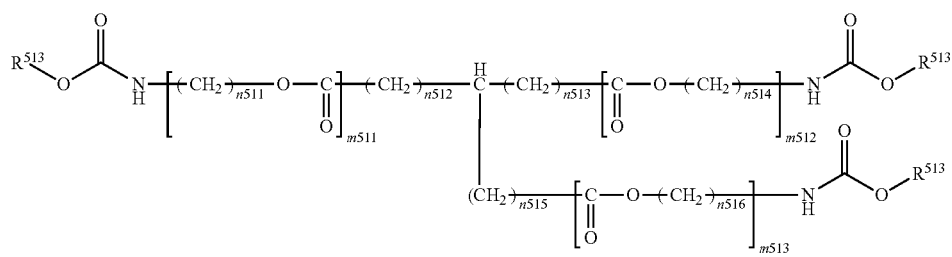

(V-1-1)

In general formula (V-1-1), the plurality of $R^{513}$ groups are the same as $R^{41}$ described above. Further, m511, m512 and m513 are the same as the aforementioned m211, m212 and m213 respectively. Moreover, n511, n512, n513, n514, n515 and n516 are the same as the aforementioned n211, n212, n213, n214, n215 and n216 respectively.

[Chemical formula 25]

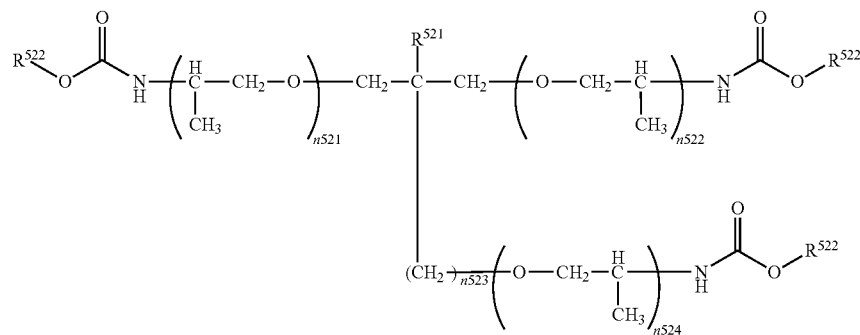

(V-1-2)

In general formula (V-1-2), the $R^{521}$ group and plurality of $R^{522}$ groups are the same as the aforementioned $R^{251}$ and $R^{41}$ respectively. Further, n521, n522, n523 and n524 are the same as the aforementioned n221, n222, n223 and n224 respectively.

[Chemical formula 26]

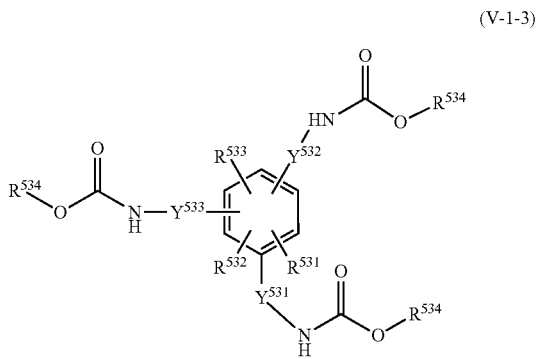

(V-1-3)

In general formula (V-1-3), $R^{531}$, $R^{532}$, $R^{533}$ and the plurality of $R^{534}$ groups are the same as the aforementioned $R^{231}$, $R^{232}$, $R^{233}$ and $R^{41}$ respectively. $Y^{231}$, $Y^{232}$ and $Y^{233}$ are the same as the aforementioned $Y^{231}$, $Y^{232}$ and $Y^{233}$ respectively.

Specific examples of compounds in which $Y^{511}$ is a divalent aliphatic hydrocarbon group of at least 1 but not more than 20 carbon atoms include 1,8-di(carbamic acid methyl ester)-4-(carbamic acid methyl ester)methyloctane, 1,3,6-tri(carbamic acid methyl ester)hexane, 1,8-di(carbamic acid methyl ester)-4-((carbamic acid methyl ester)methyl)-2,4,7-trimethyloctane, 1,5-di(carbamic acid methyl ester)-3-((carbamic acid methyl ester)methyl)pentane, 1,6,11-tri(carbamic acid methyl ester)undecane, 1,4,7-tri(carbamic acid methyl ester)heptane, 1,2,2-tri(carbamic acid methyl ester)butane, 1,2,6-tri(carbamic acid methyl ester)hexane, 1-(carbamic acid methyl ester)-2,2-bis((carbamic acid methyl ester)methyl)butane, 1,3,5-tri(carbamic acid methyl ester)cyclohexane, 1,7-di(carbamic acid methyl ester)-4-(3-(carbamic acid methyl ester)propyl)heptane, 1,3-di(carbamic acid methyl ester)-2-((carbamic acid methyl ester)methyl)-2-methylpropane, 1,3,5-tri(carbamic acid methyl ester)benzene, 1,3,5-tri(carbamic acid methyl ester)-2-methylbenzene, 1,3,5-tris(1-(carbamic acid methyl ester)propan-2-yl)benzene, 1,3,5-tris(1-(carbamic acid methyl ester)propan-2-yl)-2-methylbenzene, 1,3,5-tris(1-(carbamic acid methyl ester)methyl)-2-methylbenzene, 2,2'-((2-(carbamic acid methyl ester)-1,3-phenylene)bis(methylene)bis(carbamic acid methyl ester)benzene), 1,8-di(carbamic acid ethyl ester)-4-(carbamic acid ethyl ester)ethyloctane, 1,3,6-tri(carbamic acid ethyl ester)hexane, 1,8-di(carbamic acid ethyl ester)-4-((carbamic acid ethyl ester)ethyl)-2,4,7-triethyloctane, 1,5-di(carbamic acid ethyl ester)-3-((carbamic acid ethyl ester)ethyl)pentane, 1,6,11-tri(carbamic acid ethyl ester)undecane, 1,4,7-tri(carbamic acid ethyl ester)heptane, 1,2,2-tri(carbamic acid ethyl ester)butane, 1,2,6-tri(carbamic acid ethyl ester)hexane, 1-(carbamic acid ethyl ester)-2,2-bis((carbamic acid ethyl ester)ethyl)butane, 1,3,5-tri(carbamic acid ethyl ester)cyclohexane, 1,7-di(carbamic acid ethyl ester)-4-(3-(carbamic acid ethyl ester)propyl)heptane, 1,3-di(carbamic acid ethyl ester)-2-((carbamic acid ethyl ester)ethyl)-2-ethylpropane, 1,3,5-tri(carbamic acid ethyl ester)benzene, 1,3,5-tri(carbamic acid ethyl ester)-2-ethylbenzene, 1,3,5-tris(1-(carbamic acid ethyl ester)propan-2-yl)benzene, 1,3,5-tris(1-(carbamic acid ethyl ester)propan-2-yl)-2-ethylbenzene, 1,3,5-tris(1-(carbamic acid ethyl ester)ethyl)-2-ethylbenzene, 2,2'-((2-(carbamic acid ethyl ester)-1,3-phenylene)bis(methylene)bis(carbamic acid ethyl ester)benzene), 1,8-di(carbamic acid butyl ester)-4-(carbamic acid butyl ester)butyloctane, 1,3,6-tri(carbamic acid butyl ester)hexane, 1,8-di(carbamic acid butyl ester)-4-((carbamic acid butyl ester)butyl)-2,4,7-tributyloctane, 1,5-di(carbamic acid butyl ester)-3-((carbamic acid butyl ester)butyl)pentane, 1,6,11-tri(carbamic acid butyl ester)undecane, 1,4,7-tri(carbamic acid butyl ester)heptane, 1,2,2-tri(carbamic acid butyl ester)butane, 1,2,6-tri(carbamic acid butyl ester)hexane, 1-(carbamic acid butyl ester)-2,2-bis((carbamic acid butyl ester)butyl)butane, 1,3,5-tri(carbamic acid butyl ester)cyclohexane, and 1,7-di(carbamic acid butyl ester)-4-(3-(carbamic acid butyl ester)propyl)heptane.

Specific examples of compounds in which $Y^{51}$ is a divalent aromatic hydrocarbon group of at least 6 but not more than 20 carbon atoms include 1,3-di(carbamic acid butyl ester)-2-((carbamic acid butyl ester)butyl)-2-butylpropane, 1,3,5-tri(carbamic acid butyl ester)benzene, 1,3,5-tri(carbamic acid butyl ester)-2-butylbenzene, 1,3,5-tris(1-(carbamic acid butyl ester)propan-2-yl)benzene, 1,3,5-tris(1-(carbamic acid butyl ester)propan-2-yl)-2-butylbenzene, 1,3,5-tris(1-(carbamic acid butyl ester)butyl)-2-butylbenzene, 2,2'-((2-(carbamic acid butyl ester)-1,3-phenylene)bis(methylene))bis(carbamic acid butyl ester)benzene), 1,8-di(carbamic acid phenyl ester)-4-(carbamic acid phenyl ester)phenyloctane, 1,3,6-tri(carbamic acid phenyl ester)hexane, 1,8-di(carbamic acid phenyl ester)-4-((carbamic acid phenyl ester)phenyl)-2,4,7-triphenyloctane, 1,5-di(carbamic acid phenyl ester)-3-((carbamic acid phenyl ester)phenyl)pentane, 1,6,11-tri(carbamic acid phenyl ester)undecane, 1,4,7-tri(carbamic acid phenyl ester)heptane, 1,2,2-tri(carbamic acid phenyl ester)butane, 1,2,6-tri(carbamic acid phenyl ester)hexane, 1-(carbamic acid phenyl ester)-2,2-bis((carbamic acid phenyl ester)phenyl)butane, 1,3,5-tri(carbamic acid phenyl ester)cyclohexane, 1,7-di(carbamic acid phenyl ester)-4-(3-(carbamic acid phenyl ester)propyl)heptane, 1,3-di(carbamic acid phenyl ester)-2-((carbamic acid phenyl ester)phenyl)-2-phenylpropane, 1,3,5-tri(carbamic acid phenyl ester)benzene, 1,3,5-tri(carbamic acid phenyl ester)-2-phenylbenzene, 1,3,5-tris(1-(carbamic acid phenyl ester)propan-2-yl)benzene, 1,3,5-tris(1-(carbamic acid phenyl ester)propan-2-yl)-2-phenylbenzene, 1,3,5-tris(1-(carbamic acid phenyl ester)phenyl)-2-phenylbenzene, 2,2'-((2-(carbamic acid phenyl ester)-1,3-phenylene)bis(methylene))bis(carbamic acid phenyl ester)benzene), 1,8-di(carbamic acid dimethylphenyl ester)-4-(carbamic acid dimethylphenyl ester)dimethylphenyloctane, 1,3,6-tri(carbamic acid dimethylphenyl ester)hexane, 1,8-di(carbamic acid dimethylphenyl ester)-4-((carbamic acid dimethylphenyl ester)dimethylphenyl)-2,4,7-tridimethylphenyloctane, 1,5-di(carbamic acid dimethylphenyl ester)-3-((carbamic acid dimethylphenyl ester)dimethylphenyl)pentane, 1,6,11-tri(carbamic acid dimethylphenyl ester)undecane, 1,4,7-tri(carbamic acid dimethylphenyl ester)heptane, 1,2,2-tri(carbamic acid dimethylphenyl ester)butane, 1,2,6-tri(carbamic acid dimethylphenyl ester)hexane, 1-(carbamic acid dimethylphenyl ester)-2,2-bis((carbamic acid dimethylphenyl ester)dimethylphenyl)butane, 1,3,5-tri(carbamic acid dimethylphenyl ester)cyclohexane, 1,7-di(carbamic acid dimethylphenyl ester)-4-(3-(carbamic acid dimethylphenyl ester)propyl)heptane, 1,3-di(carbamic acid dimethylphenyl ester)-2-((carbamic acid dimethylphenyl ester)dimethylphenyl)-2-dimethylphenylpropane, 1,3,5-tri(carbamic acid dimethylphenyl ester)benzene, 1,3,5-tri(carbamic acid dimethylphenyl ester)-2-dimethylphenylbenzene, 1,3,5-tris(1-(carbamic acid dimethylphenyl ester)propan-2-yl)benzene, 1,3,5-tris(1-(carbamic acid dimethylphenyl ester)propan-2-yl)-2-dimethylphenylbenzene, 1,3,5-tris(1-(carbamic acid dimethylphenyl ester)dimethylphenyl)-2-dimethylphenylbenzene, and 2,2'-((2-(carbamic acid dimethylphenyl ester)-1,3-phenylene)bis(methylene))bis(carbamic acid dimethylphenyl ester)benzene.

1-1-1) Compound (V-1-1)

Specific examples of preferred compounds (V-1-1) include the compounds listed below.

In general formula (V-1-1), m511=m512=m513=0 n512=n513=1, and n515=0

1,2,3-propanetri(carbamic acid ethyl ester) ($R^{511}$ in general formula (V-1-1) is an ethyl group)
1,2,3-propanetri(carbamic acid methyl ester) ($R^{511}$ in general formula (V-1-1) is a methyl group)
1,2,3-propanetri(carbamic acid butyl ester) ($R^{511}$ in general formula (V-1-1) is a butyl group)
1,2,3-propanetri(carbamic acid phenyl ester) ($R^{511}$ in general formula (V-1-1) is a phenyl group)
1,2,3-propanetri(carbamic acid dimethylphenyl ester) ($R^{511}$ in general formula (V-1-1) is a dimethylphenyl group)

In general formula (V-1-1), m511=m512=m513=0, n512=n513=n515=2 tris(2-(carbamic acid ethyl ester)ethyl)(carbamic acid ethyl ester) ($R^{511}$ in general formula (V-1-1) is an ethyl group)
tris(2-(carbamic acid methyl ester)ethyl)(carbamic acid methyl ester) ($R^{511}$ in general formula (V-1-1) is a methyl group)
tris(2-(carbamic acid butyl ester)ethyl)(carbamic acid butyl ester) ($R^{511}$ in general formula (V-1-1) is a butyl group)
tris(2-(carbamic acid phenyl ester)ethyl)(carbamic acid phenyl ester) ($R^{511}$ in general formula (V-1-1) is a phenyl group)
tris(2-(carbamic acid dimethylphenyl ester)ethyl)(carbamic acid dimethylphenyl ester) ($R^{511}$ in general formula (V-1-1) is a dimethylphenyl group)

In general formula (V-1-1), m511=m512=m513=0 n512=n513=5, n515=0

1,6,11-tri(carbamic acid ethyl ester)decane ($R^{511}$ in general formula (V-1-1) is an ethyl group)
1,6,11-tri(carbamic acid methyl ester)decane ($R^{511}$ in general formula (V-1-1) is a methyl group)
1,6,11-tri(carbamic acid butyl ester)decane ($R^{511}$ in general formula (V-1-1) is a butyl group)
1,6,11-tri(carbamic acid phenyl ester)decane ($R^{511}$ in general formula (V-1-1) is a phenyl group)
1,6,11-tri(carbamic acid dimethylphenyl ester)decane ($R^{511}$ in general formula (V-1-1) is a dimethylphenyl group)

In general formula (V-1-1), m511=m512=m513=0, n512=3, n513=2, n515=0

1,3,6-hexamethylenetri(carbamic acid ethyl ester) ($R^{511}$ in general formula (V-1-1) is an ethyl group)
1,3,6-hexamethylenetri(carbamic acid methyl ester) ($R^{511}$ in general formula (V-1-1) is a methyl group)
1,3,6-hexamethylenetri(carbamic acid butyl ester) ($R^{511}$ in general formula (V-1-1) is a butyl group)
1,3,6-hexamethylenetri(carbamic acid phenyl ester) ($R^{511}$ in general formula (V-1-1) is a phenyl group)
1,3,6-hexamethylenetri(carbamic acid dimethylphenyl ester) ($R^{511}$ in general formula (V-1-1) is a dimethylphenyl group)

In general formula (V-1-1), m511=m512=m513=0 n512=4, n513=1 n515=3

1,8-di(carbamic acid ethyl ester)-4-((carbamic acid ethyl ester)ethyl)octane ($R^{511}$ in general formula (V-1-1) is an ethyl group)
1,8-di(carbamic acid methyl ester)-4-((carbamic acid methyl ester)ethyl)octane ($R^{511}$ in general formula (V-1-1) is a methyl group)
1,8-di(carbamic acid butyl ester)-4-((carbamic acid butyl ester)ethyl)octane ($R^{511}$ in general formula (V-1-1) is a butyl group)
1,8-di(carbamic acid phenyl ester)-4-((carbamic acid phenyl ester)ethyl)octane ($R^{511}$ in general formula (V-1-1) is a phenyl group)
1,8-di(carbamic acid dimethylphenyl ester)-4-((carbamic acid dimethylphenyl ester)ethyl)octane ($R^{511}$ in general formula (V-1-1) is a dimethylphenyl group)

In general formula (V-1-1), m511=m513=0, m512=1, n512=3, n513=n515=0, n514=2

2-(carbamic acid ethyl ester)ethyl-2,5-di(carbamic acid methyl ester)pentanoate ($R^{511}$ in general formula (V-1-1) is an ethyl group)
2-(carbamic acid methyl ester)ethyl-2,5-di(carbamic acid methyl ester)pentanoate ($R^{511}$ in general formula (V-1-1) is a methyl group)
2-(carbamic acid butyl ester)ethyl-2,5-di(carbamic acid butyl ester)pentanoate ($R^{511}$ in general formula (V-1-1) is a butyl group)
2-(carbamic acid phenyl ester)ethyl-2,5-di(carbamic acid phenyl ester)pentanoate ($R^{511}$ in general formula (V-1-1) is a phenyl group)
2-(carbamic acid dimethylphenyl ester)ethyl-2,5-di(carbamic acid dimethylphenyl ester)pentanoate ($R^{511}$ in general formula (V-1-1) is a dimethylphenyl group)

In general formula (V-1-1), m511=m512=1, m513=0, n511=n514=2, n512=1, n513=n515=0 bis(2-(carbamic acid ethyl ester)ethyl)-2-(carbamic acid ethyl ester)butanedioate ($R^{511}$ in general formula (V-1-1) is an ethyl group)
bis(2-(carbamic acid methyl ester)ethyl)-2-(carbamic acid methyl ester)butanedioate ($R^{511}$ in general formula (V-1-1) is a methyl group)
bis(2-(carbamic acid butyl ester)ethyl)-2-(carbamic acid butyl ester)butanedioate ($R^{511}$ in general formula (V-1-1) is a butyl group)
bis(2-(carbamic acid phenyl ester)ethyl)-2-(carbamic acid phenyl ester)butanedioate ($R^{511}$ in general formula (V-1-1) is a phenyl group)

In general formula (V-1-1), m511=m512=1, m513=0, n511=n514=2, n512=2, n513=n515=0 bis(2-(carbamic acid ethyl ester)ethyl)-2-(carbamic acid ethyl ester)pentanedioate ($R^{511}$ in general formula (V-1-1) is an ethyl group)
bis(2-(carbamic acid methyl ester)ethyl)-2-(carbamic acid methyl ester)pentanedioate ($R^{511}$ in general formula (V-1-1) is a methyl group)
bis(2-(carbamic acid butyl ester)ethyl)-2-(carbamic acid butyl ester)pentanedioate ($R^{511}$ in general formula (V-1-1) is a butyl group)
bis(2-(carbamic acid phenyl ester)ethyl)-2-(carbamic acid phenyl ester)pentanedioate ($R^{511}$ in general formula (V-1-1) is a phenyl group)

In general formula (V-1-1), m511=m512=m513=1, n511=n514=n516=2, n512=3, n513=2, n515=0 tris(2-(carbamic acid ethyl ester)ethyl)hexane-1,3,6-tricarboxylate ($R^{511}$ in general formula (V-1-1) is an ethyl group)

tris(2-(carbamic acid methyl ester)ethyl)hexane-1,3,6-tricarboxylate ($R^{511}$ in general formula (V-1-1) is a methyl group)

tris(2-(carbamic acid butyl ester)ethyl)hexane-1,3,6-tricarboxylate ($R^{511}$ in general formula (V-1-1) is a butyl group)

tris(2-(carbamic acid phenyl ester)ethyl)hexane-1,3,6-tricarboxylate ($R^{511}$ in general formula (V-1-1) is a phenyl group)

In general formula (V-1-1), m511=m513=0, m512=1, n512=4, n513=n515=0

An aliphatic carbamate represented by general formula (V-1-1-1) shown below (hereafter sometimes referred to as "the aliphatic carbamate (V-1-1-1)")

[Chemical formula 27]

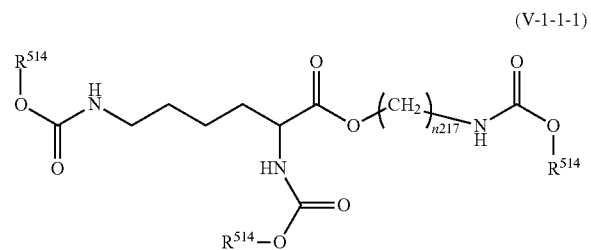

(V-1-1-1)

(In general formula (V-1-1-1), $R^{514}$ and n517 are the same as aforementioned $R^{41}$ and n217 respectively.)

Of the various possibilities, the aliphatic carbamate (V-1-1-1) is preferred as the compound (V-1-1).

Examples of preferred aliphatic carbamates (V-1-1-1) include the compounds listed below.

In general formula (V-1-1-1), n517=2

2,2-(carbamic acid methyl ester)ethyl-2,6-di(carbamic acid methyl ester)hexanoate ($R^{514}$ in general formula (V-1-1-1) is a methyl group)

2-(carbamic acid ethyl ester)ethyl-2,6-di(carbamic acid ethyl ester)hexanoate ($R^{514}$ in general formula (V-1-1-1) is an ethyl group)

2-(carbamic acid butyl ester)ethyl-2,6-di(carbamic acid butyl ester)hexanoate ($R^{514}$ in general formula (V-1-1-1) is a butyl group)

2-(carbamic acid phenyl ester)ethyl-2,6-di(carbamic acid phenyl ester)hexanoate ($R^{514}$ in general formula (V-1-1-1) is a phenyl group)

2-(dimethylphenyl carbamate)ethyl-2,6-di(dimethylphenyl carbamate)hexanoate ($R^{514}$ in general formula (V-1-1-1) is a dimethylphenyl group)

1-1-2) Compound (V-1-2)

The compound (V-1-2) is a compound represented by general formula (V-1-2) shown above.

One example of a preferred compound (V-1-2) is the compound represented by formula (V-1-2-1) shown below.

[Chemical formula 28]

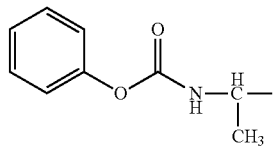
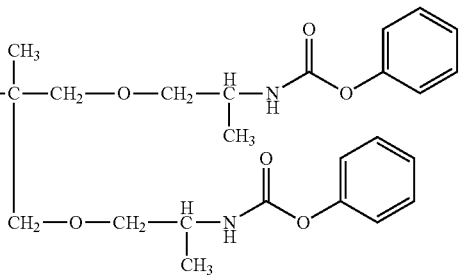

(V-1-2-1)

1-1-3) Compound (V-1-3)

The compound (V-1-3) is a compound represented by general formula (V-1-3) shown above.

Specific examples of preferred compounds (V-1-3) include 1,3,5-tri(carbamic acid methyl ester)benzene, 1,3,5-tri(carbamic acid methyl ester)-2-methylbenzene, 1,3,5-tris(1-(carbamic acid methyl ester)propan-2-yl)benzene, 1,3,5-tris(1-(carbamic acid methyl ester)propan-2-yl)-2-methylbenzene, 1,3,5-tris(1-(carbamic acid methyl ester)methyl)-2-methylbenzene, 2,2'-((2-(carbamic acid methyl ester)-1,3-phenylene)bis(methylene))bis((carbamic acid methyl ester)benzene), 1,3,5-tri(carbamic acid ethyl ester)benzene, 1,3,5-tri(carbamic acid ethyl ester)-2-methylbenzene, 1,3,5-tris(1-(carbamic acid ethyl ester)propan-2-yl)benzene, 1,3,5-tris(1-(carbamic acid ethyl ester)propan-2-yl)-2-methylbenzene, 1,3,5-tris(1-(carbamic acid ethyl ester)methyl)-2-methylbenzene, 2,2'-((2-(carbamic acid ethyl ester)-1,3-phenylene)bis(methylene))bis((carbamic acid ethyl ester)benzene), 1,3,5-tri(carbamic acid butyl ester)benzene, 1,3,5-tri(carbamic acid butyl ester)-2-methylbenzene, 1,3,5-tris(1-(carbamic acid butyl ester)propan-2-yl)benzene, 1,3,5-tris(1-(carbamic acid butyl ester)propan-2-yl)-2-methylbenzene, 1,3,5-tris(1-(carbamic acid butyl ester)methyl)-2-methylbenzene, 2,2'-((2-(carbamic acid butyl ester)-1,3-phenylene)bis(methylene))bis((carbamic acid butyl ester)benzene), 1,3,5-tri(carbamic acid phenyl ester)benzene, 1,3,5-tri(carbamic acid phenyl ester)-2-methylbenzene, 1,3,5-tris(1-(carbamic acid phenyl ester)propan-2-yl)benzene, 1,3,5-tris(1-(carbamic acid phenyl ester)propan-2-yl)-2-methylbenzene, 1,3,5-tris(1-(carbamic acid phenyl ester)methyl)-2-methylbenzene, 2,2'-((2-(carbamic acid phenyl ester)-1,3-phenylene)bis(methylene))bis((carbamic acid phenyl ester)benzene), 1,3,5-tri(carbamic acid dimethylphenyl ester)benzene, 1,3,5-tri(carbamic acid dimethylphenyl ester)-2-methylbenzene, 1,3,5-tris(1-(carbamic acid dimethylphenyl ester)propan-2-yl)benzene, 1,3,5-tris(1-(carbamic acid dimethylphenyl ester)propan-2-yl)-2-methylbenzene, 1,3,5-tris(1-(carbamic acid dimethylphenyl ester)methyl)-2-methylbenzene, and 2,2'-((2-(carbamic acid dimethylphenyl ester)-1,3-phenylene)bis(methylene))bis((carbamic acid dimethylphenyl ester)benzene).

1-2) Carbamate (V-2) and Carbamate (V-3)

Further, in those cases where the amino acid (II-2) described above or the amino acid ester (II-3) described above is used, a carbamate represented by general formula (V-2) shown below (hereafter sometimes referred to as "the carbamate (V-2)") or a carbamate represented by general formula (V-3) shown below (hereafter sometimes referred to as "the carbamate (V-3)") respectively is obtained.

[Chemical formula 29]

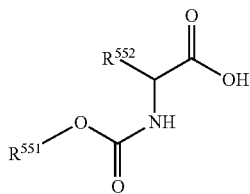
(V-2)

In general formula (V-2), $R^{551}$ is the same as $R^{41}$ described above. $R^{552}$ is a monovalent organic group that may include a group represented by general formula ((V-2)-1a) shown below (hereafter sometimes referred to as "the group ((V-2)-1a)").

[Chemical formula 30]

$R^{553}$—O—(C=O)—NH—        ((V-2)-1a)

In general formula ((V-2)-1a), $R^{553}$ is the same as $R^{41}$ described above.

[Chemical formula 31]

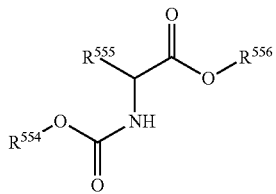
(V-3)

In general formula (V-3), $R^{554}$ and $R^{556}$ are the same as the aforementioned $R^{41}$ and $R^{253}$ respectively. $R^{555}$ is a monovalent organic group that may include a group represented by general formula ((V-3)-1a) shown below (hereafter sometimes referred to as "the group ((V-3)-1a)").

[Chemical formula 32]

$R^{557}$—O—(C=O)—NH—        ((V-3)-1a)

In general formula ((V-3)-1a), $R^{557}$ is the same as $R^{41}$ described above.

1-2-1) Carbamate (V-2)

The carbamate (V-2) is a compound represented by general formula (V-2) shown above.

($R^{552}$)

In general formula (V-2), $R^{552}$ is a monovalent organic group that may include a group represented by general formula ((V-2)-1a) shown below.

In the amino acid (II-2) that represents the raw material for the carbamate (V-2), in those cases where $R^{251}$ does not contain an amino group, $R^{552}$ does not include the above group ((V-2)-1a), and is the same as $R^{251}$ described above.

On the other hand, in the amino acid (II-2) that represents the raw material for the carbamate (V-2), in those cases where $R^{552}$ contains an amino group, that amino group reacts with the compound (IV) and undergoes a carbamation to form the group ((V-2)-a), and therefore $R^{552}$ is a monovalent organic group that includes the group ((V-2)-a). Examples of this monovalent organic group include the same groups as those exemplified above in relation to $R^{251}$.

One example of a preferred carbamate (V-2) is the compound represented by formula (V-2-1) shown below.

[Chemical formula 33]

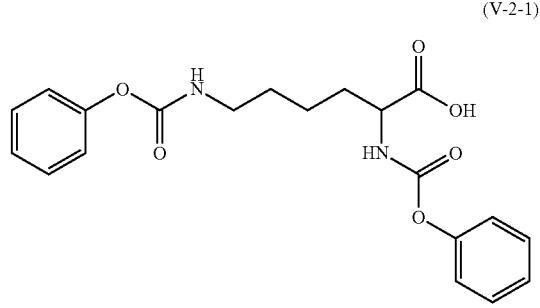
(V-2-1)

1-2-2) Carbamate (V-3)

The carbamate (V-3) is a compound represented by general formula (V-3) shown above.

($R^{555}$)

In general formula (V-3), $R^{555}$ is a monovalent organic group that may include a group represented by general formula ((V-3)-1a) shown below.

In the amino acid ester (II-3) that represents the raw material for the carbamate (V-3), in those cases where $R^{252}$ does not contain an amino group, $R^{555}$ does not include the above group ((V-3)-1a), and is the same as $R^{252}$ described above.

On the other hand, in the amino acid ester (II-3) that represents the raw material for the carbamate (V-3), in those cases where $R^{252}$ contains an amino group, that amino group reacts with the compound (IV) and undergoes a carbamation to form the group ((V-3)-1a), and therefore $R^{555}$ is a monovalent organic group that includes the group ((V-3)-1a). Examples of this monovalent organic group include the same groups as those exemplified above in relation to $R^{251}$.

Examples of preferred carbamates (V-3) include the compound represented by formula (V-3-1) shown below and the compound represented by formula (V-3-2) shown below.

[Chemical formula 34]

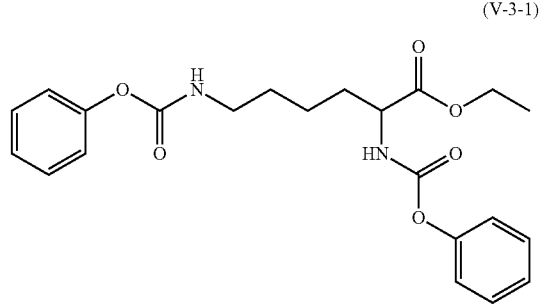
(V-3-1)

(V-3-2)

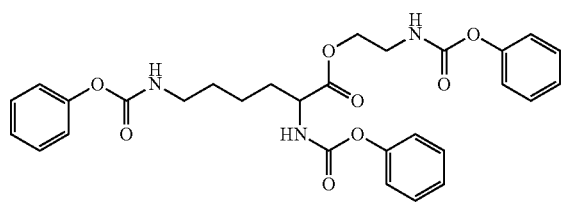

<<Method for Producing Isocyanate>>

By subjecting the carbamate obtained using the production method described above to a thermal decomposition reaction, an isocyanate can be produced. Preferred examples of the method for producing an isocyanate are described below.

The thermal decomposition reaction is a reaction that produces an isocyanate and a hydroxy compound from the isocyanate described above. This reaction is preferably conducted in the liquid phase. Examples of solvents that may be used include the same solvents as those exemplified above in relation to the aforementioned "step (1)".

The reaction temperature is typically within a range from at least 100° C. to not more than 300° C., and is preferably within a range from at least 150° C. to not more than 250° C. By ensuring that the reaction temperature is within this range, the reaction rate can be maintained at a high level, while side reactions of at least one of the carbamate and the product isocyanate can be more effectively prevented. In order to ensure a constant reaction temperature, at least one of a conventional cooling device and heating device may be fitted to the thermal decomposition reactor.

Further, the reaction pressure differs depending on the type of compound used and the reaction temperature, and may be a reduced pressure, normal pressure or pressurization, but is typically a value within a range from at least 1 Pa to not more than $1\times10^6$ Pa.

There are no particular limitations on the reaction time (the residence time in the case of a continuous reaction) but generally, the reaction time is preferably at least 0.001 hours but not more than 100 hours, more preferably at least 0.005 hours but not more than 50 hours, and more preferably at least 0.01 hours but not more than 10 hours.

There are no particular limitations on the type of thermal decomposition reactor used, but in order to enable efficient recovery of the gas phase components, the use of a conventional distillation apparatus is preferred, and an apparatus composed of at least one reactor selected from the group consisting of an evaporator, continuous multi-stage distillation tower, packed tower, thin-film evaporator and falling film evaporator is particularly preferred.

Various other conventional methods may also be used, including methods that employ a reactor including any of a distillation tower, multi-stage distillation tower, multi-tube reactor, reactor fitted with an internal support, forced circulation reactor, falling film evaporator or falling drop evaporator, or methods that use a combination of these devices. Among the various possibilities, a packed tower or tubular reactor is preferred, a tubular reactor is more preferred, and a tubular reactor such as a tubular thin-film evaporator or a tubular falling film evaporator is even more preferred. The internal structure of these reactors is preferably a structure that provides a large gas-liquid contact area that enables the low-boiling point products that are produced to migrate promptly into the gas phase.

Further, in those cases where a packed tower is used, the types of solid packing materials typically used in distillation towers and absorption towers may be used as appropriate for the solid packing material. Specific examples of preferred solid packing materials include Raschig rings, Lessing rings, spiral rings, Pall rings, Intalox saddles, Stedman packing, McMahon packing, Dixon packing, helix packing, coil packing and heat pipe packing. The material for the packing material is not limited to ceramic and metal materials. Of the various possibilities, the packing material used in the production method of the present embodiment is preferably a packing material formed from a material having high thermal conductivity.

The reactor used in the method for producing a carbamate described above and the thermal decomposition reactor may be of the same type or of different types, but the reactor used in the method for producing a carbamate described above and the thermal decomposition reactor are preferably at least one reactor selected from the group consisting of tower reactors and tank reactors.

The material used for the thermal decomposition reactor and lines may be selected from among conventional materials that have no adverse effects on the carbamate ester or the products thereof such as the isocyanate and the aromatic hydroxy compound, and for example, materials such as SUS304, SUS316 and SUS316L are inexpensive, and can be used favorably.

In the thermal decomposition reaction, although a catalyst is not necessarily required, a catalyst may be used for the purpose of lowering the reaction temperature or completing the reaction more rapidly.

The amount used of the catalyst is preferably at least 0.01% by mass but not more than 30% by mass, and more preferably at least 0.5% by mass but not more than 20% by mass, relative to the mass of the carbamate.

Examples of the catalyst include Lewis acids and transition metal compounds that generate Lewis acids, organotin compounds, compounds containing a copper group metal, compounds containing lead, compounds containing zinc, compounds containing an iron group metal, and amines.

Specific examples of the Lewis acids and transition metal compounds that generate Lewis acids include $AlX_3$, $TiX_3$, $TiX_4$, $VOX_3$, $VX_5$, $ZnX_2$, $FeX_3$ and $SnX_4$. Here, "X" represents a halogen, acetoxy group, alkoxy group or aryloxy group.

Specific examples of the organotin compounds include $(CH_3)_3SnOCOCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$ (dibutyltin dilaurate), $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnC_2$, $BuSnO(OH)$ and tin octylate. Here, "Bu" represents a butyl group, and "Ph" represents a phenyl group.

Specific examples of the compounds containing a copper group metal include $CuCl$, $CuCl_2$, $CuBr$, $CuBr_2$, $CuI$, $CuI_2$, $Cu(OAc)_2$, $Cu(acac)_2$, copper oleate, $Bu_2Cu$, $(CH_3O)_2Cu$, $AgNO_3$, $AgBr$, silver picrate, and $AgC_6H_6ClO_4$. Here, "acac" represents an acetylacetone chelate ligand.

Examples of the compounds containing lead include lead octylate and the like.

Examples of the compounds containing zinc include $Zn(acac)_2$ and the like.

Examples of the compounds containing an iron group metal include $Fe(C_{10}H_8)(CO)_5$, $Fe(CO)_5$, $Fe(C_4H_6)(CO)_3$, $Co(mesitylene)_2(PEt_2Ph_2)$, $CoC_5F_5(CO)_7$, and ferrocene.

Specific examples of the amines include 1,4-diazabicyclo[2,2,2]octane, triethylenediamine, and triethylamine.

Among these compounds, dibutyltin dilaurate, lead octylate or tine octylate is preferred as the catalyst. These catalysts may be used individually, or a combination of two or more catalysts may be used.

Further, the method for producing an isocyanate of the present embodiment may also include a "mixed liquid preparation step", a "low-boiling point decomposition product collection step", and a "high-boiling point component collection step" described below.

[Mixed Liquid Preparation Step]

This step is a step of mixing the carbamate obtained in the production method described above, and the catalyst and solvent and the like described above.

The solvent may be selected with various purposes, such as the purpose of dissolving the carbamate and transporting the carbamate to the thermal decomposition reactor, the purpose of suppressing recombination of the isocyanate and the hydroxy compound produced by the thermal decomposition, or the purpose of dissolving undecomposed carbamate or side reaction products derived from the carbamate or the isocyanate, and then extracting those compounds from the thermal decomposition reactor as a liquid-phase component.

The amount of the carbamate relative to the total mass of the mixed liquid is preferably at least 1% by mass but not more than 50% by mass, more preferably at least 3% by mass but not more than 40% by mass, and even more at least 5% by mass but not more than 30% by mass.

By ensuring that the amount of the carbamate relative to the total mass of the mixed liquid is at least as high as the above lower limit, the yield of the isocyanate can be increased, which is advantageous in the case of industrial implementation. Further, by ensuring that the amount is not more than the above upper limit, the occurrence of side reactions during the thermal decomposition reaction can be more effectively prevented.

[Low-Boiling Point Decomposition Product Collection Step]

This step is a step of continuously extracting, in a gaseous state, low-boiling point decomposition products produced by the thermal decomposition reaction of the carbamate, and components that have adopted a gaseous state under the thermal decomposition reaction conditions in the thermal decomposition reactor, such as the solvent and the like. Here, the "low-boiling point decomposition products" preferably includes at least one of the isocyanate and the hydroxy compound produced by the thermal decomposition reaction of the carbamate, and more preferably include both the hydroxy compound and the isocyanate.

In order to collect these components in a gaseous state, the conditions such as the temperature and pressure under which this step is conducted are preferably set in accordance with the compounds used and the compounds produced by the thermal decomposition of the carbamate.

Further, in order to enable the collection of the low-boiling point decomposition products to be conducted promptly, a carrier agent may also be introduced. Examples of this type of carrier agent include inert gases and hydrocarbon gases and the like. Examples of the inert gases include nitrogen, argon, helium, carbon dioxide gas, methane, ethane and propane.

Low-boiling point organic solvents may also be used with similar effect. Examples of these low-boiling point organic solvents include halogenated hydrocarbons, lower hydrocarbons, and ethers and the like. Specific examples of the halogenated hydrocarbons include dichloromethane, chloroform and carbon tetrachloride. Examples of the lower hydrocarbons include pentane, hexane, heptane and benzene. Examples of the ethers include tetrahydrofuran and dioxane.

These carrier agents may be used individually, or a mixture of two or more carrier agents may be used. Further, these carrier agents are preferably heated prior to use.

The gaseous components such as the gaseous low-boiling point decomposition products collected from the thermal decomposition reactor may be introduced without further modification into a cooler, enabling a portion or all of the components to be collected in a liquid state. Further, the gaseous components may be supplied to a distillation tower for purification and separation, either in a gaseous state, or in a liquid state obtained upon introduction into a cooler.

[High-Boiling Point Component Collection Step]

In the high-boiling point component collection step, the liquid phase components that were not collected as gaseous components in the aforementioned low-boiling point decomposition product collection step are continuously extracted from the reactor and collected. The high-boiling point components collected in this step often contain side reaction products of the carbamate with the isocyanate produced by the thermal decomposition of the carbamate, side reaction products of the isocyanate, side reaction products of the carbamate, and compounds produced by further reaction of these side reaction products. Further, in those cases where a solvent is used that exists in a liquid state under the thermal decomposition reaction conditions (hereafter sometimes referred to as a "high-boiling point solvent"), the collected high-boiling point components will often also contain this high-boiling point solvent. The high-boiling point components often adhere to the surfaces of the reactor, causing blockages and the like, and therefore by continuously collecting these high-boiling point components from the thermal decomposition reactor as liquid phase components, a preventative effect on this adhesion to the reactor surfaces can be achieved.

The mixed liquid preparation step, the low-boiling point decomposition product collection step, and the high-boiling point component collection step described above may be performed separately using a plurality of devices, or may be performed simultaneously using a single device.

EXAMPLES

Embodiments of the present invention are described below in more detail using specific examples and comparative examples, but provided they do not exceed the scope of the invention, embodiments of the present invention are in no way limited by the following examples and comparative examples.

<Reference: Analytical Methods>

(1) NMR Analysis Method

Apparatus: JNM-A400 FT NMR system, manufactured by JEOL Ltd.

Preparation of Samples for 1H and 13C-NMR Analysis

Approximately 0.3 g of a sample solution was weighed, and approximately 0.7 g of deuterated chloroform (manufactured by Aldrich Corporation, United States, 99.8%) and 0.05 g of tetramethyltin as an internal standard (manufactured by Wako Pure Chemical Industries, Ltd., Japan, Wako first grade) were then added to the sample solution and mixed uniformly to obtain an NMR analysis sample.

Quantitative Analysis Method

Each of a series of standard substances was analyzed to prepare a calibration curve, and quantitative analysis of the analysis sample solution was conducted based on the calibration curve.

(2) Liquid Chromatography Analysis Method

Apparatus: LC-10AT system, manufactured by Shimadzu Corporation, Japan.

Column: two Inertsil-ODS columns, manufactured by GL Sciences Inc., Japan, were connected in series.

Eluent: a mixed liquid of a 5 mmol/L aqueous solution of ammonium acetate (A liquid) and acetonitrile (B liquid)

Eluent flow rate: 2 mL/minute

Column temperature: 35° C.

Detector: R.I. (Refractometer) and PDA detector (photodiode array detector, measurement wavelength range: 200 nm to 300 nm)

Liquid Chromatography Analysis Sample

Approximately 0.1 g of a sample was weighed, and approximately 1 g of tetrahydrofuran (manufactured by Wako Pure Chemical Industries, Ltd., Japan, anhydrous) and approximately 0.02 g of 1,1-diethyl urea (manufactured by Tokyo Chemical Industry Co., Ltd., Japan) as an internal standard were then added to the sample and mixed uniformly to obtain a liquid chromatography analysis sample.

Quantitative Analysis Method

Each of a series of standard substances was analyzed to prepare a calibration curve, and quantitative analysis of the analysis sample solution was conducted based on the calibration curve.

(3) Thermal Dissociation Temperature Measurement Method

Apparatus: TG/DTA Analyzer TG8120, manufactured by Rigaku Corporation, Japan.

MS analyzer: GCMS-QP 2010 plus, manufactured by Shimadzu Corporation, Japan.

Atmosphere: helium

Rate of temperature increase: 10° C./minute

Measurement temperature range: room temperature (about 25° C.) to 400° C.

Analysis Method

A sample (approximately 5 mg) was heated under the above measurement conditions, and the generated gas was analyzed using the MS analyzer. The temperature at which compounds containing an $NH_2$ group produced by decomposition of a urea linkage were detected was deemed the compound thermal dissociation temperature.

Example 1

(Production Step for Compound Having Urea Linkage Using Carbon Dioxide)

First, 120 g (1.03 mol) of 1,6-hexamethylenediamine was placed in a 3 L SUS316L autoclave, and following sealing of the autoclave, a process of raising the pressure of carbon dioxide in the gas phase to 1 MPa (absolute pressure) and then reducing the pressure to normal pressure was repeated three times to replace the gas phase. The internal temperature was then heated to 210° C., carbon dioxide was fed into the autoclave to increase the total pressure to 8 MPa, stirring under heating was continued for 12 hours with the pressure held at 8 MPa, and the reactor was then returned to room temperature and normal pressure. Analysis of the component obtained following the reaction by JR (KBr method) confirmed absorptions at 1620 $cm^{-1}$ (C=O stretch) and 1570 $cm^{-1}$ (NH stretch), confirming a conversion to a compound having a urea linkage. Quantitative analysis by liquid chromatography revealed a conversion rate from the raw material amine of 87%. Further, when the solvent was removed by distillation from the reaction liquid obtained as a sample, and the remaining residue was measured by TG/DTA analysis, the thermal dissociation temperature of the produced component containing the urea conjugate was 220° C.

(Production Step for Carbamate)

The composition containing the compound having a urea linkage produced in the step described above was transferred to a 2 L four-neck flask fitted with a stirrer, 950 g of ortho-dichlorobenzene as a solvent and 224 g (1.05 mol) of diphenyl carbonate, an amount equimolar with the produced urea conjugate, were added to the flask, and the resulting mixture was reacted at 80° C. for 10 hours. The reaction liquid was sampled, and analysis by liquid chromatography revealed that the target N,N'-hexanediyl-bis-carbamic acid diphenyl ester (hereafter referred to as "the carbamate") had been produced. Hydrochloric acid with a concentration of 1 mol/L was added to the reaction liquid and stirred, and the organic layer was then collected and washed with ion-exchanged water. The ortho-dichlorobenzene was removed from the organic layer by distillation using a rotary evaporator, and analysis of the thus obtained solid by $^1$H-NMR confirmed the target carbamate (purity: 99%). The yield of the carbamate relative to the raw material amine was 92%.

(Mixed Solution Preparation Step)

A mixed solution was prepared from 10% by weight of the carbamate obtained in the step described above and 90% by weight of ortho-dichlorobenzene.

(Reaction Mixture Production Step, Decomposition Step, Low-Boiling Point Decomposition Product Collection Step, and High-Boiling Point Solvent Collection Step)

The mixed solution obtained above was introduced continuously into a thermal decomposition reactor illustrated in FIG. 1. Specifically, first, a raw material preheater 1 was preheated to 160° C., and the mixed solution was fed through the raw material preheater 1 and introduced into the upper portion of a tubular first reactor 2 at a continuous flow rate of 600 g/hr.

The tubular first reactor 2 had an internal diameter of 5 cm, included a distributor for uniformly distributing the raw material mixture introduced from the upper portion, and was packed with Raschig rings made of stainless steel. Further, in the packing layer, a liquid redistributor was provided every 15 cm.

The reaction mixture extracted from the lower portion of the tubular first reactor 2 was introduced continuously at a flow rate of 600 g/hr into a second reactor 3 composed of a tank reactor. At this time, dry nitrogen gas that had been preheated to 250° C. was introduced continuously at a rate of 200 NL/hr as a carrier agent into the liquid in the second reactor 3.

The tubular first reactor 2 and the tank-like second reactor 3 were both held at a temperature of 250° C., and at a pressure of 8 kg/cm$^2$.

The average residence time of the reaction liquid was 20 minutes in the tubular first reactor 2 and 15 minutes in the tank-like second reactor.

The vapor of phenol and ortho-dichlorobenzene exiting the tank-like second reactor 3 was extracted from the bottom of the reaction tube together with the nitrogen gas carrier agent, and introduced into the tubular first reactor 2.

The gaseous component discharged from the top of the tubular first reactor 2 was passed through a partial condenser 4 held at 150° C., thereby separating the gaseous component into a liquid component composed mostly of ortho-dichlorobenzene, and a gaseous component composed of phenol vapor and nitrogen gas containing a small amount of ortho-dichlorobenzene vapor.

The liquid component separated by the partial condenser 4 was returned without modification to the upper portion of the tubular first reactor 2, whereas the gaseous component was introduced into a cooler and separated continuously into a liquid component composed of phenol containing a small amount of ortho-dichlorobenzene, and nitrogen gas.

Further, an ortho-dichlorobenzene solution containing hexamethylene diisocyanate was extracted continuously from the lower portion of the tank-like second reactor 3. Once the reaction had reached a normal state, the ortho-dichlorobenzene solution was analyzed, and the result revealed that no undecomposed carbamate or reaction intermediates existed, and that hexamethylene diisocyanate had been produced with a selectivity of 86%.

Examples 2 to 10

With the exception of altering the raw material amine used to each of the amines shown in the "amine" column of Table 1 and Table 2, the same operations as Example 1 were conducted, obtaining the corresponding carbamates and isocyanates shown in Table 1 and Table 2.

TABLE 1

| | Raw materials for amine compound production | | | Production of compound having urea linkage | | | | | | | |
|---|---|---|---|---|---|---|---|---|---|---|---|
| | Amino acid amino acid derivative | Amino acid structural formula | Alkanol-amine/ alcohol | Production raw materials for compound having urea linkage | | | | Water extraction during production of compound having urea linkage | Thermal dissociation temperature | Reaction temperature | Raw material amine conversion rate |
| | | | | Amine | Carbonyl source | Equivalence relative to amine terminals | Solvent | | | | |
| Example 1 | — | — | — | H₂N–(CH₂)₆–NH₂ | CO₂ | — | — | — | 220 | 200 | 87 |
| Example 2 | — | — | — | H₂N–(CH₂)₅–NH₂ | CO₂ | — | — | — | 215 | 200 | 84 |
| Example 3 | — | — | — | isophorone diamine | CO₂ | — | — | — | 220 | 200 | 83 |
| Example 4 | — | — | — | 4,4'-methylenedianiline | CO₂ | — | — | — | 220 | 200 | 85 |
| Example 5 | — | — | — | 4,4'-methylenebis(cyclohexylamine) | CO₂ | — | — | — | 210 | 220 | 84 |
| Example 6 | — | — | — | m-xylylenediamine | CO₂ | — | — | — | 215 | 200 | 84 |
| Example 7 | — | — | — | 1,2-bis(aminomethyl)cyclohexane | CO₂ | — | — | — | 220 | 220 | 82 |

TABLE 1-continued

| | | | Production of carbamate | | Production of isocyanate by thermal decomposition of carbamate | |
|---|---|---|---|---|---|---|
| | Carbonate ester | Required carbonate ester equivalence relative to urea conjugate | Obtained carbamate | Carbamate yield | Obtained isocyanate | Thermal decomposition yield (%) |
| Example 8 | — | — | H₂N-C₆H₃(CH₃)-NH₂ (2,4-diaminotoluene) | — | CO₂ 225, 200, 85 | — |
| Example 1 | DPC | 0.5 | PhO-C(O)-NH-(CH₂)₆-NH-C(O)-OPh | 92 | OCN-(CH₂)₆-NCO | 86 |
| Example 2 | DPC | 0.5 | PhO-C(O)-NH-(CH₂)₅-NH-C(O)-OPh | 88 | OCN-(CH₂)₅-NCO | 86 |
| Example 3 | DPC | 0.5 | IPDI-dicarbamate (PhO-C(O)-NH-CH₂- and -NH-C(O)-OPh on trimethylcyclohexyl) | 90 | IPDI (OCN-CH₂- and -NCO on trimethylcyclohexyl) | 81 |
| Example 4 | DPC | 0.5 | PhO-C(O)-NH-C₆H₄-CH₂-C₆H₄-NH-C(O)-OPh | 92 | OCN-C₆H₄-CH₂-C₆H₄-NCO | 84 |

TABLE 1-continued

| Example | | | | Structure (carbamate) | Yield | Structure (isocyanate) | Yield |
|---|---|---|---|---|---|---|---|
| Example 5 | DPC | 0.5 | 86 | (dicyclohexylmethane bis-phenyl carbamate) | | (dicyclohexylmethane diisocyanate, H12MDI) | 83 |
| Example 6 | DPC | 0.5 | 89 | (m-xylylene bis-phenyl carbamate) | | (m-xylylene diisocyanate) | 82 |
| Example 7 | DPC | 0.5 | 91 | (1,2-bis(phenoxycarbonylaminomethyl)cyclohexane) | | (1,2-bis(isocyanatomethyl)cyclohexane) | 83 |
| Example 8 | DPC | 0.5 | 89 | (2,4-toluene bis-phenyl carbamate) | | (2,4-toluene diisocyanate, TDI) | 84 |

TABLE 2

| | Raw Materials for amine compound production | | Production raw materials for compound having urea linkage | | | Production of compound having urea linkage | | | | |
|---|---|---|---|---|---|---|---|---|---|---|
| | Amino acid/amino acid derivative | Amino acid structural formula | Alkanolamine/alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 9 | — | — | — | (branched diamine structure) | $CO_2$ | — | — | — | 225 | 200 | 86 |
| Example 10 | — | — | — | (methacrylate ester with amine) | $CO_2$ | — | — | — | 215 | 200 | 89 |
| Example 11 | — | — | — | (diamine structure) | $CO_2$ | — | — | — | 220 | 200 | 98 |
| Example 12 | lysine | (lysine structure) | monoethanolamine | (lysine monoethanolamine ester) | $CO_2$ | — | — | water extracted three times | 240 | 200 | 85 |
| Example 13 | alanine | (alanine structure) | monoethanolamine | (alanine monoethanolamine ester) | $CO_2$ | — | — | — | 245 | 200 | 82 |

TABLE 2-continued

| | | | | | |
|---|---|---|---|---|---|
| Example 14 | arginine ![arginine structure] | mono ethanol-amine $H_2N$~~~$NH_2$ | $CO_2$ | — | 225 | 200 | 81 |
| Example 15 | aspartic acid ![aspartic acid structure] | mono ethanol-amine | $CO_2$ | — | 245 | 200 | 85 |

Production of carbamate | Production of isocyanate by thermal decomposition of carbamate

| | Carbonate ester | Required carbonate ester equivalence relative to urea conjugate | Carbamate yield | Obtained carbamate | Obtained isocyanate | Thermal decomposition yield (%) |
|---|---|---|---|---|---|---|
| Example 9 | DPC | 0.5 | 92 | [structure with PhO-C(O)-NH- groups, branched] | [structure with NCO and OCN groups, branched] | 81 |
| Example 10 | DPC | 0.5 | 91 | [methacrylate carbamate structure with OPh] | [methacrylate isocyanate structure with NCO] | 82 |
| Example 11 | DPC | 0.5 | 92 | [linear carbamate structure with OPh and PhO] | [linear diisocyanate structure] | 85 |

TABLE 2-continued

| Example | | | | | |
|---|---|---|---|---|---|
| Example 12 | DPC | 0.5 | 92 | (structure) | 79 |
| Example 13 | DPC | 0.5 | 91 | (structure) | 81 |
| Example 14 | DPC | 0.5 | 90 | (structure) | 83 |
| Example 15 | DPC | 0.5 | 94 | (structure) | 82 |

Example 11

(Production Step for Compound having Urea Linkage using Carbon Dioxide)

First, 120 g (1.03 mol) of 1,6-hexamethylenediamine was placed in a 3 L SUS316L autoclave, and following sealing of the autoclave, a process of raising the pressure of carbon dioxide in the gas phase to 1 MPa (absolute pressure) and then reducing the pressure to normal pressure was repeated three times to replace the gas phase. The internal temperature was then heated to 240° C., and carbon dioxide was fed into the autoclave to increase the total pressure to 8 MPa. Stirring under heating was conducted with the pressure held at 8 MPa, and on a total of three occasions after 3 hours, 6 hours and then 9 hours, the reactor pressure was reduced to normal pressure, the by-product water was removed from the system by distillation, and the total pressure was then returned to 8 MPa with carbon dioxide. After stirring under heating for 12 hours, the pressure inside the reactor was reduced. Analysis of the component obtained following the reaction by JR (KBr method) confirmed absorptions at 1620 cm$^{-1}$ (C=O stretch) and 1570 cm$^{-1}$ (NH stretch). Quantitative analysis by NMR revealed a conversion rate of the raw material amine of 98%. The steps subsequent to the carbamate production step were conducted in the same manner as Example 1, yielding the corresponding isocyanate shown in Table 2.

Example 12

(Synthesis of Lysine β-Aminoethyl Ester Trihydrochloride)

A 1 L four-neck flask fitted with a stirrer was charged with 313 g (3.0 mol) of 35% by weight hydrochloric acid, and with the flask cooled in an ice bath, 122 g (2.0 mol) of ethanolamine was added gradually in a dropwise manner to the flask. Subsequently, 183 g (1.0 mol) of lysine monohydrochloride was added. The pressure inside the reaction flask was reduced to 4 kPa, and the temperature of the reaction liquid was heated to 110° C. and 200 g of water was removed from the reaction liquid by distillation.

With the reaction flask held at a pressure of 4 kPa and the reaction liquid temperature maintained at 110° C., xylene gas at 4 kPa that had been heated to 110° C. with a preheater was supplied from beneath the reaction liquid. The flow rate of the xylene gas was 18 g/hr. While the xylene gas was being supplied, xylene and water were removed from the reaction system by distillation, and the water content of the reaction liquid was reduced to not more than 0.4% by weight.

The thus obtained reaction liquid was placed in a 500 mL flask fitted with a stirrer, the temperature of the reaction liquid was adjusted to 110° C., and under normal pressure conditions, hydrogen chloride gas was supplied to the flask in an amount of 1.0% by weight of the weight of the reaction liquid.

The step A described above was repeated a further two times, yielding a reaction liquid with an esterification rate of 80%.

The esterification rate was calculated using the following formula.

Esterification rate (%)=$M1/M2 \times 100$

In the above formula, M1 represents the number of moles of the produced lysine β-aminoethyl ester trihydrochloride (a value quantified by analysis by high-performance liquid chromatography), and M2 represents the number of moles of the lysine monohydrochloride used as a raw material.

A mixed liquid of 720 g of methanol and 480 g of ortho-dichlorobenzene was added to dissolve the product, and a small amount of seed crystals was added to promote crystallization. The resulting solid was collected by filtration, and a mixed liquid of methanol/ortho-dichlorobenzene having the same composition as that used during the crystallization was used to wash the solid, which was then collected by filtration. The solid was dried using a reduced-pressure dryer, and subsequent analysis by liquid chromatography confirmed the formation of lysine β-aminoethyl ester trihydrochloride.

(Production Step for Compound Having Urea Linkage Using Carbon Dioxide)

With the exceptions of using the ester obtained in the step described above, and altering the heating temperature and time to 140° C. and 15 hours respectively, the same operations as Example 1 were conducted to obtain a compound having a urea linkage.

(Production Step for Carbamate—Reaction Mixture Production Step, Decomposition Step, Low-Boiling Point Decomposition Product Collection Step and High-Boiling Point Solvent Collection Step)

With the exception of using the compound having a urea linkage obtained in the step described above, the same operations as Example 1 were conducted, obtaining the corresponding carbamate and isocyanate shown in Table 2.

Examples 13 to 24

With the exception of replacing the amino acid and the alcohol used during synthesis of the amino acid ester that were used in Example 13 with each of the amino acids (shown in the column labeled "Amino acid structural formula" in Tables 3 and 4) and alcohols (shown in the column labeled "Alkanolamine/alcohol" in Tables 3 and 4) listed in Tables 2 to 4, the same operations as Example 1 were conducted, obtaining the corresponding carbamates and isocyanates shown in Tables 2 to 4. In the case where arginine was used, the arginine was hydrolyzed using a conventional method to form ornithine prior to use. Further, in the cases where glutamine or asparagine was used, a conventional method was used to hydrolyze the glutamine or asparagine to form glutamic acid or aspartic acid respectively prior to use.

TABLE 3

| | Raw materials for amine compound production | | | Production of compound having urea linkage | | | | | | |
|---|---|---|---|---|---|---|---|---|---|---|
| | Amino acid/amino acid derivative | Amino acid structural formula | Alkanolamine/alcohol | Production raw materials for compound having urea linkage | | | | Water extraction | Thermal dissociation temperature | Reaction temperature | Raw material amine conversion rate |
| | | | | Amine | Carbonyl source | Equivalence relative to amine terminals | Solvent | during production of compound having urea linkage | | | |
| Example 16 | glutamic acid | (structure: glutamic acid) | monoethanolamine | (structure: diester diamine from glutamic acid and ethanolamine) | CO$_2$ | — | — | — | 260 | 200 | 83 |
| Example 17 | glycine | (structure: glycine) | monoethanolamine | (structure: glycine ethanolamine ester) | CO$_2$ | — | — | — | 250 | 200 | 84 |
| Example 18 | synthetic amino acid | — | monoethanolamine | (structure: furan amino methyl ester) | CO$_2$ | — | — | — | 240 | 200 | 82 |
| Example 19 | lysine | (structure: lysine) | EtOH | (structure: lysine ethyl ester) | CO$_2$ | — | — | — | 255 | 200 | 84 |

TABLE 3-continued

| | | | | | | | |
|---|---|---|---|---|---|---|---|
| Example 20 | lysine ![lysine structure] | 1-amino-2-PrOH ![1-amino-2-PrOH structure] | CO$_2$ | — | — | 240 | 200 | 82 |

| | | Production of carbamate | | | Production of isocyanate by thermal decomposition of carbamate | |
|---|---|---|---|---|---|---|
| | Carbonate ester | Required carbonate ester equivalence relative to urea conjugate | Carbamate yield | Obtained carbamate | Obtained isocyanate | Thermal decomposition yield (%) |
| Example 16 | DPC | 0.5 | 95 |  | 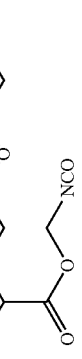 | 79 |
| Example 17 | DPC | 0.5 | 93 | 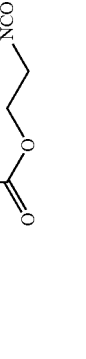 |  | 77 |

TABLE 3-continued

| | | | | | |
|---|---|---|---|---|---|
| Example 18 | DPC | 0.5 | 92 | [structure: methyl 2-(furan-2-yl)-2-((phenoxycarbonyl)amino)acetate] | 74 [structure: methyl 2-(furan-2-yl)-2-isocyanatoacetate] |
| Example 19 | DPC | 0.5 | 90 | [structure: ethyl 2,6-bis((phenoxycarbonyl)amino)hexanoate] | 75 [structure: ethyl 2,6-diisocyanatohexanoate] |
| Example 20 | DPC | 0.5 | 88 | [structure: 1-(((phenoxycarbonyl)amino)ethyl) 2,6-bis((phenoxycarbonyl)amino)hexanoate] | 78 [structure: 1-isocyanatoethyl 2,6-diisocyanatohexanoate] |

TABLE 4

| | Raw materials for amine compound production | | Production raw materials for compound having urea linkage | Production of compound having urea linkage | | | | | |
|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 21 | lysine | (structure) | 2-amino-1-BuOH | (structure) | $CO_2$ | — | — | — | 250 | 200 | 83 |
| Example 22 | glutamic acid | (structure) | EtOH | (structure) | $CO_2$ | — | — | — | 240 | 200 | 79 |
| Example 23 | glutamic acid | (structure) | 1-amino-2-PrOH | (structure) | $CO_2$ | — | — | — | 250 | 200 | 78 |

TABLE 4-continued

| | glutamic acid | | 2-amino-1-BuOH | $CO_2$ | | | | |
|---|---|---|---|---|---|---|---|---|
| Example 24 | (structure: glutamic acid with H₂N, OH, O, OH) | | | | (structure: diester of glutamic acid with 2-amino-1-butanol groups, H₂N-, -NH₂) | — | 260 | 200 | 76 |

| | | Production of carbamate | | Production of isocyanate by thermal decomposition of carbamate | |
|---|---|---|---|---|---|
| | Carbonate ester | Required carbonate ester equivalence relative to urea conjugate | Carbamate yield | Obtained carbamate | Obtained isocyanate | Thermal decomposition yield (%) |
| Example 21 | DPC | 0.5 | 89 | (carbamate structure with Ph-O-C(O)-NH- groups on lysine-type backbone with ester linkage) | (isocyanate structure with NCO and OCN groups) | 76 |
| Example 22 | DPC | 0.5 | 91 | (diethyl glutamate bis-phenyl carbamate structure) | (diethyl 2-isocyanatoglutarate structure) | 75 |

TABLE 4-continued
| Example | | | | |
|---|---|---|---|---|
| Example 23 | DPC | 0.5 | 93 | 72 |
| Example 24 | DPC | 0.5 | 92 | 76 |
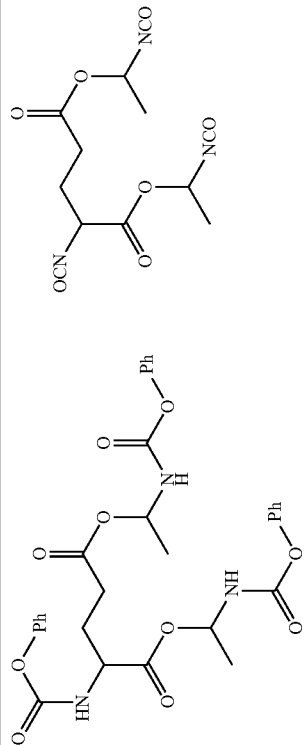
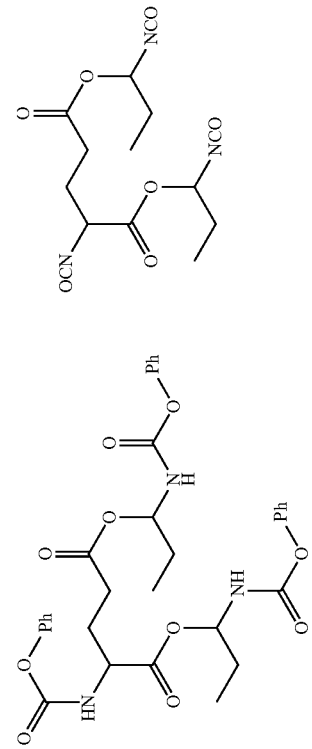
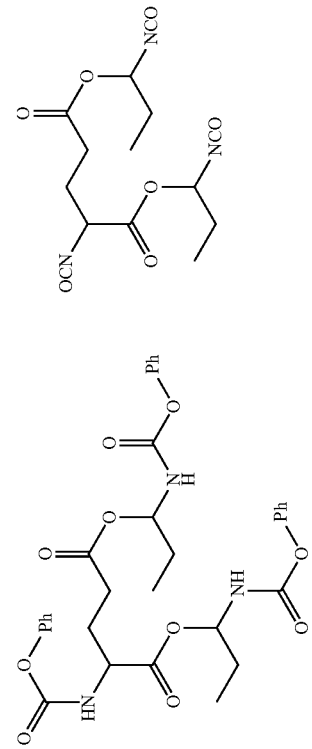
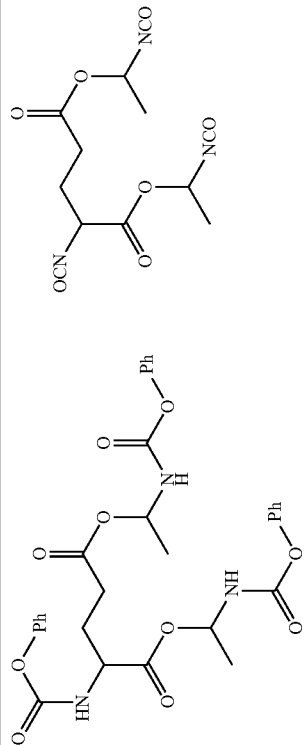

Example 25

(Production Step for Compound having Urea Linkage using Carbon Dioxide)

First, 183 g (1.0 mol) of lysine monohydrochloride was placed in a 3 L SUS316L autoclave, and following sealing of the autoclave, a process of raising the pressure of carbon dioxide in the gas phase to 1 MPa (absolute pressure) and then reducing the pressure to normal pressure was repeated three times to replace the gas phase. Subsequently, 1,100 g of anhydrous 2,5-dimethylphenol was added as a solvent, the internal temperature was heated to 140° C., and carbon dioxide was fed into the autoclave to increase the total pressure to 8 MPa. Stirring under heating was continued for 12 hours with the pressure held at 8 MPa, and the reactor was then returned to room temperature and normal pressure. The solvent was removed from the reaction mixture using a rotary evaporator to obtain a dry solid, and analysis of the component contained in the residue following the reaction by IR (KBr method) confirmed absorptions at 1,620 cm$^{-1}$ (C=O stretch) and 1,570 cm$^{-1}$ (NH stretch), confirming conversion to a compound having a urea linkage in which the amino group of lysine had been converted to a urea linkage. Quantitative analysis by NMR revealed a conversion rate of the raw material amine of 74%.

(Synthesis of Lysine Ester Having Urea Linkage)

A 1 L four-neck flask fitted with a stirrer was charged with 261 g (2.5 mol) of 35% by weight hydrochloric acid, and the composition having a urea linkage synthesized above (in an amount equivalent to 1.0 mol relative to the raw material lysine hydrochloride) and 230 g (5.0 mol) of anhydrous ethanol were then added gradually to the flask. The temperature inside the reaction flask was held at 50° C. for two hours, and with the pressure inside the system then held at 25 kPa, solvent containing an equivalent of 109 g of water was removed from the reaction liquid by water-ethanol azeotropic distillation.

The thus obtained reaction liquid was placed in a 500 mL flask fitted with a stirrer, the temperature of the reaction liquid was adjusted to 80° C., and under normal pressure conditions, hydrogen chloride gas was supplied to the flask in an amount of 1.0% by weight of the weight of the reaction liquid, thus obtaining a reaction liquid with an esterification rate of 85%.

A mixed liquid of 600 g of methanol and 350 g of ortho-dichlorobenzene was added to dissolve the product, and a small amount of seed crystals was added to promote crystallization. The resulting solid was collected by filtration, and a mixed liquid of methanol/ortho-dichlorobenzene having the same composition as that used during the crystallization was used to wash the solid, which was then collected by filtration. The solid was dried using a reduced-pressure dryer, and subsequent analysis by liquid chromatography confirmed the formation of lysine ethyl ester dihydrochloride having a urea linkage.

(Production Step for Carbamate—Reaction Mixture Production Step, Decomposition Step, Low-Boiling Point Decomposition Product Collection Step and High-Boiling Point Solvent Collection Step)

With the exception of using the compound having a urea linkage obtained in the step described above, the same operations as Example 1 were conducted, obtaining the corresponding carbamate and isocyanate shown in Table 5.

Example 26

With the exception of replacing the lysine monohydrochloride used in Example 25 with an equimolar amount of ornithine, the same operations as Example 25 were conducted, obtaining the corresponding carbamate and isocyanate shown in Table 5.

Example 27

(Production Step for Compound having a Urea Linkage using a Carbonic Acid Derivative)

First, 120 g (1.03 mol) of 1,6-hexamethylenediamine and 60.5 g (1.00 mol) of urea were placed in a 3 L four-neck flask, and the gas phase was replaced with nitrogen. At this time, the molar ratio of urea relative to the amino groups in the added raw material was 0.488. Next, 1,100 g of anhydrous 2,5-dimethylphenol was added, the internal temperature was adjusted to 140° C. and the internal pressure was adjusted to 50 kPa. The reaction was continued for 15 hours, while the by-product ammonia was removed from the system by distillation, and the reactor was then returned to room temperature and normal pressure. Analysis of the component obtained following the reaction by IR (KBr method) confirmed absorptions at 1,618 cm$^{-1}$ (C=O stretch) and 1,571 cm$^{-1}$ (NH stretch). Quantitative analysis by NMR revealed a conversion rate from the raw material amine of 81%.

(Production Step for Carbamate)

The composition containing the compound having a urea linkage produced in the step described above was transferred to a 2 L four-neck flask fitted with a stirrer, 950 g of ortho-dichlorobenzene as a solvent and 209 g (0.98 mol) of diphenyl carbonate, an amount equimolar with the produced urea conjugate, were added to the flask, and the resulting mixture was reacted at 80° C. for 10 hours. The reaction liquid was sampled, and analysis by liquid chromatography revealed that the target carbamate had been produced in a yield of 88% relative to the raw material urea conjugate. Hydrochloric acid with a concentration of 1 mol/L was added to the reaction liquid and stirred, and the organic layer was then collected and washed with ion-exchanged water. The ortho-dichlorobenzene was removed from the organic layer by distillation using a rotary evaporator, and analysis of the thus obtained solid by H-NMR confirmed the target carbamate (purity: 99%). The yield of the carbamate relative to the raw material amine was 88%.

(Reaction Mixture Production Step, Decomposition Step, Low-Boiling Point Decomposition Product Collection Step and High-Boiling Point Solvent Collection Step)

Using the carbamate obtained from the above operations, the same operations as Example 1 were conducted, obtaining the corresponding isocyanate shown in Table 5.

Examples 28 to 36

With the exception of altering the raw material amine used to each of the amines shown in Tables 5 and 6, the same operations as Example 27 were conducted, obtaining the corresponding carbamates and isocyanates shown in Tables 5 and 6. In each case, the molar ratio of urea relative to the amino groups in the added raw material was the same as Example 27.

TABLE 5

| | Raw materials for amine compound production | | | Production raw materials for compound having urea linkage | | | | Water extraction during production of compound having urea linkage | Thermal dissociation temperature | Reaction temperature | Raw material amine conversion rate |
|---|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | | | | |
| Example 25 | — | — | — |  | $CO_2$ | — | — | — | 250 | 140 | 74 |
| Example 26 | — | — | — |  | $CO_2$ | — | — | — | 245 | 140 | 70 |
| Example 27 | — | — | — |  | urea | 0.488 | 2,5-DMPhOH | — | 220 | 140 | 81 |
| Example 28 | — | — | — | 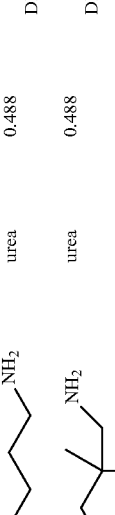 | urea | 0.488 | 2,5-DMPhOH | — | 215 | 140 | 79 |
| Example 29 | — | — | — |  | urea | 0.488 | 2,5-DMPhOH | — | 220 | 140 | 80 |
| Example 30 | — | — | — | 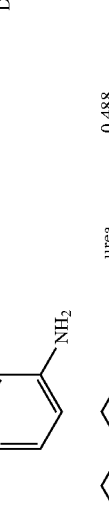 | urea | 0.488 | 2,5-DMPhOH | — | 220 | 140 | 78 |
| Example 31 | — | — | — |  | urea | 0.488 | 2,5-DMPhOH | — | 210 | 140 | 77 |

TABLE 5-continued

| Example | Carbonate ester | Required carbonate ester equivalence relative to urea conjugate | Production of carbamate | | Production of isocyanate by thermal decomposition of carbamate | | | |
|---|---|---|---|---|---|---|---|---|
| | | | Carbamate yield | Obtained carbamate | urea | 2,5-DMPhOH | Obtained isocyanate | Thermal decomposition yield (%) |
| Example 32 | — | — | — | (m-xylylenediamine, NH₂-CH₂-C₆H₄-CH₂-NH₂) | 0.488 | — | 215 140 | 81 |
| Example 25 | DPC | 0.5 | 85 | (carbamate structure) | | | (diisocyanate, NCO / OCN with ethyl ester) | 82 |
| Example 26 | DPC | 0.5 | 86 | (carbamate structure) | | | (diisocyanate with ethyl ester) | 84 |
| Example 27 | DPC | 0.5 | 88 | (carbamate structure) | | | (aliphatic diisocyanate, NCO / OCN) | 85 |
| Example 28 | DPC | 0.5 | 86 | (carbamate structure) | | | (aliphatic diisocyanate, NCO / OCN) | 86 |

TABLE 5-continued

| | | | | | |
|---|---|---|---|---|---|
| Example 29 | DPC | 0.5 | 87 | [isophorone bis-phenyl carbamate structure] | 81 [isophorone diisocyanate (IPDI)] |
| Example 30 | DPC | 0.5 | 84 | [4,4'-methylenebis(phenyl) bis-phenyl carbamate] | 84 [4,4'-methylenebis(phenyl isocyanate) (MDI)] |
| Example 31 | DPC | 0.5 | 85 | [4,4'-methylenebis(cyclohexyl) bis-phenyl carbamate] | 83 [4,4'-methylenebis(cyclohexyl isocyanate) (H12MDI)] |
| Example 32 | DPC | 0.5 | 86 | [m-xylylene bis-phenyl carbamate] | 82 [m-xylylene diisocyanate (XDI)] |

TABLE 6

| | Raw materials for amine compound production | | Production raw materials for compound having urea linkage | | | | Production of compound having urea linkage | | | |
|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 33 | — | — | — | H₂N—CH₂—(cyclohexane)—CH₂—NH₂ | urea | 0.488 | 2,5-DMPhOH | — | 220 | 140 | 84 |
| Example 34 | — | — | — | 2,4-diamino toluene (NH₂, NH₂ on methylbenzene) | urea | 0.488 | 2,5-DMPhOH | — | 225 | 140 | 83 |
| Example 35 | — | — | — | branched triamine (H₂N, NH₂, NH₂) | urea | 0.488 | 2,5-DMPhOH | — | 225 | 140 | 80 |
| Example 36 | — | — | — | aminoethyl methacrylate (NH₂-CH₂CH₂-O-C(=O)-C(CH₃)=CH₂) | urea | 0.488 | 2,5-DMPhOH | — | 225 | 140 | 82 |

TABLE 6-continued

| | | | | | | | |
|---|---|---|---|---|---|---|---|
| Example 37 | lysine (structure: H2N-(CH2)4-CH(NH2)-COOH) | mono ethanol-amine | urea | 0.488 | 2,5-DMPhOH | — | 240 | 140 | 80 |
| Example 38 | alanine (structure: CH3-CH(NH2)-COOH) | mono ethanol-amine | urea | 0.488 | 2,5-DMPhOH | — | 245 | 140 | 81 |
| Example 39 | arginine (structure with guanidino group) | mono ethanol-amine | urea | 0.488 | 2,5-DMPhOH | — | 255 | 140 | 83 |

Production of carbamate

| | Carbonate ester | Required carbonate ester equivalence relative to urea conjugate | Carbamate yield |
|---|---|---|---|
| Example 33 | DPC | 0.5 | 87 |

Production of isocyanate by thermal decomposition of carbamate

| Obtained carbamate | Obtained isocyanate | Thermal decomposition yield (%) |
|---|---|---|
| cyclohexane-1,2-diyl-bis(methylene) bis(phenyl carbamate) | 1,2-bis(isocyanatomethyl)cyclohexane | 83 |

TABLE 6-continued
| Example | | | | | |
|---|---|---|---|---|---|
| Example 34 | DPC | 0.5 | 88 |  | 84 |
| Example 35 | DPC | 0.5 | 87 | 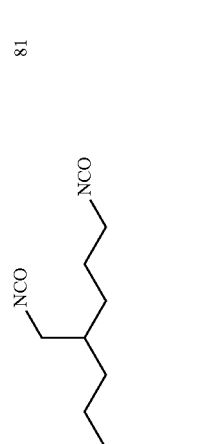 | 81 |
| Example 36 | DPC | 0.5 | 84 | 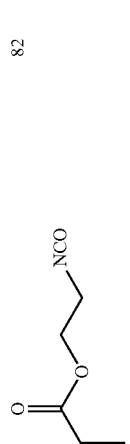 | 82 |
| Example 37 | DPC | 0.5 | 82 | 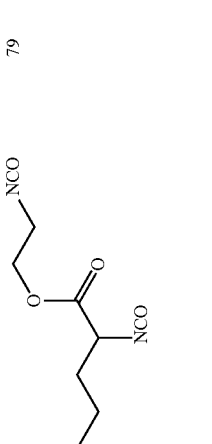 | 79 |

TABLE 6-continued

| Example 38 | DPC | 0.5 | 84 | (structure) | 81 | (structure) |
| Example 39 | DPC | 0.5 | 81 | (structure) | 83 | (structure) |

Example 37

With the exception of adding 224 g (0.75 mol) of the lysine-aminoethyl ester trihydrochloride obtained in Example 12 and 67.5 g (1.12 mol) of urea, the same operations as those described from the carbamate production step onward in Example 27 were conducted, yielding the corresponding carbamate and isocyanate shown in Table 6.

Examples 38 to 49

With the exceptions of altering the amino acid and the alcohol used when synthesizing the amino acid ester to each of the amino acids and alcohols listed in Tables 6 to 9, the same operations as Example 37 were conducted to obtain the corresponding carbamates and isocyanates shown in Tables 6 to 9. The urea added was added in an amount corresponding with the amount of raw material amine terminals to be converted to urea linkages. Further, in the case where arginine was used, the arginine was hydrolyzed using a conventional method to form ornithine prior to use. Furthermore, in the cases where glutamine or asparagine was used, a conventional method was used to hydrolyze the glutamine or asparagine to form glutamic acid or aspartic acid respectively prior to use.

TABLE 7

| | Raw materials for amine compound production | | | Production of compound having urea linkage | | | | | | |
|---|---|---|---|---|---|---|---|---|---|---|
| | | | | Production raw materials for compound having urea linkage | | | | Water extraction during production of compound having urea linkage | Thermal dissociation temperature | Reaction temperature | Raw material amine conversion rate |
| | Amino acid, amino acid derivative | Amino acid structural formula | Alkanolamine/ alcohol | Amine | Carbonyl source | Equivalence relative to amine terminals | Solvent | | | | |
| Example 40 | aspartic acid | [structure] | monoethanolamine | [structure] | urea | 0.488 | 2,5-DMPhOH | — | 245 | 140 | 80 |
| Example 41 | glutamic acid | [structure] | monoethanolamine | [structure] | urea | 0.488 | 2,5-DMPhOH | — | 260 | 140 | 79 |
| Example 42 | glycine | [structure] | monoethanolamine | [structure] | urea | 0.488 | 2,5-DMPhOH | — | 250 | 140 | 77 |
| Example 43 | synthetic amino acid | — | monoethanolamine | [structure] | urea | 0.488 | 2,5-DMPhOH | — | 240 | 140 | 78 |

TABLE 7-continued
| | Carbonate ester | Required carbonate ester equivalence relative to urea conjugate | Carbamate yield | Obtained carbamate | | Obtained isocyanate | Thermal decomposition yield (%) |
|---|---|---|---|---|---|---|---|
| Example 44 | lysine  | EtOH | urea | 0.488 | 2,5-DMPhOH | — | 255 | 140 | 79 |
| | | Production of carbamate | | | | Production of isocyanate by thermal decomposition of carbamate | |
| Example 40 | DPC | 0.5 | 82 | 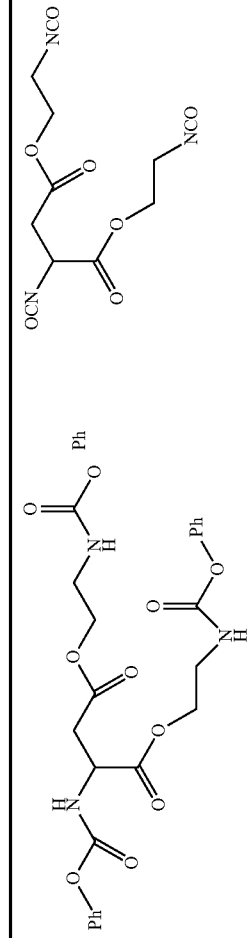 | | | 82 |
| Example 41 | DPC | 0.5 | 81 | 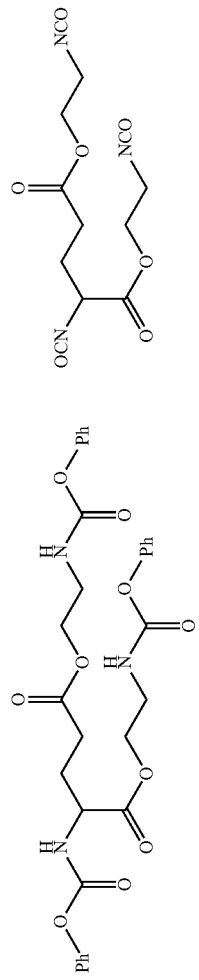 | | | 79 |
| Example 42 | DPC | 0.5 | 84 | | |  | 77 |

TABLE 7-continued

| Example 43 | DPC | 0.5 | 83 | (methyl 2-furyl carbamate, Ph-O-C(=O)-NH-CH(furan)-C(=O)-OMe) | (methyl 2-furyl isocyanate, OCN-CH(furan)-C(=O)-OMe) | 74 |
| Example 44 | DPC | 0.5 | 81 | (ethyl lysine bis-phenylcarbamate) | (ethyl lysine diisocyanate, OCN-(CH2)4-CH(NCO)-C(=O)-OEt) | 75 |

TABLE 8

| | Raw materials for amine compound | | Production raw materials for compound having urea linkage | | | | Production of compound having urea linkage | | | | |
|---|---|---|---|---|---|---|---|---|---|---|---|
| | | | | | | | | | Water extraction during production of compound having urea linkage | Thermal dissociation temperature | Reaction temperature | Raw material amine conversion rate |
| | production Amino acid, amino acid derivative | Amino acid structural formula | Alkanolamine/ alcohol | Amine | Carbonyl source | Equivalence relative to amine terminals | Solvent | | | | |
| Example 45 | lysine | (lysine structure) | 1-amino-2-PrOH | (amine structure) | urea | 0.488 | 2,5-DMPhOH | — | 240 | 140 | 81 |
| Example 46 | lysine | (lysine structure) | 2-amino-1-BuOH | (amine structure) | urea | 0.488 | 2,5-DMPhOH | — | 250 | 140 | 82 |
| Example 47 | glutamic acid | (glutamic acid structure) | EtOH | (amine structure) | urea | 0.488 | 2,5-DMPhOH | — | 240 | 140 | 84 |

TABLE 8-continued

| | | | | | | |
|---|---|---|---|---|---|---|
| Example 48 | glutamic acid | 1-amino-2-PrOH | urea | 0.488 | 2,5-DMPhOH | — | 140 | 82 |

Production of carbamate

| | Required carbonate ester | | |
|---|---|---|---|
| | Carbonate ester | equivalence relative to urea conjugate | Carbamate yield | Obtained carbamate |

Production of isocyanate by thermal decomposition of carbamate

| | Obtained isocyanate | Thermal decomposition yield (%) |
|---|---|---|

| Example 45 | DPC | 0.5 | 82 | | | 78 |
| Example 46 | DPC | 0.5 | 84 | | | 76 |

TABLE 8-continued
| | | | | | |
|---|---|---|---|---|---|
| Example 47 | DPC | 0.5 | 82 | 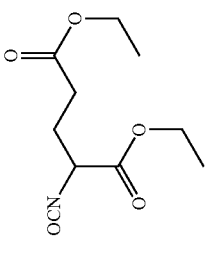 | 75 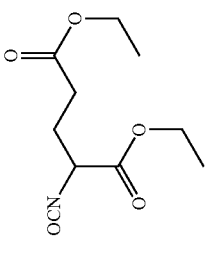 |
| Example 48 | DPC | 0.5 | 83 | 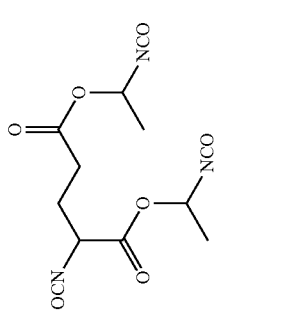 | 72 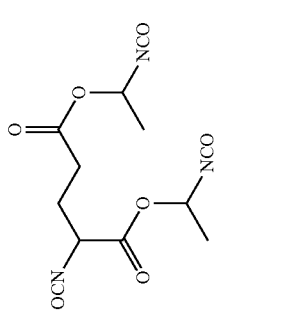 |

TABLE 9

| | Raw materials for amine compound production | | | Production of compound having urea linkage | | | | | | |
|---|---|---|---|---|---|---|---|---|---|---|
| | Amino acid, amino acid derivative | Amino acid structural formula | Alkanolamine/ alcohol | Production raw materials for compound having urea linkage | | Equivalence | | Water extraction during production of compound having urea linkage | Thermal dissociation temperature | Reaction temperature | Raw material amine conversion rate |
| | | | | Amine | Carbonyl source | relative to amine terminals | Solvent | | | | |
| Example 49 | glutamic acid | H₂N-CH(COOH)-CH₂-CH₂-COOH (structure) | 2-amino-1-BuOH | diester of glutamic acid with 2-amino-butyl groups (structure) | urea | 0.488 | 2,5-DMPhOH | — | 260 | 140 | 80 |
| Example 50 | — | — | — | H₂N-(CH₂)₆-NH₂ (structure) | urea | 1.00 | 2,5-DMPhOH | — | 220 | 140 | 95 |
| Example 51 | — | — | — | H₂N-(CH₂)₇-NH₂ (structure) | urea | 1.00 | 2,5-DMPhOH | — | 215 | 140 | 98 |
| Example 52 | — | — | — | isophorone diamine (structure) | urea | 1.00 | 2,5-DMPhOH | — | 220 | 140 | 97 |
| Example 53 | — | — | — | bis(4-aminophenyl)methane (structure) | urea | 1.00 | 2,5-DMPhOH | — | 220 | 140 | 98 |
| Example 54 | — | — | — | bis(4-aminocyclohexyl)methane (structure) | urea | 1.00 | 2,5-DMPhOH | — | 210 | 140 | 95 |

TABLE 9-continued

| | | Production of carbamate | | | | Production of isocyanate by thermal decomposition of carbamate | | | |
|---|---|---|---|---|---|---|---|---|---|
| | Carbonate ester | Required carbonate ester equivalence relative to urea conjugate | Carbamate yield | | | Obtained carbamate | Obtained isocyanate | | Thermal decomposition yield (%) |
| Example 55 | — | — | 82 | urea | 1.00 | 2,5-DMPhOH | H₂N–CH₂–C₆H₄–CH₂–NH₂ (1,3-) | 215 | 140 | 94 |
| Example 56 | — | — | 88 | urea | 1.00 | 2,5-DMPhOH | cyclohexane-1,2-bis(methylamine) | 220 | 140 | 93 |
| Example 49 | DPC | 0.5 | 82 | | | bis-carbamate of glutaric diester with PhO-carbamate groups | diisocyanate of glutaric diester | | 76 |
| Example 50 | DPC | 0.5 | 88 | | | PhO(O)CNH-(CH₂)₆-NHC(O)OPh | OCN-(CH₂)₆-NCO | | 86 |
| Example 51 | DPC | 0.5 | 86 | | | PhO(O)CNH-(CH₂)₆-NHC(O)OPh | OCN-(CH₂)₆-NCO | | 86 |

TABLE 9-continued

| | | | | | |
|---|---|---|---|---|---|
| Example 52 | DPC | 0.5 | 87 | [isophorone diisocyanate structure] | [isophorone bis-phenyl carbamate structure] 81 |
| Example 53 | DPC | 0.5 | 84 | [4,4'-methylenebis(phenyl isocyanate)] | [bis-phenyl carbamate of MDI] 84 |
| Example 54 | DPC | 0.5 | 85 | [4,4'-methylenebis(cyclohexyl isocyanate)] | [bis-phenyl carbamate of H12MDI] 83 |
| Example 55 | DPC | 0.5 | 86 | [m-xylylene diisocyanate] | [bis-phenyl carbamate of MXDI] 82 |
| Example 56 | DPC | 0.5 | 87 | [1,2-bis(isocyanatomethyl)cyclohexane] | [bis-phenyl carbamate of 1,2-BIC] 83 |

Example 50

(Production Step for Compound Having an Ureido Group Using a Carbonic Acid Derivative)

First, 120 g (1.03 mol) of 1,6-hexamethylenediamine and 124 g (2.06 mol) of urea were placed in a 3 L four-neck flask, and the gas phase was replaced with nitrogen. At this time, the amount of urea relative to the amino groups in the added raw material was 1.00. Next, 1,100 g of anhydrous 2,5-dimethylphenol was added, the internal temperature was adjusted to 120° C. and the internal pressure was adjusted to 80 kPa. The reaction was continued for 15 hours, while the by-product ammonia was removed from the system by distillation, and the reactor was then returned to room temperature and normal pressure. Quantitative analysis by NMR revealed a conversion rate from the raw material amine of 95%.

(Step for Obtaining Compound having Urea Linkage from Compound having Ureido Group)

Using the reaction liquid obtained in the above production step for the compound having a ureido group, the liquid was stirred under heating at 160° C. for one hour at normal pressure, and the overall pressure was then gradually reduced to 20 kPa, and the 2,5-dimethylphenol solvent and the urea produced as a by-product during the urea conjugate production were removed from the system by distillation over a period of 7 hours. Following removal of the solvent, the temperature was lowered and the pressure was returned to normal pressure, and analysis of the residue by IR (KBr method) confirmed absorptions at 1618 cm$^{-1}$ (C=O stretch) and 1572 cm$^{-1}$ (NH stretch), confirming a conversion to a compound having a urea linkage. Quantitative analysis by NMR revealed that the urea conjugate produced from the raw material compound having a ureido group was obtained with a yield of 87% relative to the raw material amine.

(Production Step for Carbamate)

The composition containing the compound having a urea linkage produced in the step described above was transferred to a 2 L four-neck flask fitted with a stirrer, 950 g of ortho-dichlorobenzene as a solvent and 209 g (0.98 mol) of diphenyl carbonate, an amount equimolar with the produced urea conjugate, were added to the flask, and the resulting mixture was reacted at 80° C. for 10 hours. The reaction liquid was sampled, and analysis by liquid chromatography revealed that the target carbamate had been produced in a yield of 85% relative to the raw material urea conjugate. Hydrochloric acid with a concentration of 1 mol/L was added to the reaction liquid and stirred, and the organic layer was then collected and washed with ion-exchanged water. The ortho-dichlorobenzene was removed from the organic layer by distillation using a rotary evaporator, and analysis of the thus obtained solid by H-NMR confirmed the target carbamate (purity: 99%). The yield of the carbamate relative to the raw material amine was 88%.

(Reaction Mixture Production Step, Decomposition Step, Low-Boiling Point Decomposition Product Collection Step and High-Boiling Point Solvent Collection Step)

Using the carbamate obtained from the above operations, the same operations as Example 27 were conducted, obtaining the corresponding isocyanate shown in Table 9.

Examples 51 to 59

With the exception of replacing the raw material amine used with each of the amines listed in Table 9, the same operations as Example 50 were conducted, yielding the corresponding carbamates and isocyanates shown in Table 9. The molar ratio of urea relative to the amino groups of the added raw material was the same as Example 50.

TABLE 10

| | Raw materials for amine compound production | | | Production raw materials for compound having urea linkage | | | | Production of compound having urea linkage | | | |
|---|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 57 | — | — | — | ![benzene with NH2 groups and methyl] | urea | 1.00 | 2,5-DMPhOH | — | 225 | 140 | 94 |
| Example 58 | — | — | — | ![branched amine with three NH2] | urea | 1.00 | 2,5-DMPhOH | — | 225 | 140 | 96 |
| Example 59 | — | — | — | ![methacrylate ester with amine] | urea | 1.00 | 2,5-DMPhOH | — | 225 | 140 | 99 |
| Example 60 | lysine | ![lysine structure] | mono ethanol-amine | ![lysine ester with ethanolamine] | urea | 1.00 | 2,5-DMPhOH | — | 240 | 140 | 98 |

TABLE 10-continued

| | Carbonate ester | Required carbonate ester equivalence relative to urea conjugate | Carbamate yield | | | | |
|---|---|---|---|---|---|---|---|
| Example 61 | | | | alanine |  | urea | 1.00 | 2,5-DMPhOH | — | 245 | 140 | 97 |
| Example 62 | | | | arginine |  | urea | 1.00 | 2,5-DMPhOH | — | 255 | 140 | 95 |

| | | Production of carbamate | | Production of isocyanate by thermal decomposition of carbamate | | |
|---|---|---|---|---|---|---|
| | Carbonate ester | Required carbonate ester equivalence relative to urea conjugate | Carbamate yield | Obtained carbamate | Obtained isocyanate | Thermal decomposition yield (%) |
| Example 57 | DPC | 0.5 | 88 |  |  | 84 |
| Example 58 | DPC | 0.5 | 87 |  | 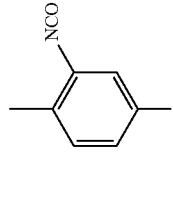 | 81 |
| Example 59 | DPC | 0.5 | 84 |  | 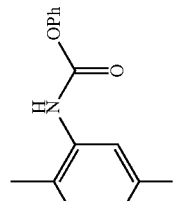 | 82 |

TABLE 10-continued
| | | | | | |
|---|---|---|---|---|---|
| Example 60 | DPC | 0.5 | 82 | 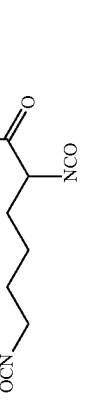 | 79  |
| Example 61 | DPC | 0.5 | 84 | 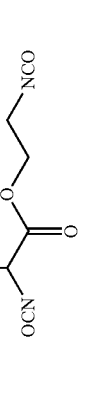 | 81  |
| Example 62 | DPC | 0.5 | 81 | 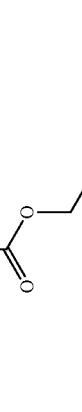 | 83 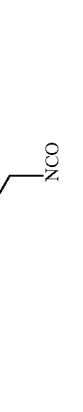 |

Example 60

With the exception of adding 224 g (0.75 mol) of the lysine-aminoethyl ester trihydrochloride obtained in Example 12 and 134 g (2.25 mol) of urea, the same operations as those described from the carbamate production step onward in Example 50 were conducted, yielding the corresponding carbamate and isocyanate shown in Table 10.

Examples 61 to 72

With the exceptions of altering the amino acid and the alcohol used when synthesizing the amino acid ester to each of the amino acids and alcohols listed in Tables 10 and 11, the same operations as Example 60 were conducted to obtain the corresponding carbamates and isocyanates shown in Tables 10 and 11. The urea added was added in an amount corresponding with the amount of raw material amine terminals to be converted to ureido groups. Further, in the case where arginine was used, the arginine was hydrolyzed using a conventional method to form ornithine prior to use. Furthermore, in the cases where glutamine or asparagine was used, a conventional method was used to hydrolyze the glutamine or asparagine to form glutamic acid or aspartic acid respectively prior to use.

TABLE 11

| | Raw materials for amine compound production | | | Production of compound having urea linkage | | | | | | |
|---|---|---|---|---|---|---|---|---|---|---|
| | | | | Production raw materials for compound having urea linkage | | | Equivalence | | | |
| | Amino acid, amino acid derivative | Amino acid structural formula | Alkanolamine/ alcohol | Amine | Carbonyl source | Solvent | relative to amine terminals | Water extraction during production of compound having urea linkage | Thermal dissociation temperature | Reaction temperature | Raw material amine conversion rate |
| Example 63 | aspartic acid | H₂N-CH(COOH)-CH₂-COOH | mono ethanol- amine | [structure with H₂N, NH₂, ester linkages] | urea | 2,5-DMPhOH | 1.00 | — | 245 | 140 | 97 |
| Example 64 | glutamic acid | HOOC-CH₂-CH₂-CH(NH₂)-COOH | mono ethanol- amine | [structure with H₂N, NH₂, ester linkages] | urea | 2,5-DMPhOH | 1.00 | — | 260 | 140 | 98 |
| Example 65 | glycine | H₂N-CH₂-COOH | mono ethanol- amine | [structure with H₂N, NH₂, ester linkage] | urea | 2,5-DMPhOH | 1.00 | — | 250 | 140 | 94 |
| Example 66 | synthetic amino acid | — | mono ethanol- amine | [furan-containing structure with NH₂, methyl ester] | urea | 2,5-DMPhOH | 1.00 | — | 240 | 140 | 95 |

TABLE 11-continued

| Example | | | | | | | | | | |
|---|---|---|---|---|---|---|---|---|---|---|
| Example 67 | lysine | [structure: lysine with NH₂, H₂N, OH, C=O] | EtOH | [structure: ethyl ester of lysine with NH₂, H₂N] | urea | 1.00 | 2,5-DMPhOH | — | 255 | 140 | 94 |

Production of carbamate

| | Carbonate ester | Required carbonate ester equivalence relative to urea conjugate | Carbamate yield | Obtained carbamate |
|---|---|---|---|---|
| Example 63 | DPC | 0.5 | 82 | [structure: bis-phenyl carbamate of aspartate diester] |
| Example 64 | DPC | 0.5 | 81 | [structure: bis-phenyl carbamate of glutamate diester] |

Production of isocyanate by thermal decomposition of carbamate

| | Obtained isocyanate | Thermal decomposition yield (%) |
|---|---|---|
| Example 63 | [structure: diisocyanate of aspartate diester, OCN…NCO] | 82 |
| Example 64 | [structure: diisocyanate of glutamate diester, OCN…NCO] | 79 |

TABLE 11-continued
| Example | | | | | |
|---|---|---|---|---|---|
| Example 65 | DPC | 0.5 | 84 |  |  77 |
| Example 66 | DPC | 0.5 | 83 | 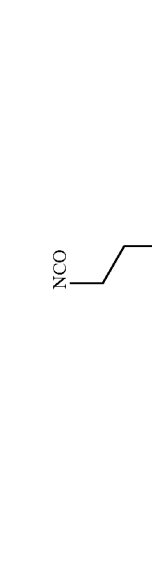 |  74 |
| Example 67 | DPC | 0.5 | 81 |  | 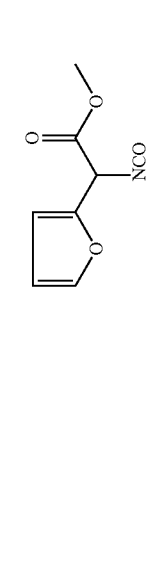 75 |

TABLE 12

| | Raw materials for amine compound production | | | Production of compound having urea linkage | | | | | | |
|---|---|---|---|---|---|---|---|---|---|---|
| | Amino acid, amino acid derivative | Amino acid structural formula | Alkanolamine/ alcohol | Production raw materials for compound having urea linkage | | | | Water extraction during production of compound having urea linkage | Thermal dissociation temperature | Reaction temperature | Raw material amine conversion rate |
| | | | | Amine | Carbonyl source | Equivalence relative to amine terminals | Solvent | | | | |
| Example 68 | lysine | [lysine structure] | 1-amino-2-PrOH | [amine structure] | urea | 1.00 | 2,5-DMPhOH | — | 240 | 140 | 96 |
| Example 69 | lysine | [lysine structure] | 2-amino-1-BuOH | [amine structure] | urea | 1.00 | 2,5-DMPhOH | — | 250 | 140 | 97 |
| Example 70 | glutamic acid | [glutamic acid structure] | EtOH | [amine structure] | urea | 1.00 | 2,5-DMPhOH | — | 240 | 140 | 96 |

TABLE 12-continued
| | | Example 71 |
|---|---|---|
| | glutamic acid | 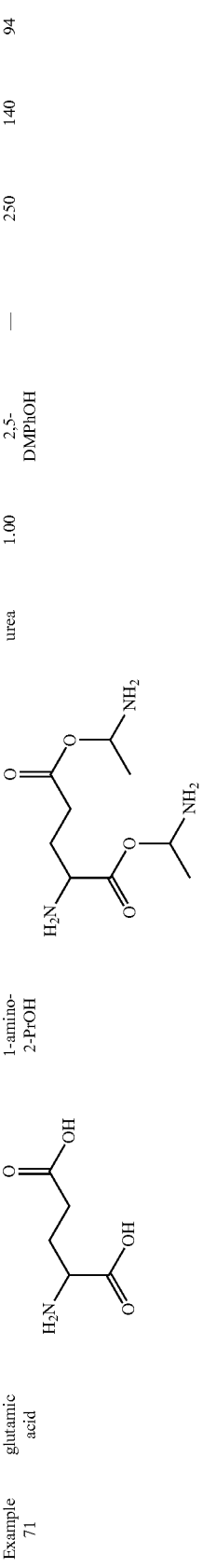 |
| | urea | |
| | 1-amino-2-PrOH | |
| | 2,5-DMPhOH | |
| | 1.00 | |
| | 250 | |
| | 140 | |
| | 94 | |
| | | Production of carbamate | | | Production of isocyanate by thermal decomposition of carbamate | |
|---|---|---|---|---|---|---|
| | | Required carbonate ester | | | | |
| | Carbonate ester | equivalence relative to urea conjugate | Carbamate yield | Obtained carbamate | Obtained isocyanate | Thermal decomposition yield (%) |
| Example 68 | DPC | 0.5 | 82 | 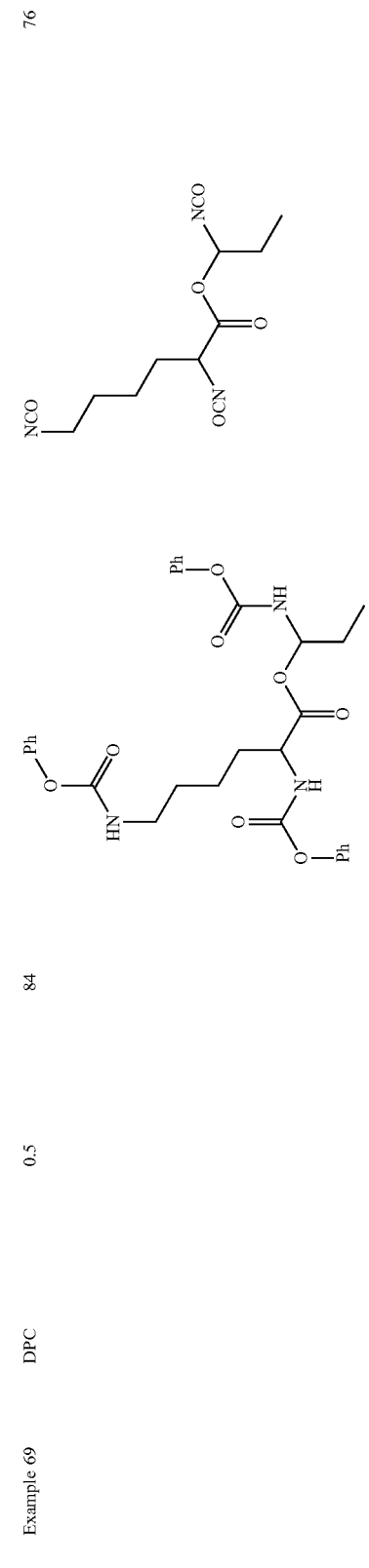 | | 78 |
| Example 69 | DPC | 0.5 | 84 | | | 76 |

TABLE 12-continued
| | | | | | |
|---|---|---|---|---|---|
| Example 70 | DPC | 0.5 | 82 | 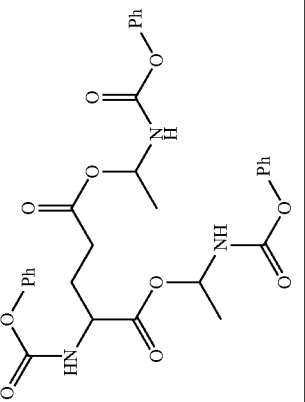 | 75 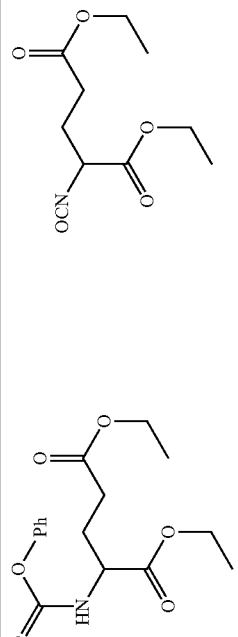 |
| Example 71 | DPC | 0.5 | 83 | 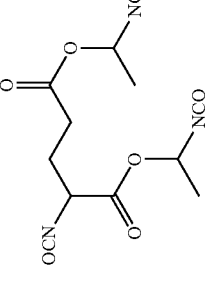 | 72 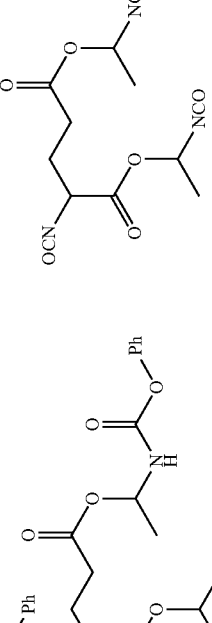 |

TABLE 13

| | Raw materials for amine compound production | | Production raw materials for compound having urea linkage | | | Production of compound having urea linkage | | | | |
|---|---|---|---|---|---|---|---|---|---|---|
| | | | | | Equivalence | | Water extraction during production of compound having urea linkage | Thermal dissociation temperature | Reaction temperature | Raw material amine conversion rate |
| | Amino acid, amino acid derivative | Amino acid structural formula | Alkanolamine/ alcohol | Amine | Carbonyl source | relative to amine terminals | Solvent | | | |
| Example 72 | glutamic acid | $H_2N$–CH(COOH)–CH_2–CH_2–COOH | 2-amino-1-BuOH | (diester of glutamic acid with two terminal $NH_2$ groups) | urea | 1.00 | 2,5-DMPhOH | — | 260 | 140 | 95 |
| Comparative Example 1 | — | — | — | $H_2N$–(CH_2)_6–$NH_2$ | none | — | 2,5-DMPhOH | — | 220 | 140 | 0 |
| Comparative Example 2 | — | — | — | $H_2N$–(CH_2)_6–$NH_2$ | none | — | 2,5-DMPhOH | — | 220 | 140 | 0 |
| Comparative Example 3 | — | — | — | $H_2N$–(CH_2)_6–$NH_2$ | none | — | 2,5-DMPhOH | — | 220 | 140 | 0 |

TABLE 13-continued

| | Required carbonate ester | | Production of carbamate | | Production of isocyanate by thermal decomposition of carbamate | |
|---|---|---|---|---|---|---|
| | Carbonate ester | equivalence relative to urea conjugate | Carbamate yield | Obtained carbamate | Obtained isocyanate | Thermal decomposition yield (%) |
| Example 72 | DPC | 0.5 | 82 | ![structure: bis-carbamate with PhO-C(=O)-NH groups on a diester backbone] | ![structure: bis-isocyanate diester with two NCO groups] | 76 |
| Comparative Example 1 | DPC | 1.0 (relative to amine terminals) | 75 | ![structure: PhO-C(=O)-NH-(CH2)n-NH-C(=O)-OPh] | ![structure: OCN-(CH2)n-NCO] | 86 |
| Comparative Example 2 | DPC | 1.0 (relative to amine terminals) | 76 | ![structure: PhO-C(=O)-NH-(CH2)n-NH-C(=O)-OPh] | ![structure: OCN-(CH2)n-NCO] | 86 |
| Comparative Example 3 | DPC | 1.0 (relative to amine terminals) | 78 | ![structure: PhO-C(=O)-NH-(CH2)n-NH-C(=O)-OPh] | ![structure: OCN-(CH2)n-NCO] | 86 |

Comparative Example 1

With the exception of supplying nitrogen instead of carbon dioxide in Example 1, the same operations as Example 1 were conducted, and although a carbamate derived from the raw material amine and diphenyl carbonate was obtained in the step of obtaining a carbamate, the amount of diphenyl carbonate consumed was one equivalent relative to the amine terminals, indicating a significant increase in the amount of diphenyl carbonate added.

Comparative Example 2

With the exception of not adding the urea in Example 27, the same operations as Example 27 were conducted, and although a carbamate derived from the raw material amine and diphenyl carbonate was obtained in the step of obtaining a carbamate, the amount of diphenyl carbonate consumed was one equivalent relative to the amine terminals, indicating a significant increase in the amount of diphenyl carbonate added.

Comparative Example 31

With the exception of not adding the urea in Example 50, the same operations as Example 50 were conducted, and although a carbamate derived from the raw material amine and diphenyl carbonate was obtained in the step of obtaining a carbamate, the amount of diphenyl carbonate consumed was one equivalent relative to the amine terminals, indicating a significant increase in the amount of diphenyl carbonate added.

Example 73

With the exception of replacing the anhydrous 2,5-dimethylphenol in Example 27 with anhydrous o-dichlorobenzene, the same operations as Example 27 were conducted. Analysis of the component obtained following the reaction by IR (KBr method) confirmed absorptions at 1618 cm$^{-1}$ (C=O stretch) and 1571 cm$^{-1}$ (NH stretch), but because a gel-like substance was adhered to a portion of the reactor following reaction, the solution was not transferred, but was simply used in the carbamate production step.
(Production Step for Carbamate)

When synthesis was conducted under the same conditions as Example 27, the adhered gel-like substance dissolved over time, and a uniform solution was eventually obtained. Analysis by liquid chromatography revealed that the target carbamate had been produced in a yield of 86% relative to the raw material urea conjugate.

Examples 74 to 95

With the exception of replacing the anhydrous 2,5-dimethylphenol with anhydrous o-dichlorobenzene in each of Examples 28 to 49, the same operations as Examples 28 to 49 were conducted, yielding the corresponding carbamates and isocyanates shown in Tables 14 to 17.

TABLE 14

| | Raw materials for amine compound production | | | Production raw materials for compound having urea linkage | Production of compound having urea linkage | | | | | | Raw material amine conversion rate |
|---|---|---|---|---|---|---|---|---|---|---|---|
| | Amino acid, amino acid derivative | Amino acid structural formula | Alkanolamine/alcohol | Amine | Carbonyl source | Equivalence relative to amine terminals | Solvent | Water extraction during production of compound having urea linkage | Thermal dissociation temperature | Reaction temperature | |
| Example 73 | — | — | — | H₂N-(CH₂)₆-NH₂ (1,6-hexanediamine) | urea | 0.488 | ODB | — | 220 | 140 | 81 |
| Example 74 | — | — | — | H₂N-(CH₂)₇-NH₂ (heptanediamine) | urea | 0.488 | ODB | — | 215 | 140 | 79 |
| Example 75 | — | — | — | Isophorone diamine (3-aminomethyl-3,5,5-trimethylcyclohexylamine) | urea | 0.488 | ODB | — | 220 | 140 | 80 |
| Example 76 | — | — | — | 4,4'-methylenedianiline | urea | 0.488 | ODB | — | 220 | 140 | 78 |
| Example 77 | — | — | — | 4,4'-methylenebis(cyclohexylamine) | urea | 0.488 | ODB | — | 210 | 140 | 77 |
| Example 78 | — | — | — | m-xylylenediamine | urea | 0.488 | ODB | — | 215 | 140 | 81 |
| Example 79 | — | — | — | 1,2-bis(aminomethyl)cyclohexane | urea | 0.488 | ODB | — | 220 | 140 | 84 |

TABLE 14-continued

| | Production of carbamate | | | | Production of isocyanate by thermal decomposition of carbamate | |
|---|---|---|---|---|---|---|
| Example 80 | — | — | urea | 0.488 | ODB | — | 225 | 140 | 83 |

Structure shown for Example 80: toluene-2,4-diamine (methylbenzene with two NH₂ groups)

| | Carbonate ester | Required carbonate ester equivalence relative to urea conjugate | Carbamate yield | Obtained carbamate | Obtained isocyanate | Thermal decomposition yield (%) |
|---|---|---|---|---|---|---|
| Example 73 | DPC | 0.5 | 86 | PhO-C(O)-NH-(CH₂)₆-NH-C(O)-OPh | OCN-(CH₂)₆-NCO | 85 |
| Example 74 | DPC | 0.5 | 85 | PhO-C(O)-NH-CH₂-(CH₂)₄-NH-C(O)-OPh | OCN-CH₂-(CH₂)₄-NCO | 86 |
| Example 75 | DPC | 0.5 | 86 | Isophorone bis-carbamate (PhO-carbamate) | Isophorone diisocyanate (IPDI) | 81 |
| Example 76 | DPC | 0.5 | 82 | 4,4'-methylenebis(phenyl carbamate) (PhO-) | 4,4'-methylenebis(phenyl isocyanate) (MDI) | 84 |
| Example 77 | DPC | 0.5 | 84 | 4,4'-methylenebis(cyclohexyl carbamate) (PhO-) | 4,4'-methylenebis(cyclohexyl isocyanate) (H12MDI) | 83 |

TABLE 14-continued
| Example 78 | DPC | 0.5 | 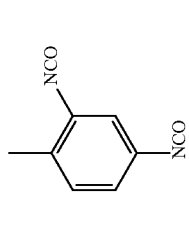 | 84 | 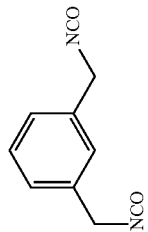 | 82 |
| Example 79 | DPC | 0.5 | 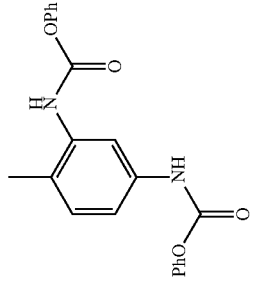 | 85 | 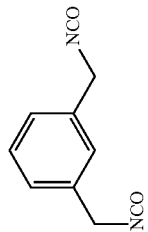 | 83 |
| Example 80 | DPC | 0.5 | 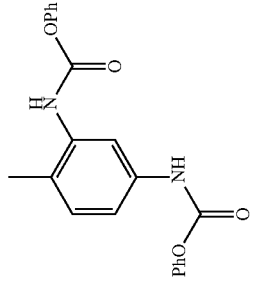 | 86 | 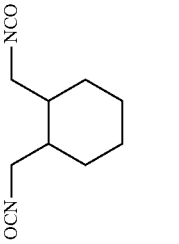 | 84 |

TABLE 15

| | Raw materials for amine compound production | | | Production raw materials for compound having urea linkage | | | Equivalence relative to amine terminals | Solvent | Water extraction during production of compound having urea linkage | Thermal dissociation temperature | Reaction temperature | Raw material amine conversion rate |
|---|---|---|---|---|---|---|---|---|---|---|---|---|
| | Amino acid, amino acid derivative | Amino acid structural formula | Alkanolamine/alcohol | Amine | | Carbonyl source | | | | | | |
| Example 81 | — | — | — | ![structure with two NH2 groups] | | urea | 0.488 | ODB | — | 225 | 140 | 80 |
| Example 82 | — | — | — | ![methacrylate with aminoethyl ester] | | urea | 0.488 | ODB | — | 225 | 140 | 82 |
| Example 83 | lysine | ![lysine structure] | mono ethanol- amine | ![lysine ethanolamine ester structure] | | urea | 0.488 | ODB | — | 240 | 140 | 80 |
| Example 84 | alanine | ![alanine structure] | mono ethanol- amine | ![alanine ethanolamine ester structure] | | urea | 0.488 | ODB | — | 245 | 140 | 81 |

TABLE 15-continued

| | | | | | | | | |
|---|---|---|---|---|---|---|---|---|
| Example 85 | arginine | (structure: arginine) | mono ethanol- amine | (structure: arginine-monoethanolamine conjugate) | urea | 0.488 | ODB | 255 | 140 | 83 |
| Example 86 | aspartic acid | (structure: aspartic acid) | mono ethanol- amine | (structure: aspartic acid-monoethanolamine conjugate) | urea | 0.488 | ODB | 245 | 140 | 80 |
| Example 87 | glutamic acid | (structure: glutamic acid) | mono ethanol- amine | (structure: glutamic acid-monoethanolamine conjugate) | urea | 0.488 | ODB | 260 | 140 | 79 |

| | Production of carbamate | | Production of isocyanate by thermal decomposition of carbamate | |
|---|---|---|---|---|
| | Required carbonate | | | |
| Carbonate ester | ester equivalence relative to urea conjugate | Carbamate yield | Obtained carbamate | Obtained isocyanate | Thermal decomposition yield (%) |
| Example 81 | DPC | 0.5 | 85 | (carbamate structure with OPh groups) | (isocyanate structure with NCO groups) | 81 |

TABLE 15-continued
| Example | | | | | |
|---|---|---|---|---|---|
| Example 82 | DPC | 0.5 | 82 | 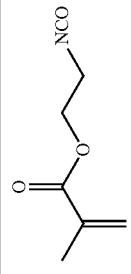 | 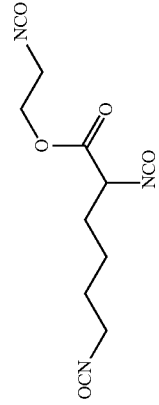 82 |
| Example 83 | DPC | 0.5 | 81 | 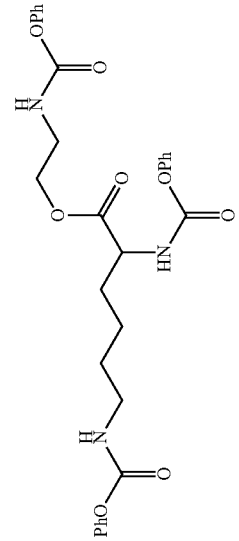 | 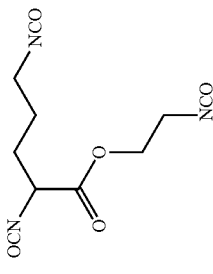 79 |
| Example 84 | DPC | 0.5 | 82 | 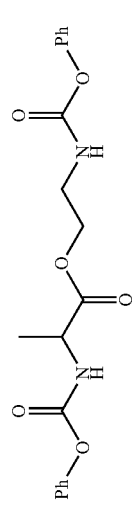 | 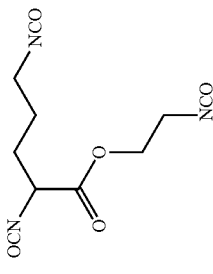 81 |
| Example 85 | DPC | 0.5 | 80 | 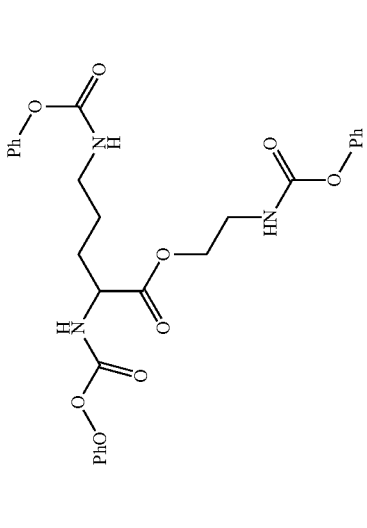 | 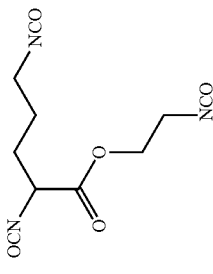 83 |

TABLE 15-continued

| Example 86 | DPC | 0.5 | 80 | (structure) | (structure) | 82 |
| Example 87 | DPC | 0.5 | 80 | (structure) | (structure) | 79 |

TABLE 16

| | Raw materials for amine compound production | | | Production of compound having urea linkage | | | | | | |
|---|---|---|---|---|---|---|---|---|---|---|
| | Raw materials for amine compound production | | | Production raw materials for compound having urea linkage | | Equivalence relative to amine terminals | Solvent | Water extraction during production of compound having urea linkage | Thermal dissociation temperature | Reaction temperature | Raw material amine conversion rate |
| | Amino acid, amino acid derivative | Amino acid structural formula | Alkanolamine/ alcohol | Amine | Carbonyl source | | | | | | |
| Example 88 | glycine | H₂N–CH₂–C(=O)–OH | mono ethanolamine | H₂N–CH₂–C(=O)–O–CH₂–CH₂–NH₂ | urea | 0.488 | ODB | — | 250 | 140 | 77 |
| Example 89 | synthetic amino acid | — | mono ethanolamine | methyl 2-(furan-2-yl)-2-aminoacetate | urea | 0.488 | ODB | — | 240 | 140 | 78 |
| Example 90 | lysine | lysine (H₂N–(CH₂)₄–CH(NH₂)–C(=O)–OH) | EtOH | ethyl 2,6-diaminohexanoate | urea | 0.488 | ODB | — | 255 | 140 | 79 |

TABLE 16-continued

| | | | | | | | |
|---|---|---|---|---|---|---|---|
| Example 91 | lysine | 1-amino-2-PrOH | urea | 0.488 | ODB | — | 240 | 140 | 81 |

| | Carbonate ester | Required carbonate ester equivalence relative to urea conjugate | Carbamate yield | Obtained carbamate | Obtained isocyanate | Thermal decomposition yield (%) |
|---|---|---|---|---|---|---|
| | | Production of carbamate | | | Production of isocyanate by thermal decomposition of carbamate | |
| Example 88 | DPC | 0.5 | 82 | (Ph-O-C(=O)-NH-CH2-C(=O)-O-CH2CH2-NH-C(=O)-O-Ph) | OCN-CH2-C(=O)-O-CH2CH2-NCO | 77 |
| Example 89 | DPC | 0.5 | 81 | (furan-CH(NH-C(=O)-O-Ph)-C(=O)-O-Me) | (furan-CH(NCO)-C(=O)-O-Me) | 74 |

TABLE 16-continued

| Example | | | | |
|---|---|---|---|---|
| Example 90 | DPC | 0.5 | 80 | 75 |
| Example 91 | DPC | 0.5 | 81 | 78 |

TABLE 17

| | Raw materials for amine compound production | | | Production of compound having urea linkage | | | | | | |
|---|---|---|---|---|---|---|---|---|---|---|
| | Amino acid, amino acid derivative | Amino acid structural formula | Alkanolamine/ alcohol | Production raw materials for compound having urea linkage | | Carbonyl source | Equivalence relative to amine terminals | Solvent | Water extraction during production of compound having urea linkage | Thermal dissociation temperature | Reaction temperature | Raw material amine conversion rate |
| | | | | Amine | | | | | | | | |
| Example 92 | lysine | (structure) | 2-amino-1-BuOH | (structure) | urea | 0.488 | ODB | — | 250 | 140 | 92 |
| Example 93 | glutamic acid | (structure) | EtOH | (structure) | urea | 0.488 | ODB | — | 240 | 140 | 84 |
| Example 94 | glutamic acid | (structure) | 1-amino-2-PrOH | (structure) | urea | 0.488 | ODB | — | 250 | 140 | 82 |

TABLE 17-continued

| | | Production of carbamate | | | | | | Production of isocyanate by thermal decomposition of carbamate | |
|---|---|---|---|---|---|---|---|---|---|
| | | | | | 2-amino-1-BuOH | urea | | | |
| Example 95 | glutamic acid | | | | | 0.488 | ODB | — | 260 140 80 |
| | | Carbonate ester | Required carbonate ester equivalence relative to urea conjugate | Carbamate yield | Obtained carbamate | | | Obtained isocyanate | Thermal decomposition yield (%) |
| Example 92 | | DPC | 0.5 | 82 | | | | | 76 |
| Example 93 | | DPC | 0.5 | 81 | | | | | 75 |

TABLE 17-continued

| Example 94 | DPC | 0.5 | [structure] | 81 | [structure] | 72 |
| Example 95 | DPC | 0.5 | [structure] | 81 | [structure] | 76 |

Comparative Example 4

In the production step for the compound having a urea linkage using carbon dioxide in Example 1, with the exception of altering the internal temperature to 300° C., the same operations as Example 1 were conducted, yielding the corresponding carbamate shown in Table 18.

Comparative Example 5

In the production step for the compound having a urea linkage using a carbonic acid derivative in Example 27, with the exception of altering the reaction temperature to 250° C. (because the boiling point of 2,5-dimethylphenol at atmospheric pressure is 212° C., the reaction was conducted in a pressurized system using a 3 L SUS316 autoclave), the same operations as Example 27 were conducted, yielding the corresponding carbamate shown in Table 18.

Comparative Example 6

In the step for obtaining the compound having a urea linkage from the compound having a ureido group in Example 50, with the exception of altering the reaction temperature to 250° C. (because the boiling point of 2,5-dimethylphenol at atmospheric pressure is 212° C., the reaction was conducted in a pressurized system using a 3 L SUS316 autoclave), the same operations as Example 50 were conducted, yielding the corresponding carbamate shown in Table 18.

Comparative Example 71

In the production step for the compound having a urea linkage using carbon dioxide in Example 1, with the exception of using phosgene as the carbonyl source, the same operations as Example 1 were conducted, and although the corresponding carbamate shown in Table 18 was obtained, multiple by-products were also produced, and the obtained carbamate, and the isocyanate obtained using the carbamate as a raw material, were a yellow-brown color.

Examples 96 to 118

With the exception of altering the amount of carbonic acid derivative used to 0.4 mol relative to each amine terminal, the same operations as Examples 27 to 49 were conducted, yielding the corresponding carbamates and isocyanates shown in Tables 18 to 22.

TABLE 18

| | Raw materials for amine compound production | | | Production of compound having urea linkage | | | | | | | |
|---|---|---|---|---|---|---|---|---|---|---|---|
| | | | | Production raw materials for compound having urea linkage | | | | | Water extraction during production of compound having urea linkage | Thermal dissociation temperature | Reaction temperature | Raw material amine conversion rate |
| | Amino acid, amino acid derivative | Amino acid structural formula | Alkanolamine/ alcohol | Amine | Carbonyl source | Equivalence relative amine to terminals | Solvent | | | | |
| Comparative Example 4 | — | — | — | H₂N~~~~NH₂ | CO₂ | — | — | — | — | 300 | 70 |
| Comparative Example 5 | — | — | — | H₂N~~~~NH₂ | urea | 0.488 | 2,5-DMPhOH | — | 220 | 250 | 70 |
| Comparative Example 6 | — | — | — | H₂N~~~~NH₂ | urea | 1.999 | 2,5-DMPhOH | — | 220 | 250 | 84 |
| Comparative Example 7 | — | — | — | H₂N~~~~NH₂ | phosgene | 1.00 | 2,5-DMPhOH | — | 220 | 200 | 99 |
| Example 96 | — | — | — | H₂N~~~~NH₂ | urea | 0.4 | 2,5-DMPhOH | — | 215 | 140 | 66 |
| Example 97 | — | — | — | H₂N~~~~NH₂ | urea | 0.4 | 2,5-DMPhOH | — | 220 | 140 | 65 |
| Example 98 | — | — | — | isophorone diamine | urea | 0.4 | 2,5-DMPhOH | — | 220 | 140 | 66 |
| Example 99 | — | — | — | 4,4'-methylenedianiline | urea | 0.4 | 2,5-DMPhOH | — | 210 | 140 | 64 |

TABLE 18-continued
| | Example 100 | | | urea 0.4 | 2,5-DMPhOH | | 215 | 140 | 63 |
|---|---|---|---|---|---|---|---|---|---|
| | Production of carbamate | | | Production of isocyanate by thermal decomposition of carbamate | | |
|---|---|---|---|---|---|---|
| | Carbonate ester | Carbamate yield | Obtained carbamate | | Obtained isocyanate | Thermal decomposition yield (%) |
| Comparative Example 4 | DPC 0.5 | 92 |  | |  | 86 |
| Comparative Example 5 | DPC 0.5 | 88 |  | |  | 86 |
| Comparative Example 6 | DPC 0.5 | 88 |  | |  | 86 |
| Comparative Example 7 | DPC 0.5 | 10 | 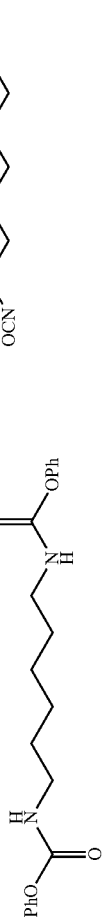 | | 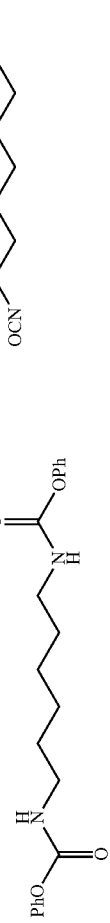 | 86 |
| Example 96 | DPC 0.5 | 88 |  | |  | 85 |

TABLE 18-continued
| | | | | | |
|---|---|---|---|---|---|
| Example 97 | DPC | 0.5 | 86 | 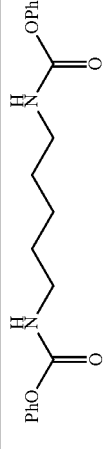 | 86 |
| Example 98 | DPC | 0.5 | 87 | 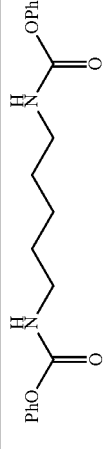 | 81 |
| Example 99 | DPC | 0.5 | 84 | 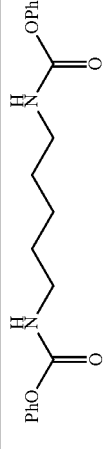 | 84 |
| Example 100 | DPC | 0.5 | 85 | 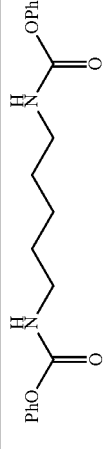 | 85 |

TABLE 19

| | Raw materials for amine compound production | | | Production raw materials for compound having urea linkage | | | | Production of compound having urea linkage | | | |
|---|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 101 | — | — | — | | urea | 0.4 | 2,5-DMPhOH | — | 220 | 140 | 66 |
| Example 102 | — | — | — | | urea | 0.4 | 2,5-DMPhOH | — | 225 | 140 | 69 |
| Example 103 | — | — | — | | urea | 0.4 | 2,5-DMPhOH | — | 225 | 140 | 68 |
| Example 104 | — | — | — | | urea | 0.4 | 2,5-DMPhOH | — | 225 | 140 | 66 |
| Example 105 | — | — | — | | urea | 0.4 | 2,5-DMPhOH | — | 240 | 140 | 67 |

TABLE 19-continued

| | | Production of carbamate | | | | | Production of isocyanate by thermal decomposition of carbamate | |
|---|---|---|---|---|---|---|---|---|
| Example 106 | lysine 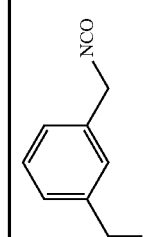 | mono ethanolamine | 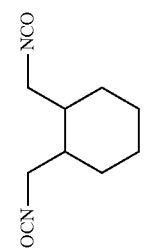 | urea | 0.4 | 2,5-DMPhOH | 255 | 140 | 66 |
| Example 107 | alanine 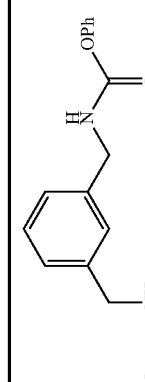 | mono ethanolamine | 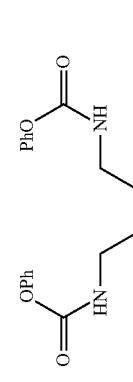 | urea | 0.4 | 2,5-DMPhOH | 245 | 140 | 66 |

| | Carbonate ester | Required carbonate ester equivalence relative to urea conjugate | Carbamate yield | Obtained carbamate | Obtained isocyanate | Thermal decomposition yield (%) |
|---|---|---|---|---|---|---|
| Example 101 | DPC | 0.5 | 86 | | | 82 |
| Example 102 | DPC | 0.5 | 87 | | | 83 |

TABLE 19-continued

| | | | | | |
|---|---|---|---|---|---|
| Example 103 | DPC | 0.5 | (structure) | (structure) | 88 / 84 |
| Example 104 | DPC | 0.5 | (structure) | (structure) | 87 / 81 |
| Example 105 | DPC | 0.5 | (structure) | (structure) | 84 / 82 |
| Example 106 | DPC | 0.5 | (structure) | (structure) | 82 / 79 |
| Example 107 | DPC | 0.5 | (structure) | (structure) | 84 / 81 |

TABLE 20

| | | Raw materials for amine compound production | | Production of compound having urea linkage | | | | | | |
|---|---|---|---|---|---|---|---|---|---|---|
| | Amino acid, amino acid derivative | Amino acid structural formula | Alkanolamine/ alcohol | Production raw materials for compound having urea linkage | | | | | | Raw material amine conversion rate |
| | | | | Amine | Carbonyl source | Equivalence relative to amine terminals | Solvent | Water extraction during production of compound having urea linkage | Thermal dissociation temperature | Reaction temperature | |
| Example 108 | arginine | (structure) | mono ethanolamine | (structure) | urea | 0.4 | 2,5-DMPhOH | — | 260 | 140 | 68 |
| Example 109 | aspartic acid | (structure) | mono ethanolamine | (structure) | urea | 0.4 | 2,5-DMPhOH | — | 250 | 140 | 66 |
| Example 110 | glutamic acid | (structure) | mono ethanolamine | (structure) | urea | 0.4 | 2,5-DMPhOH | — | 240 | 140 | 65 |
| Example 111 | glycine | (structure) | mono ethanolamine | (structure) | urea | 0.4 | 2,5-DMPhOH | — | 255 | 140 | 63 |
| Example 112 | synthetic amino acid | — | mono ethanolamine | (structure) | urea | 0.4 | 2,5-DMPhOH | — | 240 | 140 | 64 |

TABLE 20-continued
| | Production of carbamate | | | | Production of isocyanate by thermal decomposition of carbamate | |
|---|---|---|---|---|---|---|
| | Carbonate ester | Required carbonate ester equivalence relative to urea conjugate | Carbamate yield | Obtained carbamate | Obtained isocyanate | Thermal decomposition yield (%) |
| Example 108 | DPC | 0.5 | 81 | 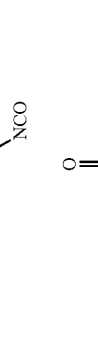 | 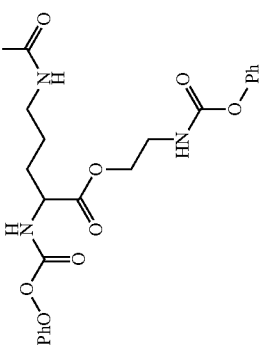 | 83 |
| Example 109 | DPC | 0.5 | 82 | 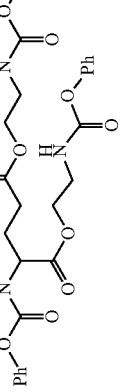 | 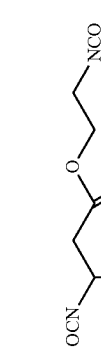 | 82 |
| Example 110 | DPC | 0.5 | 81 |  | 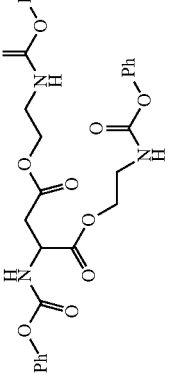 | 79 |

TABLE 20-continued
| | | | | | |
|---|---|---|---|---|---|
| Example 111 | DPC | 0.5 | 84 | 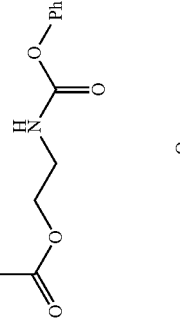 | 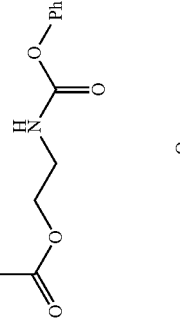 77 |
| Example 112 | DPC | 0.5 | 83 | 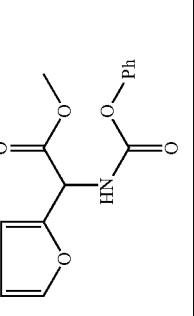 | 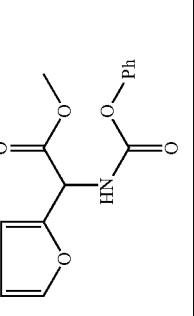 74 |

TABLE 21

| | Raw materials for amine compound production | | Production raw materials for compound having urea linkage | | | | Production of compound having urea linkage | | |
|---|---|---|---|---|---|---|---|---|---|
| Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 113 lysine | 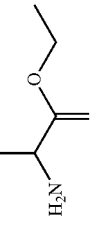 | EtOH |  | urea | 0.4 | 2,5-DMPhOH | — | 250 | 140 | 65 |
| Example 114 lysine | | 1-amino-2-PrOH | | urea | 0.4 | 2,5-DMPhOH | — | 240 | 140 | 66 |

TABLE 21-continued

| | | | | | | | |
|---|---|---|---|---|---|---|---|
| Example 114 | lysine | (structure: lysine) | 2-amino-1-BuOH | (structure) | urea | 0.4 | — | 250 | 140 | 67 |
| Example 116 | glutamic acid | (structure: glutamic acid) | EtOH | (structure) | urea | 0.4 | 2,5-DMPhOH | 260 | 140 | 69 |

| | Production of carbamate | | | Production of isocyanate by thermal decomposition of carbamate | |
|---|---|---|---|---|---|
| | Carbonate ester | Required carbonate ester equivalence relative to urea conjugate | Carbamate yield | Obtained carbamate | Obtained isocyanate | Thermal decomposition yield (%) |
| Example 113 | DPC | 0.5 | 81 | (structure) | (structure) | 75 |

TABLE 21-continued

| Example | | | | | |
|---|---|---|---|---|---|
| Example 114 | DPC | 0.5 | 82 | (structure) | 78 |
| Example 114 | DPC | 0.5 | 84 | (structure) | 76 |
| Example 116 | DPC | 0.5 | 82 | (structure) | 75 |

TABLE 22

| | Raw materials for amine compound production | | | Production raw materials for compound having urea linkage | | | Production of compound having urea linkage | | | |
|---|---|---|---|---|---|---|---|---|---|---|
| Amino acid, amino acid derivative | Amino acid structural formula | Alkanolamine/alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 117 | glutamic acid |  | 1-amino-2-PrOH | 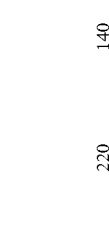 | urea | 0.4 | 2,5-DMPhOH | — | 220 | 140 | 67 |
| Example 118 | glutamic acid |  | 2-amino-1-BuOH | 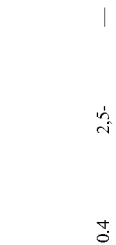 | urea | 0.4 | 2,5-DMPhOH | — | 220 | 140 | 66 |
| Example 119 | — | — | — |  | urea | 0.3 | 2,5-DMPhOH | — | 220 | 140 | 58 |
| Example 120 | — | — | — |  | urea | 0.3 | 2,5-DMPhOH | — | 220 | 140 | 60 |
| Example 121 | — | — | — |  | urea | 0.3 | 2,5-DMPhOH | — | 220 | 140 | 60 |
| Example 122 | — | — | — |  | urea | 0.3 | 2,5-DMPhOH | — | 215 | 140 | 60 |

TABLE 22-continued

| | Carbonate ester | Required carbonate ester equivalence relative to urea conjugate | Carbamate yield | Obtained carbamate | | | Obtained isocyanate | Thermal decomposition yield (%) |
|---|---|---|---|---|---|---|---|---|
| Example 123 | — | — | — | urea | 0.3 | 2,5-DMPhOH | 220 | 140 | 58 |
| Example 124 | — | — | — | urea | 0.3 | 2,5-DMPhOH | 220 | 140 | 58 |

Production of carbamate | Production of isocyanate by thermal decomposition of carbamate

| | Carbonate ester | Required carbonate ester equivalence relative to urea conjugate | Carbamate yield | Obtained carbamate | Obtained isocyanate | Thermal decomposition yield (%) |
|---|---|---|---|---|---|---|
| Example 117 | DPC | 0.5 | 83 | (structure shown) | (structure shown) | 72 |
| Example 118 | DPC | 0.5 | 82 | (structure shown) | (structure shown) | 76 |

TABLE 22-continued
| | | | | | |
|---|---|---|---|---|---|
| Example 119 | DPC | 0.5 | 88 | 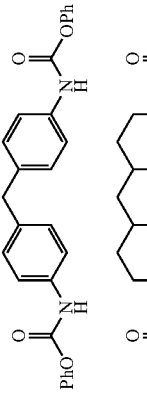 | 85 |
| Example 120 | DPC | 0.5 | 86 | 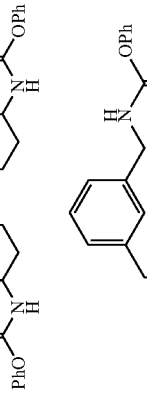 | 86 |
| Example 121 | DPC | 0.5 | 87 | 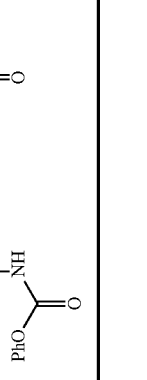 | 81 |
| Example 122 | DPC | 0.5 | 84 |  | 84 |
| Example 123 | DPC | 0.5 | 85 |  | 83 |
| Example 124 | DPC | 0.5 | 86 |  | 82 |

Example 119 to 141

With the exception of altering the amount of carbonic acid derivative used to 0.3 mol relative to each amine terminal, the same operations as Examples 27 to 49 were conducted, yielding the corresponding carbamates and isocyanates shown in Tables 22 to 26.

TABLE 23

| | Raw materials for amine compound production | | Production raw materials for compound having urea linkage | | | | Production of compound having urea linkage | | | |
|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 125 | — | — | — | 1,2-bis(aminomethyl)cyclohexane | urea | 0.3 | 2,5-DMPhOH | — | 210 | 140 | 57 |
| Example 126 | — | — | — | 2,4-diamino-1-methylbenzene | urea | 0.3 | 2,5-DMPhOH | — | 215 | 140 | 58 |
| Example 127 | — | — | — | triamine (branched alkyl triamine) | urea | 0.3 | 2,5-DMPhOH | — | 220 | 140 | 59 |
| Example 128 | — | — | — | 2-aminoethyl methacrylate | urea | 0.3 | 2,5-DMPhOH | — | 225 | 140 | 61 |

TABLE 23-continued

| | | | | | | | |
|---|---|---|---|---|---|---|---|
| Example 129 | lysine | H₂N-(CH₂)₄-CH(NH₂)-COOH | mono ethanolamine | H₂N-CH(NH₂)-(CH₂)₄-NH₂ with ester -O-CH₂-CH₂-NH₂ | urea | 0.3 | 2,5-DMPhOH | — | 225 | 140 | 60 |
| Example 130 | alanine | H₂N-CH(CH₃)-COOH | mono ethanolamine | H₂N-CH(CH₃)-C(O)-O-CH₂-CH₂-NH₂ | urea | 0.3 | 2,5-DMPhOH | — | 240 | 140 | 60 |
| Example 131 | arginine | H₂N-C(=NH)-NH-(CH₂)₃-CH(NH₂)-COOH | mono ethanolamine | arginine ethanolamine ester | urea | 0.3 | 2,5-DMPhOH | — | 255 | 140 | 58 |

Production of carbamate

| | Carbonate ester | Required carbonate ester equivalence relative to urea conjugate | Carbamate yield | Obtained carbamate | Production of isocyanate by thermal decomposition of carbamate — Obtained isocyanate | Thermal decomposition yield (%) |
|---|---|---|---|---|---|---|
| Example 125 | DPC | 0.5 | 87 | PhO-C(O)-CH₂-NH-CH₂-(cyclohexane)-CH₂-NH-C(O)-CH₂-OPh | OCN-CH₂-(cyclohexane)-CH₂-NCO | 83 |

TABLE 23-continued
| | | | | | |
|---|---|---|---|---|---|
| Example 126 | DPC | 0.5 | 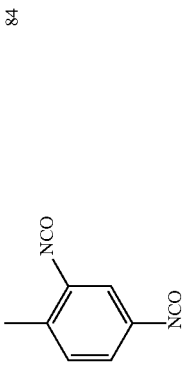 | 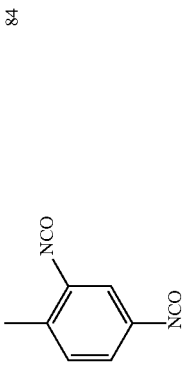 | 84 |
| | | | | | 88 |
| Example 127 | DPC | 0.5 | 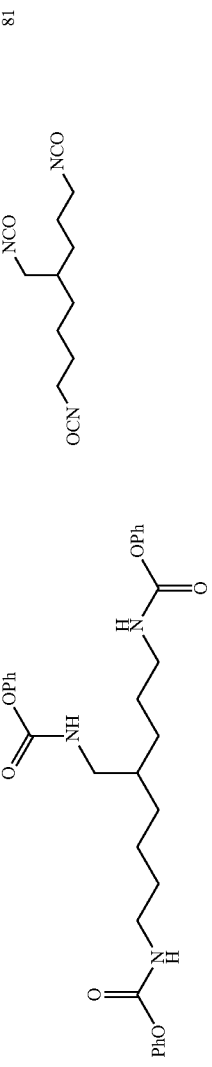 | 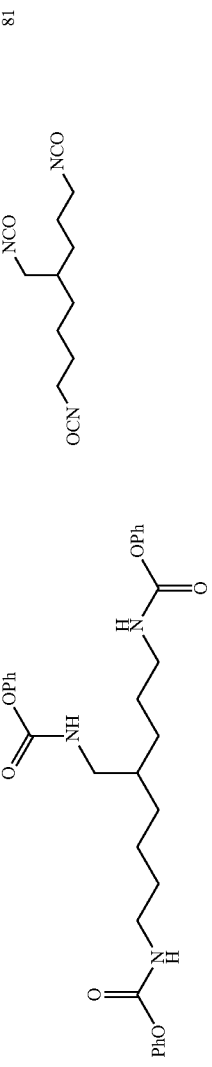 | 81 |
| | | | | | 87 |
| Example 128 | DPC | 0.5 |  |  | 82 |
| | | | | | 84 |
| Example 129 | DPC | 0.5 | 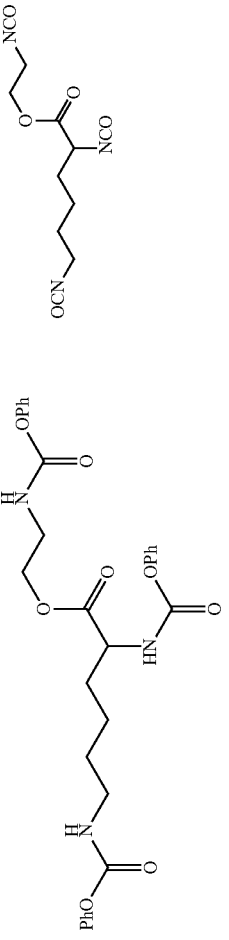 | 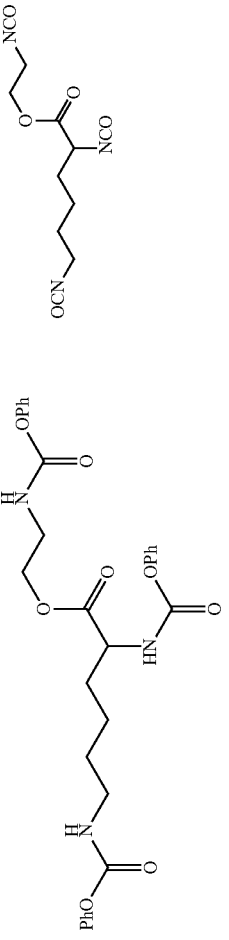 | 79 |
| | | | | | 82 |

TABLE 23-continued

| | | | | | |
|---|---|---|---|---|---|
| Example 130 | DPC | 0.5 | 84 | (structure) | 81 |
| Example 131 | DPC | 0.5 | 81 | (structure) | 83 |

TABLE 24

| | Raw materials for amine compound production | | Production raw materials for compound having urea linkage | | | Production of compound having urea linkage | | | | |
|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 132 | aspartic acid | [H₂N-CH(COOH)-CH₂-COOH] | mono ethanolamine | [aspartic acid bis(2-aminoethyl) ester] | urea | 0.3 | 2,5-DMPhOH | — | 245 | 140 | 60 |
| Example 133 | glutamic acid | [H₂N-CH(COOH)-CH₂-CH₂-COOH] | mono ethanolamine | [glutamic acid bis(2-aminoethyl) ester] | urea | 0.3 | 2,5-DMPhOH | — | 260 | 140 | 60 |
| Example 134 | glycine | [H₂N-CH₂-COOH] | mono ethanolamine | [glycine 2-aminoethyl ester] | urea | 0.3 | 2,5-DMPhOH | — | 250 | 140 | 58 |
| Example 135 | synthetic amino acid | — | mono ethanolamine | [methyl 2-amino-2-(furan-2-yl)acetate] | urea | 0.3 | 2,5-DMPhOH | — | 240 | 140 | 58 |

TABLE 24-continued

| | | | | | | | |
|---|---|---|---|---|---|---|---|
| Example 136 | lysine (structure: H₂N-CH(COOH)-(CH₂)₄-NH₂) | EtOH | lysine methyl ester (H₂N-CH(COOMe)-(CH₂)₄-NH₂) | urea | 0.3 | 2,5-DMPhOH | 255 | 140 | 58 |

| | Production of carbamate | | | Production of isocyanate by thermal decomposition of carbamate | |
|---|---|---|---|---|---|
| | Carbonate ester | Required carbonate ester equivalence relative to urea conjugate | Carbamate yield | Obtained carbamate | Obtained isocyanate | Thermal decomposition yield (%) |
| Example 132 | DPC | 0.5 | 82 | (bis-phenylcarbamate of aspartate diethyl ester) | (diisocyanate of aspartate diethyl ester, OCN-CH(COO-CH₂CH₂-NCO)-CH₂-COO-CH₂CH₂-) | 82 |
| Example 133 | DPC | 0.5 | 81 | (bis-phenylcarbamate of glutamate diethyl ester) | (diisocyanate of glutamate diethyl ester) | 79 |

TABLE 24-continued

| Example | | | | |
|---|---|---|---|---|
| Example 134 | DPC | 0.5 | 84 | [structure with Ph-O-C(=O)-NH-CH2-C(=O)-O-CH2-CH2-NH-C(=O)-O-Ph] | 77 | [structure with OCN-CH2-C(=O)-O-CH2-CH2-NCO] |
| Example 135 | DPC | 0.5 | 83 | [methyl furyl carbamate structure] | 74 | [methyl 2-furyl-2-isocyanatoacetate] |
| Example 136 | DPC | 0.5 | 81 | [bis-carbamate lysine ethyl ester structure] | 75 | [ethyl 2,6-diisocyanatohexanoate] |

TABLE 25

| | Raw materials for amine compound production | | Production raw materials for compound having urea linkage | | | | Production of compound having urea linkage | | | |
|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 137 | lysine | [structure] | 1-amino-2-PrOH | [structure] | urea | 0.3 | 2,5-DMPhOH | — | 240 | 140 | 59 |
| Example 138 | lysine | [structure] | 2-amino-1-BuOH | [structure] | urea | 0.3 | 2,5-DMPhOH | — | 250 | 140 | 60 |
| Example 139 | glutamic acid | [structure] | EtOH | [structure] | urea | 0.3 | 2,5-DMPhOH | — | 240 | 140 | 59 |

TABLE 25-continued

| | | | | | | |
|---|---|---|---|---|---|---|
| Example 140 | glutamic acid (structure: HOOC-CH(NH₂)-CH₂-CH₂-COOH) | 1-amino-2-PrOH | urea | 0.3 | 2,5-DMPhOH | 250 140 58 |

Production of carbamate

| | Carbonate ester | Required carbonate ester equivalence relative to urea conjugate | Carbamate yield | Obtained carbamate |
|---|---|---|---|---|
| Example 137 | DPC | 0.5 | 82 | (structure shown: lysine tri-phenylcarbamate derivative with PhO-C(O)-NH- groups) |

Production of isocyanate by thermal decomposition of carbamate

| Obtained isocyanate | Thermal decomposition yield (%) |
|---|---|
| (structure: NCO-substituted isocyanate from lysine/glutamic derivative showing OCN, NCO groups) | 78 |

TABLE 25-continued

| Example | | | | | |
|---|---|---|---|---|---|
| Example 138 | DPC | 0.5 | 84 | [structure] | 79 |
| Example 139 | DPC | 0.5 | 82 | [structure] | 75 |
| Example 140 | DPC | 0.5 | 83 | [structure] | 72 |

TABLE 26

| | Raw materials for amine compound production | | | Production raw materials for compound having urea linkage | | | Production of compound having urea linkage | | | | |
|---|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 141 | glutamic acid | ![glutamic acid structure] | 2-amino-1-BuOH | ![amine structure with ester linkages and NH2 groups] | urea | 0.3 | 2,5-DMPhOH | — | 260 | 140 | 58 |
| Example 142 | — | — | — | ![H2N-(CH2)n-NH2 structure] | N,N'-dibutyl urea | 0.488 | 2,5-DMPhOH | — | 260 | 140 | 80 |
| Example 143 | — | — | — | ![H2N-(CH2)n-NH2 structure] | N,N'-dibutyl urea | 0.488 | 2,5-DMPhOH | — | 220 | 140 | 78 |
| Example 144 | — | — | — | ![isophorone diamine structure] | N,N'-dibutyl urea | 0.488 | 2,5-DMPhOH | — | 220 | 140 | 78 |
| Example 145 | — | — | — | ![bis(4-aminophenyl)methane structure] | N,N'-dibutyl urea | 0.488 | 2,5-DMPhOH | — | 220 | 140 | 77 |

TABLE 26-continued

| | | | Production of carbamate | | | Production of isocyanate by thermal decomposition of carbamate | | |
|---|---|---|---|---|---|---|---|---|
| | Carbonate ester | Required carbonate ester equivalence relative to urea conjugate | Obtained carbamate | Carbamate yield | | Obtained isocyanate | | Thermal decomposition yield (%) |
| Example 141 | DPC | 0.5 | 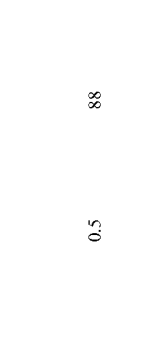 | 82 | |  | | 76 |
| Example 142 | DPC | 0.5 | 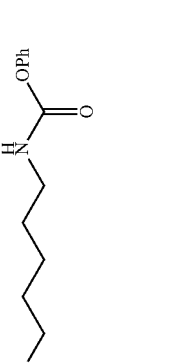 | 88 | |  | | 85 |
| Example 143 | DPC | 0.5 | 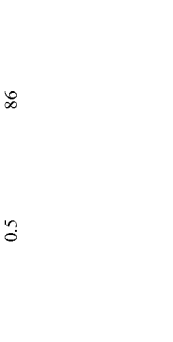 | 86 | |  | | 86 |
| Example 146 | — | — | 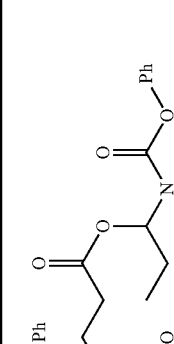 | — | N,N'-dibutyl urea | 0.488 | 2,5-DMPhOH | — | 220 | 140 | 76 |
| Example 147 | — | — | 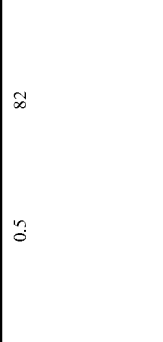 | — | N,N'-dibutyl urea | 0.488 | 2,5-DMPhOH | — | 220 | 140 | 79 |

TABLE 26-continued
| Example 144 | DPC | 0.5 | 87 | 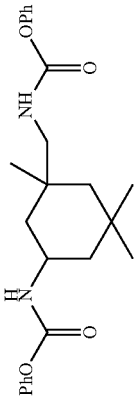 | 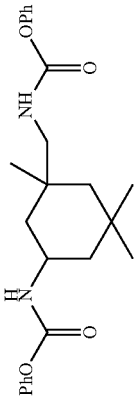 | 81 |
| Example 145 | DPC | 0.5 | 84 | 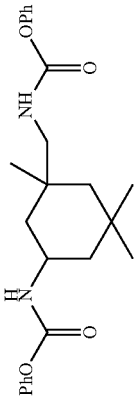 | 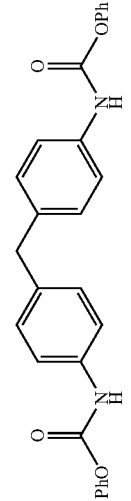 | 84 |
| Example 146 | DPC | 0.5 | 85 | 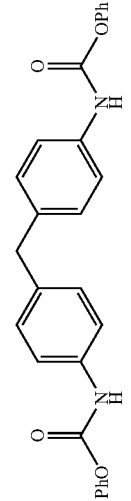 | 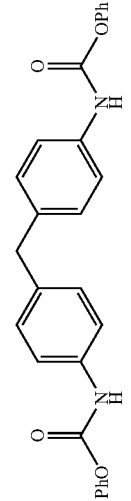 | 83 |
| Example 147 | DPC | 0.5 | 86 | 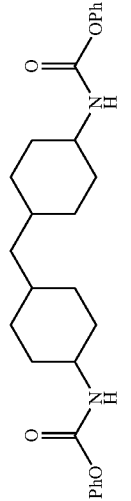 | 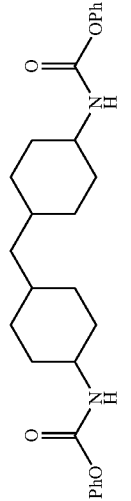 | 82 |

Examples 142 to 164

With the exception of altering the carbonic acid derivative used from urea to N,N'-dibutylurea, the same operations as Examples 27 to 49 were conducted, yielding the corresponding carbamates and isocyanates shown in Tables 26 to 30.

TABLE 27

| | Raw materials for amine compound production | | | Production raw materials for compound having urea linkage | | | | Production of compound having urea linkage | | | |
|---|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 148 | — | — | — | ![amine: H2N-CH2-cyclohexane-CH2-NH2] | N,N-dibutyl urea | 0.488 | 2,5-DMPhOH | — | 215 | 140 | 82 |
| Example 149 | — | — | — | ![amine: 2,4-diamino toluene] | N,N-dibutyl urea | 0.488 | 2,5-DMPhOH | — | 220 | 140 | 82 |
| Example 150 | — | — | — | ![amine: triamine branched] | N,N-dibutyl urea | 0.488 | 2,5-DMPhOH | — | 220 | 140 | 79 |
| Example 151 | — | — | — | ![amine: aminoethyl methacrylate] | N,N-dibutyl urea | 0.488 | 2,5-DMPhOH | — | 210 | 140 | 81 |

TABLE 27-continued

| | | | | | | | | |
|---|---|---|---|---|---|---|---|---|
| Example 152 | lysine | [structure: lysine] | mono ethanolamine | [structure: ethanolamine-NH₂ derivative] | 0.488 | N,N'-dibutyl urea | — | 220 | 140 | 79 |
| Example 153 | alanine | [structure: alanine] | mono ethanolamine | [structure: alanine-ethanolamine ester] | 0.488 | N,N'-dibutyl urea | 2,5-DMPhOH | 225 | 140 | 80 |

Production of carbamate

| | Carbonate ester | Required carbonate ester equivalence relative to urea conjugate | Carbamate yield | Obtained carbamate | Production of isocyanate by thermal decomposition of carbamate | |
|---|---|---|---|---|---|---|
| | | | | | Obtained isocyanate | Thermal decomposition yield (%) |
| Example 148 | DPC | 0.5 | 87 | [structure: bis-phenoxycarbonyl cyclohexane dimethylamine carbamate] | [structure: 1,2-bis(isocyanatomethyl)cyclohexane] | 83 |
| Example 149 | DPC | 0.5 | 88 | [structure: tolylene bis(phenyl carbamate)] | [structure: toluene-2,4-diisocyanate] | 84 |

TABLE 27-continued

| Example 150 | DPC | 0.5 | 87 | (structure) | 81 | (structure) |
| Example 151 | DPC | 0.5 | 84 | (structure) | 82 | (structure) |
| Example 152 | DPC | 0.5 | 82 | (structure) | 79 | (structure) |
| Example 153 | DPC | 0.5 | 84 | (structure) | 81 | (structure) |

TABLE 28

| | Raw materials for amine compound production | | | Production raw materials for compound having urea linkage | | | Production of compound having urea linkage | | | |
|---|---|---|---|---|---|---|---|---|---|---|
| Amino acid, amino acid derivative | Amino acid structural formula | Alkanolamine/alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 154 | arginine | (arginine structure) | mono ethanolamine | (arginine ethanolamine ester) | N,N'-dibutyl urea | 0.488 | 2,5-DMPhOH | — | 225 | 140 | 82 |
| Example 155 | aspartic acid | (aspartic acid structure) | mono ethanolamine | (aspartic acid ethanolamine diester) | N,N'-dibutyl urea | 0.488 | 2,5-DMPhOH | — | 240 | 140 | 79 |
| Example 156 | glutamic acid | (glutamic acid structure) | mono ethanolamine | (glutamic acid ethanolamine diester) | N,N'-dibutyl urea | 0.488 | 2,5-DMPhOH | — | 255 | 140 | 78 |
| Example 157 | glycine | (glycine structure) | mono ethanolamine | (glycine ethanolamine ester) | N,N'-dibutyl urea | 0.488 | 2,5-DMPhOH | — | 245 | 140 | 76 |
| Example 158 | synthetic amino acid | — | mono ethanolamine | (methyl furyl glycinate) | N,N'-dibutyl urea | 0.488 | 2,5-DMPhOH | — | 260 | 140 | 77 |

TABLE 28-continued

| | Production of carbamate | | | | Production of isocyanate by thermal decomposition of carbamate | |
|---|---|---|---|---|---|---|
| | Carbonate ester | Required carbonate ester equivalence relative to urea conjugate | Obtained carbamate | Carbamate yield | Obtained isocyanate | Thermal decomposition yield (%) |
| Example 154 | DPC | 0.5 | [structure: carbamate with PhO-C(=O)-NH- groups] | 81 | [structure: OCN-...-NCO isocyanate] | 83 |
| Example 155 | DPC | 0.5 | [structure: carbamate with PhO-C(=O)-NH- groups] | 82 | [structure: OCN-...-NCO isocyanate] | 82 |

TABLE 28-continued

| | | | | | |
|---|---|---|---|---|---|
| Example 156 | DPC | 0.5 | 81 | [structure] | 79 |
| Example 157 | DPC | 0.5 | 84 | [structure] | 77 |
| Example 158 | DPC | 0.5 | 83 | [structure] | 74 |

TABLE 29

| | Raw materials for amine compound production | | Production raw materials for compound having urea linkage | | | Production of compound having urea linkage | | | | |
|---|---|---|---|---|---|---|---|---|---|---|
| | Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 159 | lysine | (lysine structure with OH) | EtOH | (lysine ethyl ester structure) | N,N'-dibutyl urea | 0.488 | 2,5-DMPhOH | — | 250 | 140 | 77 |
| Example 160 | lysine | (lysine structure with OH) | 1-amino-2-PrOH | (lysine 1-amino-2-propyl ester structure) | N,N'-dibutyl urea | 0.488 | 2,5-DMPhOH | — | 240 | 140 | 80 |

TABLE 29-continued

| | | | | | | | |
|---|---|---|---|---|---|---|---|
| Example 161 | lysine | ![lysine structure] | 2-amino-1-BuOH | ![structure] | N,N'-dibutyl urea | 0.488 | 2,5-DMPhOH | — | 255 | 140 | 81 |
| Example 162 | glutamic acid | ![glutamic acid structure] | EtOH | ![structure] | N,N'-dibutyl urea | 0.488 | 2,5-DMPhOH | — | 240 | 140 | 83 |

| | Production of carbamate | | | Production of isocyanate by thermal decomposition of carbamate | |
|---|---|---|---|---|---|
| | Carbonate ester | Required carbonate ester equivalence relative to urea conjugate | Carbamate yield | Obtained carbamate | Obtained isocyanate | Thermal decomposition yield (%) |
| Example 159 | DPC | 0.5 | 81 | ![carbamate structure] | ![isocyanate structure] | 75 |

TABLE 29-continued

| Example | | | | | |
|---|---|---|---|---|---|
| Example 160 | DPC | 0.5 | 82 | (structure with Ph-O-C(O)-NH groups on lysine-like backbone with ethyl ester) | 78 (diisocyanate structure) |
| Example 161 | DPC | 0.5 | 84 | (similar Ph carbamate structure with propyl) | 76 (diisocyanate structure) |
| Example 162 | DPC | 0.5 | 82 | (Ph-O-C(O)-NH glutamate diethyl ester) | 75 (diisocyanate glutamate diethyl ester) |

TABLE 30

| | Raw materials for amine compound production | | | Production of compound having urea linkage | | | | | | |
|---|---|---|---|---|---|---|---|---|---|---|
| | | | | Production raw materials for compound having urea linkage | | | | | | |
| Amino acid, amino acid derivative | Amino acid structural formula | Alkanolamine/ alcohol | Amine | Carbonyl source | Equivalence relative to amine terminals | Solvent | Water extraction during production of compound having urea linkage | Thermal dissociation temperature | Reaction temperature | Raw material amine conversion rate |
| Example 163 glutamic acid | (structure) | 1-amino-2-PrOH | (structure) | N,N'-dibutyl urea | 0.488 | 2,5-DMPhOH | — | 250 | 140 | 81 |
| Example 164 glutamic acid | (structure) | 2-amino-1-BuOH | (structure) | N,N'-dibutyl urea | 0.488 | 2,5-DMPhOH | — | 240 | 140 | 80 |

TABLE 30-continued

| | Production of carbamate | | | Production of isocyanate by thermal decomposition of carbamate | |
|---|---|---|---|---|---|
| | Carbonate ester | Required carbonate ester equivalence relative to urea conjugate | Carbamate yield | Obtained isocyanate | Thermal decomposition yield (%) |
| Example 163 | DPC | 0.5 | 83 | (structure shown) | 72 |
| Example 164 | DPC | 0.5 | 82 | (structure shown) | 76 |

INDUSTRIAL APPLICABILITY

The method for producing a carbamate according to an embodiment of the present invention uses no phosgene, and enables a reduction in the amount of carbonate ester used. Further, the method for producing an isocyanate according to an embodiment of the present invention is a method that uses the carbamate obtained in the above production method, and is capable of producing numerous varieties of isocyanates.

DESCRIPTION OF REFERENCE SIGNS

1: Raw material preheater
2: Tubular first reactor
3: Tank-like second reactor
4: Partial condenser
10: Thermal decomposition reactor

The invention claimed is:

1. A method for producing a carbamate comprising a step (1) and a step (2) described below:
   (1) a step of producing a compound (A) having a urea linkage, using an organic primary amine having at least one primary amino group per molecule and at least one compound selected from among carbon dioxide and carbonic acid derivatives, at a temperature lower than a thermal dissociation temperature of a urea linkage; and
   (2) a step of reacting the compound (A) with a carbonate ester to produce a carbamate.

2. The method for producing a carbamate according to claim 1, wherein in the step (1), when producing the compound (A) using the organic primary amine and carbon dioxide, reaction is conducted while extracting, from the reaction system, water produced by the reaction between the organic primary amine and carbon dioxide.

3. The method for producing a carbamate according to claim 1, wherein the carbonic acid derivative is at least one compound selected from among N-unsubstituted carbamate esters, N,N-disubstituted ureas, N-substituted ureas, and urea.

4. The method for producing a carbamate according to claim 1, wherein the organic primary amine has two or three primary amino groups per molecule.

5. The method for producing a carbamate according to claim 1, wherein the organic primary amine is at least one compound selected from among amino acid esters and salts of amino acid esters.

6. The method for producing a carbamate according to claim 1, wherein
   the organic primary amine has a carboxy group, and
   the method further comprises a step (Y) described below, either before the step (1), or after the step (1) but before the step (2):
   (Y) a step of esterifying the carboxy group of the organic primary amine, or esterifying the carboxy group of the compound (A) obtained in the step (1).

7. The method for producing a carbamate according to claim 1, wherein the organic primary amine has three primary amino groups per molecule.

8. The method for producing a carbamate according to claim 3, wherein a molar amount of the carbonic acid derivative is less than 0.5 times a molar amount of primary amino groups in the organic primary amine.

9. The method for producing a carbamate according to claim 1, wherein in the step (1), reaction is conducted in presence of an aromatic hydroxy compound.

10. A method for producing an isocyanate by subjecting the carbamate obtained using the method according to claim 1 to a thermal decomposition reaction.

11. The method for producing a carbamate according to claim 8, wherein in the step (1), reaction is conducted in presence of an aromatic hydroxy compound.

* * * * *